(12) United States Patent
Barnes et al.

(10) Patent No.: US 11,783,478 B2
(45) Date of Patent: Oct. 10, 2023

(54) METHODS AND SYSTEMS FOR EVALUATION OF IMMUNE CELL INFILTRATE IN TUMOR SAMPLES

(71) Applicant: Ventana Medical Systems, Inc., Tucson, AZ (US)

(72) Inventors: Michael Barnes, Oro Valley, AZ (US); Joerg Bredno, San Francisco, CA (US); Rebecca C. Bowermaster, Tucson, AZ (US); Srinivas Chukka, San Jose, CA (US); Wen-Wei Liu, Tucson, AZ (US); Kandavel Shanmugam, Oro Valley, AZ (US); Junming Zhu, Oro Valley, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 0 days.

(21) Appl. No.: 17/569,270

(22) Filed: Jan. 5, 2022

(65) Prior Publication Data

US 2022/0270242 A1  Aug. 25, 2022

Related U.S. Application Data

(63) Continuation of application No. 16/752,494, filed on Jan. 24, 2020, now Pat. No. 11,250,566, which is a (Continued)

(51) Int. Cl.
*G06T 7/00* (2017.01)
*G01N 33/574* (2006.01)
*G16H 10/00* (2018.01)

(52) U.S. Cl.
CPC ......... *G06T 7/0012* (2013.01); *G01N 33/574* (2013.01); *G06T 2207/10056* (2013.01);
(Continued)

(58) Field of Classification Search
CPC ............... G06T 7/0012; G06T 2207/20; G06T 2207/30096; G01N 33/50
See application file for complete search history.

(56) References Cited

U.S. PATENT DOCUMENTS 8,481,271 B2   7/2013  Galon
9,298,968 B1   3/2016  Peljto
(Continued)

FOREIGN PATENT DOCUMENTS

EP    1777523 A1 *  4/2007  ........... C12Q 1/6886
WO    2013186374 A1   12/2013
(Continued)

OTHER PUBLICATIONS

Hermitte, F. (2016). Biomarkers immune monitoring technology primer: Immunoscore® Colon. Journal for ImmunoTherapy of Cancer, 4(1). https://doi.org/10.1186/s40425-016-0161-x (Year: 2016).*
(Continued)

*Primary Examiner* — John Villecco
*Assistant Examiner* — Courtney Joan Nelson
(74) *Attorney, Agent, or Firm* — Ventana Medical Systems, Inc.

(57) ABSTRACT

Immune context scores are calculated for tumor tissue samples using continuous scoring functions. Feature metrics for at least one immune cell marker are calculated for a region or regions of interest, the feature metrics including at least a quantitative measure of human CD3 or total lymphocyte counts. A continuous scoring function is then applied to a feature vector including the feature metric and at least one additional metric related to an immunological biomarker, the output of which is an immune context score. The immune context score may then be plotted as a function of a diagnostic or treatment metric, such as a prognostic metric (e.g. overall survival, disease-specific survival, pro-
(Continued)

gression-free survival) or a predictive metric (e.g. likelihood of response to a particular treatment course). The immune context score may then be incorporated into diagnostic and/or treatment decisions.

13 Claims, 23 Drawing Sheets

Specification includes a Sequence Listing.

Related U.S. Application Data continuation of application No. PCT/EP2018/069896, filed on Jul. 23, 2018.

(60) Provisional application No. 62/675,707, filed on May 23, 2018, provisional application No. 62/536,373, filed on Jul. 24, 2017.

(52) U.S. Cl.
CPC ............... *G06T 2207/20081* (2013.01); *G06T 2207/20104* (2013.01); *G06T 2207/30024* (2013.01); *G06T 2207/30096* (2013.01); *G16H 10/00* (2018.01)

(56) References Cited

U.S. PATENT DOCUMENTS

| 2013/0310267 A1 | 11/2013 | Gustavson et al. |
| 2020/0234442 A1 | 7/2020 | Barnes |

FOREIGN PATENT DOCUMENTS

| WO | WO-2013186374 A1 * | 12/2013 | ......... G01N 33/5047 |
| WO | 2015124737 A1 | 8/2015 | |
| WO | WO-2015121465 A1 * | 8/2015 | ........... C12Q 1/6886 |
| WO | WO-2015124737 A1 * | 8/2015 | ......... G01N 15/1463 |
| WO | WO-2015164501 A2 * | 10/2015 | ........... C12Q 1/6886 |
| WO | 2017103086 A1 | 6/2017 | |
| WO | 2017194556 A1 | 11/2017 | |
| WO | 2019020556 A1 | 1/2019 | |

OTHER PUBLICATIONS

Wen, T et al, A Four-Factor Immunoscore System That Predicts Clinical Outcome for Stage II/III Gastric Cancer, and Immunol Res, (2017), pp. 524-534, vol. 5 Issue 7 (Year: 2017).*
Anitei et al., Prognostic and Predictive Values of the Immunoscore in Patients with Rectal Cancer, Clinical Cancer Research, 2014, pp. 1891-1899, vol. 20, Issue 7.
Anitei Supplemental Data, retrieved Apr. 20, 2020, pp. 1-5.
Chen et al., Automatic Lymphocyte Detection in H&E Images with Deep Neural Networks, arXiv:1612.03217v1 (submitted Dec. 9, 2016; available at https://arxiv.org/abs/1612.03217), pp. 1-11.
Donnem, T et al, Strategies for clinical implementation of TNMImmunoscore in resected nonsmall-cell lung cancer, Ann Oncol, (2015), pp. 225-232, vol. 27 Issue 2.
Forrest et al., Comparison of visual and automated assessment of tumour inflammatory infiltrates in patients with colorectal cancer, European Journal of Cancer, 2014, pp. 544-552, vol. 50, Issue 3.
Galon et al., Towards the introduction of the 'Immunoscore' in the classification of malignant tumours, Journal of Pathology, 2014, pp. 199-209, vol. 232, Issue 2.
Galon et al., Validation of the Immunoscore (IM) as a prognostic marker in stage I/II/III colon cancer: Results of a worldwide consortium-based analysis of 1,336 patients. Powerpoint presentation (2016), pp. 1-29 (available at http://meetinglibrary.asco.org/content/168666-176) ("Galon (2016a)").
Galon et al., Validation of the Immunoscore (IM) as a prognostic marker in stage I/II/III colon cancer: Results of a worldwide consortium-based analysis of 1,336 patients., J. Clin. Oncol., vol. 34, suppl. Abstract No. 3500 (2016) pp. 1-2 (available at http://meetinglibrary.asco.org/content/168666-176) ("Galon (2016a)").
Hermitte, F et al, Biomarkers immune monitoring technology primer: Immunoscore® Colon, J Immun Cancer, (2016), pp. 2-3, vol. 232.
International Search Report and Written Opinion dated Jan. 4, 2019 in connection with PCT/EP2018/069896 filed Jul. 23, 2018, pp. 1-20.
International Search Report and Written Opinion dated Jun. 17, 2019 in connection with PCT/EP2019/052373 filed Jan. 31, 2019, pp. 1-20.
International Search Report and Written Opinion dated Apr. 30, 2020 in connection with PCT/EP2020/052737 filed Feb. 4, 2020, 16 pages.
Jass et al., A new prognostic classification of rectal cancer,, The Lancet, 1987, pp. 1303-1306, vol. 329, Issue 8545.
Jass, Jr, Lymphocytic infiltration and survival in rectal cancer, Journal of Clinical Pathology, 1986, pp. 585-589, vol. 39, Issue 6.
Kwak et al., Immunoscore encompassing CD3+ and CD8+ T Cell densities in distant metastasis in a robust prognostic marker for advanced colorectal cancer, Oncotarget, 2016, pp. 81778-81790, vol. 7, No. 49.
Le, Dung T. et al., Mismatch repair deficiency predicts response of solid tumors to PD-1 blockade, Science, Jul. 28, 2017, pp. 409-413, 357.
Lee et al., Clinical Impact of Tumor-infiltrating Lymphocytes for Survival in Curatively Resected Stage IV Colon Cancer with Isolated Liver or Lung Metastasis, Annals of Surgical Oncology, Dec. 6, 2012, pp. 697-702, vol. 20, No. 2.
LorsakulAuranuch et al., Validation of multiplex immunohistochemistry assays using automated image analysis, Validation of multiplex immunohistochemistry assays using automated image analysis, Mar. 6, 2018, p. 105810J-1-105810J-8(8pages), XP060104327, ISSN 1605-7422, DOI 10.1117/12.2293168, ISBN 978-1-5106-0027-0, 10581, Roche Tissue Diagnostics, WO.
Mei et al., Tumour-infiltrating inflammation and prognosis in colorectal cancer: systematic review and meta-analysis, British Journal of Cancer, 2014, pp. 11595-11605, vol. 110.
Obeid, J et al, Heterogeneity of CD8+ tumor-infiltrating lymphocytes in non-small-cell lung cancer: impact on patient prognostic assessments and comparison of quantification by different sampling strategies, Can Immun Immuno, (2016), pp. 33-43, vol. 66 Issue 1.
Pages et al., Immune infiltration in human tumors: a prognostic factor that should not be ignored, Oncogene, 2010, pp. 1093-1102, vol. 29.
Sarkar, Anindya, et al., A Robust Method for Inter-Marker Whole Slide Registration of Digital Pathology Images Using Lines Based Features, 2014 IEEE 11th Internat. Symposium on Biomedical Imaging (ISBI), 2014, 762-765.
Venook et al., Impact of primary (1°) tumor location on overall survival (OS) and progression-free survival (PFS) in patients (pts) with metastatic colorectal cancer (mCRC): Analysis of CALGB/SWOG 80405 (Alliance), Journal of Clinical Oncology, 2016, pp. 1-24, 34; suppl; abstr 3504.
Venook et al., Impact of primary (1°) tumor location on overall survival (OS) and progression-free survival (PFS) in patients (pts) with metastatic colorectal cancer (mCRC): Analysis of CALGB/SWOG 80405 (Alliance), Journal of Clinical Oncology, 2016, pp. 1-5, 34; suppl; abstr 3504.
Ward-Hartstonge et al., Inclusion of BLIMP-1+ effector regulatory T cells improves the Immunoscore in a cohort of New Zealand colorectal cancer patients: a pilot study, Cancer Immunol Immunother, 2017, pp. 515-522, vol. 66, No. 4.
Wen, T et al, A Four-Factor Immunoscore System That Predicts Clinical Outcome for Stage II/III Gastric Cancer, Canc Immunol Res, (2017), pp. 524-534, vol. 5 Issue 7.
Yoon et al., Intertumoral Heterogeneity of CD3 + and CD8 + T-Cell Densities in the Microenvironment of DNA Mismatch-Repair-Deicient Colon Cancers: Implications for Prognosis, Clinical Cancer Research, Oct. 9, 2018, pp. 125-133, vol. 25, No. 1.

\* cited by examiner

SEQUENCE LISTING

```
<160> NUMBER OF SEQ ID NOS: 15

<210> SEQ ID NO 1
<211> LENGTH: 182
<212> TYPE: PRT
<213> ORGANISM: Homo sapiens

<400> SEQUENCE: 1

Met Glu Gln Gly Lys Gly Leu Ala Val Leu Ile Leu Ala Ile Ile Leu
1               5                   10                  15

Leu Gln Gly Thr Leu Ala Gln Ser Ile Lys Gly Asn His Leu Val Lys
            20                  25                  30

Val Tyr Asp Tyr Gln Glu Asp Gly Ser Val Leu Leu Thr Cys Asp Ala
        35                  40                  45

Glu Ala Lys Asn Ile Thr Trp Phe Lys Asp Gly Lys Met Ile Gly Phe
    50                  55                  60

Leu Thr Glu Asp Lys Lys Lys Trp Asn Leu Gly Ser Asn Ala Lys Asp
65                  70                  75                  80

Pro Arg Gly Met Tyr Gln Cys Lys Gly Ser Gln Asn Lys Ser Lys Pro
                85                  90                  95

Leu Gln Val Tyr Tyr Arg Met Cys Gln Asn Cys Ile Glu Leu Asn Ala
            100                 105                 110

Ala Thr Ile Ser Gly Phe Leu Phe Ala Glu Ile Val Ser Ile Phe Val
        115                 120                 125

Leu Ala Val Gly Val Tyr Phe Ile Ala Gly Gln Asp Gly Val Arg Gln
    130                 135                 140

Ser Arg Ala Ser Asp Lys Gln Thr Leu Leu Pro Asn Asp Gln Leu Tyr
145                 150                 155                 160

Gln Pro Leu Lys Asp Arg Glu Asp Asp Gln Tyr Ser His Leu Gln Gly
                165                 170                 175

Asn Gln Leu Arg Arg Asn
            180

<210> SEQ ID NO 2
<211> LENGTH: 171
<212> TYPE: PRT
<213> ORGANISM: Homo sapiens

<400> SEQUENCE: 2

Met Glu His Ser Thr Phe Leu Ser Gly Leu Val Leu Ala Thr Leu Leu
1               5                   10                  15

Ser Gln Val Ser Pro Phe Lys Ile Pro Ile Glu Glu Leu Glu Asp Arg
            20                  25                  30

Val Phe Val Asn Cys Asn Thr Ser Ile Thr Trp Val Glu Gly Thr Val
        35                  40                  45
```

```
Gly Thr Leu Leu Ser Asp Ile Thr Arg Leu Asp Leu Gly Lys Arg Ile
     50                  55                  60

Leu Asp Pro Arg Gly Ile Tyr Arg Cys Asn Gly Thr Asp Ile Tyr Lys
 65                  70                  75                  80

Asp Lys Glu Ser Thr Val Gln Val His Tyr Arg Met Cys Gln Ser Cys
                 85                  90                  95

Val Glu Leu Asp Pro Ala Thr Val Ala Gly Ile Ile Val Thr Asp Val
            100                 105                 110

Ile Ala Thr Leu Leu Leu Ala Leu Gly Val Phe Cys Phe Ala Gly His
        115                 120                 125

Glu Thr Gly Arg Leu Ser Gly Ala Ala Asp Thr Gln Ala Leu Leu Arg
130                 135                 140

Asn Asp Gln Val Tyr Gln Pro Leu Arg Asp Arg Asp Asp Ala Gln Tyr
145                 150                 155                 160

Ser His Leu Gly Gly Asn Trp Ala Arg Asn Lys
                165                 170

<210> SEQ ID NO 3
<211> LENGTH: 207
<212> TYPE: PRT
<213> ORGANISM: Homo sapiens

<400> SEQUENCE: 3

Met Gln Ser Gly Thr His Trp Arg Val Leu Gly Leu Cys Leu Leu Ser
 1               5                  10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
 50                  55                  60

Asn Ile Gly Gly Asp Glu Asp Asp Lys Asn Ile Gly Ser Asp Glu Asp
 65                  70                  75                  80

His Leu Ser Leu Lys Glu Phe Ser Glu Leu Glu Gln Ser Gly Tyr Tyr
                 85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
        195                 200                 205

<210> SEQ ID NO 4
<211> LENGTH: 164
<212> TYPE: PRT
<213> ORGANISM: Homo sapiens

<400> SEQUENCE: 4
```

```
Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
                35                  40                  45

Leu Phe Leu Arg Val Lys Phe Ser Arg Ser Ala Asp Ala Pro Ala Tyr
50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Gln Arg Arg Lys Asn Pro Gln Glu Gly Leu Tyr Asn
            100                 105                 110

Glu Leu Gln Lys Asp Lys Met Ala Glu Ala Tyr Ser Glu Ile Gly Met
                115                 120                 125

Lys Gly Glu Arg Arg Arg Gly Lys Gly His Asp Gly Leu Tyr Gln Gly
            130                 135                 140

Leu Ser Thr Ala Thr Lys Asp Thr Tyr Asp Ala Leu His Met Gln Ala
145                 150                 155                 160

Leu Pro Pro Arg

<210> SEQ ID NO 5
<211> LENGTH: 458
<212> TYPE: PRT
<213> ORGANISM: Homo sapiens

<400> SEQUENCE: 5

Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
            20                  25                  30

Lys Gly Asp Thr Val Glu Leu Thr Cys Thr Ala Ser Gln Lys Lys Ser
            35                  40                  45

Ile Gln Phe His Trp Lys Asn Ser Asn Gln Ile Lys Ile Leu Gly Asn
50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
            100                 105                 110

Asp Gln Lys Glu Glu Val Gln Leu Leu Val Phe Gly Leu Thr Ala Asn
            115                 120                 125

Ser Asp Thr His Leu Leu Gln Gly Gln Ser Leu Thr Leu Thr Leu Glu
            130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
            165                 170                 175

Gln Asp Ser Gly Thr Trp Thr Cys Thr Val Leu Gln Asn Gln Lys Lys
            180                 185                 190

Val Glu Phe Lys Ile Asp Ile Val Val Leu Ala Phe Gln Lys Ala Ser
            195                 200                 205
```

```
Ser Ile Val Tyr Lys Lys Glu Gly Glu Gln Val Glu Phe Ser Phe Pro
    210                 215                 220

Leu Ala Phe Thr Val Glu Lys Leu Thr Gly Ser Gly Glu Leu Trp Trp
225                 230                 235                 240

Gln Ala Glu Arg Ala Ser Ser Lys Ser Trp Ile Thr Phe Asp Leu
                245                 250                 255

Lys Asn Lys Glu Val Ser Val Lys Arg Val Thr Gln Asp Pro Lys Leu
                260                 265                 270

Gln Met Gly Lys Lys Leu Pro Leu His Leu Thr Leu Pro Gln Ala Leu
                275                 280                 285

Pro Gln Tyr Ala Gly Ser Gly Asn Leu Thr Leu Ala Leu Glu Ala Lys
            290                 295                 300

Thr Gly Lys Leu His Gln Glu Val Asn Leu Val Val Met Arg Ala Thr
305                 310                 315                 320

Gln Leu Gln Lys Asn Leu Thr Cys Glu Val Trp Gly Pro Thr Ser Pro
                325                 330                 335

Lys Leu Met Leu Ser Leu Lys Leu Glu Asn Lys Glu Ala Lys Val Ser
                340                 345                 350

Lys Arg Glu Lys Ala Val Trp Val Leu Asn Pro Glu Ala Gly Met Trp
            355                 360                 365

Gln Cys Leu Leu Ser Asp Ser Gly Gln Val Leu Leu Glu Ser Asn Ile
    370                 375                 380

Lys Val Leu Pro Thr Trp Ser Thr Pro Val Gln Pro Met Ala Leu Ile
385                 390                 395                 400

Val Leu Gly Gly Val Ala Gly Leu Leu Leu Phe Ile Gly Leu Gly Ile
                405                 410                 415

Phe Phe Cys Val Arg Cys Arg His Arg Arg Arg Gln Ala Glu Arg Met
                420                 425                 430

Ser Gln Ile Lys Arg Leu Leu Ser Glu Lys Lys Thr Cys Gln Cys Pro
            435                 440                 445

His Arg Phe Gln Lys Thr Cys Ser Pro Ile
            450                 455
```

<210> SEQ ID NO 6
<211> LENGTH: 235
<212> TYPE: PRT
<213> ORGANISM: Homo sapiens

<400> SEQUENCE: 6

```
Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
                20                  25                  30

Trp Asn Leu Gly Glu Thr Val Glu Leu Lys Cys Gln Val Leu Leu Ser
            35                  40                  45

Asn Pro Thr Ser Gly Cys Ser Trp Leu Phe Gln Pro Arg Gly Ala Ala
        50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95

Thr Phe Val Leu Thr Leu Ser Asp Phe Arg Arg Glu Asn Glu Gly Tyr
                100                 105                 110

Tyr Phe Cys Ser Ala Leu Ser Asn Ser Ile Met Tyr Phe Ser His Phe
            115                 120                 125
```

```
Val Pro Val Phe Leu Pro Ala Lys Pro Thr Thr Thr Pro Ala Pro Arg
        130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
                180                 185                 190

Cys Gly Val Leu Leu Leu Ser Leu Val Ile Thr Leu Tyr Cys Asn His
                195                 200                 205

Arg Asn Arg Arg Arg Val Cys Lys Cys Pro Arg Pro Val Val Lys Ser
        210                 215                 220

Gly Asp Lys Pro Ser Leu Ser Ala Arg Tyr Val
225                 230                 235

<210> SEQ ID NO 7
<211> LENGTH: 210
<212> TYPE: PRT
<213> ORGANISM: Homo sapiens

<400> SEQUENCE: 7

Met Arg Pro Arg Leu Trp Leu Leu Leu Ala Ala Gln Leu Thr Val Leu
1               5                   10                  15

His Gly Asn Ser Val Leu Gln Gln Thr Pro Ala Tyr Ile Lys Val Gln
                20                  25                  30

Thr Asn Lys Met Val Met Leu Ser Cys Glu Ala Lys Ile Ser Leu Ser
            35                  40                  45

Asn Met Arg Ile Tyr Trp Leu Arg Gln Arg Gln Ala Pro Ser Ser Asp
    50                  55                  60

Ser His His Glu Phe Leu Ala Leu Trp Asp Ser Ala Lys Gly Thr Ile
65                  70                  75                  80

His Gly Glu Glu Val Glu Gln Glu Lys Ile Ala Val Phe Arg Asp Ala
                85                  90                  95

Ser Arg Phe Ile Leu Asn Leu Thr Ser Val Lys Pro Glu Asp Ser Gly
                100                 105                 110

Ile Tyr Phe Cys Met Ile Val Gly Ser Pro Glu Leu Thr Phe Gly Lys
                115                 120                 125

Gly Thr Gln Leu Ser Val Val Asp Phe Leu Pro Thr Thr Ala Gln Pro
        130                 135                 140

Thr Lys Lys Ser Thr Leu Lys Lys Arg Val Cys Arg Leu Pro Arg Pro
145                 150                 155                 160

Glu Thr Gln Lys Gly Pro Leu Cys Ser Pro Ile Thr Leu Gly Leu Leu
                165                 170                 175

Val Ala Gly Val Leu Val Leu Leu Val Ser Leu Gly Val Ala Ile His
                180                 185                 190

Leu Cys Cys Arg Arg Arg Arg Ala Arg Leu Arg Phe Met Lys Gln Phe
                195                 200                 205

Tyr Lys
210

<210> SEQ ID NO 8
<211> LENGTH: 223
<212> TYPE: PRT
<213> ORGANISM: Homo sapiens

<400> SEQUENCE: 8
```

```
Met Ala Cys Leu Gly Phe Gln Arg His Lys Ala Gln Leu Asn Leu Ala
1               5                   10                  15

Thr Arg Thr Trp Pro Cys Thr Leu Phe Phe Leu Leu Phe Ile Pro
            20                  25                  30

Val Phe Cys Lys Ala Met His Val Ala Gln Pro Ala Val Val Leu Ala
                35                  40                  45

Ser Ser Arg Gly Ile Ala Ser Phe Val Cys Glu Tyr Ala Ser Pro Gly
        50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
                100                 105                 110

Asn Leu Thr Ile Gln Gly Leu Arg Ala Met Asp Thr Gly Leu Tyr Ile
            115                 120                 125

Cys Lys Val Glu Leu Met Tyr Pro Pro Pro Tyr Tyr Leu Gly Ile Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
                180                 185                 190

Arg Ser Pro Leu Thr Thr Gly Val Tyr Val Lys Met Pro Pro Thr Glu
            195                 200                 205

Pro Glu Cys Glu Lys Gln Phe Gln Pro Tyr Phe Ile Pro Ile Asn
            210                 215                 220

<210> SEQ ID NO 9
<211> LENGTH: 431
<212> TYPE: PRT
<213> ORGANISM: Homo sapiens

<400> SEQUENCE: 9

Met Pro Asn Pro Arg Pro Gly Lys Pro Ser Ala Pro Ser Leu Ala Leu
1               5                   10                  15

Gly Pro Ser Pro Gly Ala Ser Pro Ser Trp Arg Ala Ala Pro Lys Ala
            20                  25                  30

Ser Asp Leu Leu Gly Ala Arg Gly Pro Gly Gly Thr Phe Gln Gly Arg
        35                  40                  45

Asp Leu Arg Gly Gly Ala His Ala Ser Ser Ser Leu Asn Pro Met
    50                  55                  60

Pro Pro Ser Gln Leu Gln Leu Pro Thr Leu Pro Leu Val Met Val Ala
65                  70                  75                  80

Pro Ser Gly Ala Arg Leu Gly Pro Leu Pro His Leu Gln Ala Leu Leu
                85                  90                  95

Gln Asp Arg Pro His Phe Met His Gln Leu Ser Thr Val Asp Ala His
                100                 105                 110

Ala Arg Thr Pro Val Leu Gln Val His Pro Leu Glu Ser Pro Ala Met
            115                 120                 125

Ile Ser Leu Thr Pro Pro Thr Thr Ala Thr Gly Val Phe Ser Leu Lys
    130                 135                 140

Ala Arg Pro Gly Leu Pro Pro Gly Ile Asn Val Ala Ser Leu Glu Trp
```

```
                145                 150                 155                 160
        Val Ser Arg Glu Pro Ala Leu Leu Cys Thr Phe Pro Asn Pro Ser Ala
                    165                 170                 175
        Pro Arg Lys Asp Ser Thr Leu Ser Ala Val Pro Gln Ser Ser Tyr Pro
                    180                 185                 190
        Leu Leu Ala Asn Gly Val Cys Lys Trp Pro Gly Cys Glu Lys Val Phe
                    195                 200                 205
        Glu Glu Pro Glu Asp Phe Leu Lys His Cys Gln Ala Asp His Leu Leu
                    210                 215                 220
        Asp Glu Lys Gly Arg Ala Gln Cys Leu Leu Gln Arg Glu Met Val Gln
        225                 230                 235                 240
        Ser Leu Glu Gln Gln Leu Val Leu Glu Lys Glu Lys Leu Ser Ala Met
                        245                 250                 255
        Gln Ala His Leu Ala Gly Lys Met Ala Leu Thr Lys Ala Ser Ser Val
                    260                 265                 270
        Ala Ser Ser Asp Lys Gly Ser Cys Cys Ile Val Ala Ala Gly Ser Gln
                    275                 280                 285
        Gly Pro Val Val Pro Ala Trp Ser Gly Pro Arg Glu Ala Pro Asp Ser
                290                 295                 300
        Leu Phe Ala Val Arg Arg His Leu Trp Gly Ser His Gly Asn Ser Thr
        305                 310                 315                 320
        Phe Pro Glu Phe Leu His Asn Met Asp Tyr Phe Lys Phe His Asn Met
                        325                 330                 335
        Arg Pro Pro Phe Thr Tyr Ala Thr Leu Ile Arg Trp Ala Ile Leu Glu
                        340                 345                 350
        Ala Pro Glu Lys Gln Arg Thr Leu Asn Glu Ile Tyr His Trp Phe Thr
                    355                 360                 365
        Arg Met Phe Ala Phe Phe Arg Asn His Pro Ala Thr Trp Lys Asn Ala
                370                 375                 380
        Ile Arg His Asn Leu Ser Leu His Lys Cys Phe Val Arg Val Glu Ser
        385                 390                 395                 400
        Glu Lys Gly Ala Val Trp Thr Val Asp Glu Leu Glu Phe Arg Lys Lys
                        405                 410                 415
        Arg Ser Gln Arg Pro Ser Arg Cys Ser Asn Pro Thr Pro Gly Pro
                        420                 425                 430

<210> SEQ ID NO 10
<211> LENGTH: 288
<212> TYPE: PRT
<213> ORGANISM: Homo sapiens

<400> SEQUENCE: 10

Met Gln Ile Pro Gln Ala Pro Trp Pro Val Val Trp Ala Val Leu Gln
        1               5                   10                  15
        Leu Gly Trp Arg Pro Gly Trp Phe Leu Asp Ser Pro Asp Arg Pro Trp
                    20                  25                  30
        Asn Pro Pro Thr Phe Ser Pro Ala Leu Leu Val Val Thr Glu Gly Asp
                        35                  40                  45
        Asn Ala Thr Phe Thr Cys Ser Phe Ser Asn Thr Ser Glu Ser Phe Val
                    50                  55                  60
        Leu Asn Trp Tyr Arg Met Ser Pro Ser Asn Gln Thr Asp Lys Leu Ala
        65                  70                  75                  80
        Ala Phe Pro Glu Asp Arg Ser Gln Pro Gly Gln Asp Cys Arg Phe Arg
                        85                  90                  95
```

-continued

```
Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285
```

<210> SEQ ID NO 11
<211> LENGTH: 290
<212> TYPE: PRT
<213> ORGANISM: Homo sapiens

<400> SEQUENCE: 11

```
Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190
```

Val Thr Ser Thr Leu Arg Ile Asn Thr Thr Asn Glu Ile Phe Tyr
            195                 200                 205

Cys Thr Phe Arg Arg Leu Asp Pro Glu Glu Asn His Thr Ala Glu Leu
210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
            245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
            275                 280                 285

Glu Thr
    290

<210> SEQ ID NO 12
<211> LENGTH: 273
<212> TYPE: PRT
<213> ORGANISM: Homo sapiens

<400> SEQUENCE: 12

Met Ile Phe Leu Leu Leu Met Leu Ser Leu Glu Leu Gln Leu His Gln
1               5                   10                  15

Ile Ala Ala Leu Phe Thr Val Thr Val Pro Lys Glu Leu Tyr Ile Ile
            20                  25                  30

Glu His Gly Ser Asn Val Thr Leu Glu Cys Asn Phe Asp Thr Gly Ser
        35                  40                  45

His Val Asn Leu Gly Ala Ile Thr Ala Ser Leu Gln Lys Val Glu Asn
    50                  55                  60

Asp Thr Ser Pro His Arg Glu Arg Ala Thr Leu Leu Glu Glu Gln Leu
65                  70                  75                  80

Pro Leu Gly Lys Ala Ser Phe His Ile Pro Gln Val Gln Val Arg Asp
                85                  90                  95

Glu Gly Gln Tyr Gln Cys Ile Ile Ile Tyr Gly Val Ala Trp Asp Tyr
            100                 105                 110

Lys Tyr Leu Thr Leu Lys Val Lys Ala Ser Tyr Arg Lys Ile Asn Thr
        115                 120                 125

His Ile Leu Lys Val Pro Glu Thr Asp Glu Val Glu Leu Thr Cys Gln
    130                 135                 140

Ala Thr Gly Tyr Pro Leu Ala Glu Val Ser Trp Pro Asn Val Ser Val
145                 150                 155                 160

Pro Ala Asn Thr Ser His Ser Arg Thr Pro Glu Gly Leu Tyr Gln Val
                165                 170                 175

Thr Ser Val Leu Arg Leu Lys Pro Pro Pro Gly Arg Asn Phe Ser Cys
            180                 185                 190

Val Phe Trp Asn Thr His Val Arg Glu Leu Thr Leu Ala Ser Ile Asp
        195                 200                 205

Leu Gln Ser Gln Met Glu Pro Arg Thr His Pro Thr Trp Leu Leu His
    210                 215                 220

Ile Phe Ile Pro Phe Cys Ile Ile Ala Phe Ile Phe Ile Ala Thr Val
225                 230                 235                 240

Ile Ala Leu Arg Lys Gln Leu Cys Gln Lys Leu Tyr Ser Ser Lys Asp
                245                 250                 255

Thr Thr Lys Arg Pro Val Thr Thr Thr Lys Arg Glu Val Asn Ser Ala

```
                    260                 265                 270

Ile

<210> SEQ ID NO 13
<211> LENGTH: 301
<212> TYPE: PRT
<213> ORGANISM: Homo sapiens

<400> SEQUENCE: 13

Met Phe Ser His Leu Pro Phe Asp Cys Val Leu Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
        35                  40                  45

Val Pro Val Cys Trp Gly Lys Gly Ala Cys Pro Val Phe Glu Cys Gly
    50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125

Ile Lys Pro Ala Lys Val Thr Pro Ala Pro Thr Arg Gln Arg Asp Phe
130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Ile Gly Ile Tyr Ile Gly Ala Gly
        195                 200                 205

Ile Cys Ala Gly Leu Ala Leu Ala Leu Ile Phe Gly Ala Leu Ile Phe
    210                 215                 220

Lys Trp Tyr Ser His Ser Lys Glu Lys Ile Gln Asn Leu Ser Leu Ile
225                 230                 235                 240

Ser Leu Ala Asn Leu Pro Pro Ser Gly Leu Ala Asn Ala Val Ala Glu
                245                 250                 255

Gly Ile Arg Ser Glu Glu Asn Ile Tyr Thr Ile Glu Glu Asn Val Tyr
            260                 265                 270

Glu Val Glu Glu Pro Asn Glu Tyr Tyr Cys Tyr Val Ser Ser Arg Gln
        275                 280                 285

Gln Pro Ser Gln Pro Leu Gly Cys Arg Phe Ala Met Pro
    290                 295                 300

<210> SEQ ID NO 14
<211> LENGTH: 525
<212> TYPE: PRT
<213> ORGANISM: Homo sapiens

<400> SEQUENCE: 14

Met Trp Glu Ala Gln Phe Leu Gly Leu Leu Phe Leu Gln Pro Leu Trp
1               5                   10                  15
```

-continued

```
Val Ala Pro Val Lys Pro Leu Gln Pro Gly Ala Glu Val Pro Val Val
            20                  25                  30

Trp Ala Gln Glu Gly Ala Pro Ala Gln Leu Pro Cys Ser Pro Thr Ile
        35                  40                  45

Pro Leu Gln Asp Leu Ser Leu Leu Arg Arg Ala Gly Val Thr Trp Gln
50                  55                  60

His Gln Pro Asp Ser Gly Pro Pro Ala Ala Pro Gly His Pro Leu
65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
            100                 105                 110

Arg Leu Pro Leu Gln Pro Arg Val Gln Leu Asp Glu Arg Gly Arg Gln
        115                 120                 125

Arg Gly Asp Phe Ser Leu Trp Leu Arg Pro Ala Arg Arg Ala Asp Ala
130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
        195                 200                 205

Gly Arg Val Pro Val Arg Glu Ser Pro His His Leu Ala Glu Ser
210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
            260                 265                 270

Gly Ala Gly Ser Arg Val Gly Leu Pro Cys Arg Leu Pro Ala Gly Val
        275                 280                 285

Gly Thr Arg Ser Phe Leu Thr Ala Lys Trp Thr Pro Pro Gly Gly Gly
290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
        355                 360                 365

Cys Glu Val Thr Pro Val Ser Gly Gln Glu Arg Phe Val Trp Ser Ser
370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
                405                 410                 415

Gly Glu Arg Leu Leu Gly Ala Ala Val Tyr Phe Thr Glu Leu Ser Ser
            420                 425                 430
```

```
Pro Gly Ala Gln Arg Ser Gly Arg Ala Pro Gly Ala Leu Pro Ala Gly
            435                 440                 445

His Leu Leu Leu Phe Leu Ile Leu Gly Val Leu Ser Leu Leu Leu Leu
    450                 455                 460

Val Thr Gly Ala Phe Gly Phe His Leu Trp Arg Arg Gln Trp Arg Pro
465                 470                 475                 480

Arg Arg Phe Ser Ala Leu Glu Gln Gly Ile His Pro Pro Gln Ala Gln
                485                 490                 495

Ser Lys Ile Glu Glu Leu Glu Gln Glu Pro Glu Pro Glu Pro Glu Pro
                500                 505                 510

Glu Pro Glu Pro Glu Pro Glu Pro Glu Gln Leu
            515                 520                 525

<210> SEQ ID NO 15
<211> LENGTH: 403
<212> TYPE: PRT
<213> ORGANISM: Homo sapiens

<400> SEQUENCE: 15

Met Ala His Ala Met Glu Asn Ser Trp Thr Ile Ser Lys Glu Tyr His
1               5                   10                  15

Ile Asp Glu Glu Val Gly Phe Ala Leu Pro Asn Pro Gln Glu Asn Leu
            20                  25                  30

Pro Asp Phe Tyr Asn Asp Trp Met Phe Ile Ala Lys His Leu Pro Asp
        35                  40                  45

Leu Ile Glu Ser Gly Gln Leu Arg Glu Arg Val Glu Lys Leu Asn Met
    50                  55                  60

Leu Ser Ile Asp His Leu Thr Asp His Lys Ser Gln Arg Leu Ala Arg
65                  70                  75                  80

Leu Val Leu Gly Cys Ile Thr Met Ala Tyr Val Trp Gly Lys Gly His
                85                  90                  95

Gly Asp Val Arg Lys Val Leu Pro Arg Asn Ile Ala Val Pro Tyr Cys
            100                 105                 110

Gln Leu Ser Lys Lys Leu Glu Leu Pro Pro Ile Leu Val Tyr Ala Asp
        115                 120                 125

Cys Val Leu Ala Asn Trp Lys Lys Lys Asp Pro Asn Lys Pro Leu Thr
130                 135                 140

Tyr Glu Asn Met Asp Val Leu Phe Ser Phe Arg Asp Gly Asp Cys Ser
145                 150                 155                 160

Lys Gly Phe Phe Leu Val Ser Leu Leu Val Glu Ile Ala Ala Ala Ser
                165                 170                 175

Ala Ile Lys Val Ile Pro Thr Val Phe Lys Ala Met Gln Met Gln Glu
            180                 185                 190

Arg Asp Thr Leu Leu Lys Ala Leu Leu Glu Ile Ala Ser Cys Leu Glu
        195                 200                 205

Lys Ala Leu Gln Val Phe His Gln Ile His Asp His Val Asn Pro Lys
    210                 215                 220

Ala Phe Phe Ser Val Leu Arg Ile Tyr Leu Ser Gly Trp Lys Gly Asn
225                 230                 235                 240

Pro Gln Leu Ser Asp Gly Leu Val Tyr Glu Gly Phe Trp Glu Asp Pro
                245                 250                 255

Lys Glu Phe Ala Gly Gly Ser Ala Gly Gln Ser Ser Val Phe Gln Cys
            260                 265                 270

Phe Asp Val Leu Leu Gly Ile Gln Gln Thr Ala Gly Gly Gly His Ala
        275                 280                 285
```

```
Ala Gln Phe Leu Gln Asp Met Arg Arg Tyr Met Pro Pro Ala His Arg
    290             295                 300
Asn Phe Leu Cys Ser Leu Glu Ser Asn Pro Ser Val Arg Glu Phe Val
305             310                 315                 320
Leu Ser Lys Gly Asp Ala Gly Leu Arg Glu Ala Tyr Asp Ala Cys Val
                325                 330                 335
Lys Ala Leu Val Ser Leu Arg Ser Tyr His Leu Gln Ile Val Thr Lys
            340                 345                 350
Tyr Ile Leu Ile Pro Ala Ser Gln Gln Pro Lys Glu Asn Lys Thr Ser
        355                 360                 365
Glu Asp Pro Ser Lys Leu Glu Ala Lys Gly Thr Gly Gly Thr Asp Leu
    370                 375                 380
Met Asn Phe Leu Lys Thr Val Arg Ser Thr Thr Glu Lys Ser Leu Leu
385             390                 395                 400
Lys Glu Gly
```

METHODS AND SYSTEMS FOR EVALUATION OF IMMUNE CELL INFILTRATE IN TUMOR SAMPLES

CROSS-REFERENCE TO RELATED APPLICATIONS

This application is a Continuation of U.S. Ser. No. 16/752,494, filed Jan. 20, 2020, which is a continuation of PCT/EP2018/069896, filed Jul. 23, 2018, which claims the benefit of U.S. 62/536,373, filed Jul. 24, 2017, and U.S. 62/675,707, filed May 23, 2018, the content of each of which is incorporated by reference in its entirety.

SEQUENCE LISTING INCORPORATION BY REFERENCE

A Sequence Listing has been submitted electronically in ASCII format, which is hereby incorporated by reference in its entirety. Said ACSII copy, created on Apr. 18, 2022, is named P34353US3_SeqList_ST25 and is 38,596 bytes in size.

BACKGROUND OF THE INVENTION

Field of the Invention

The invention relates to detection, characterization and enumeration of discrete populations of immune cells in tumor samples for use in prognosing and treating proliferative diseases, such as cancers.

Description of Related Art

The presence or absence of an inflammatory response is known to be a prognostic factor in a number of different cancer types, including colorectal cancer, melanoma, breast cancer, ovarian cancer, non-Hodgkin's lymphoma, head and neck cancer, non-small-cell lung cancer (NSCLC), esophageal cancer, and urothelial carcinoma, among others. See Pagès et al. (2010). In colorectal cancer, for example, the relative amount of immune cell infiltrate has been considered an independent prognostic factor for colorectal cancers since at least 1986. See Jass (1986). In the following 30 years, many groups have evaluated analytical and statistical methods for understanding the interaction between tumor prognosis and its immune context. See Mei et al. (2014) (conducting a meta-analysis of numerous prior studies in colorectal cancers).

In colorectal tumors, three methods of scoring the immune context have predominated: (1) the Jass score, in which the tumor is graded according to whether there is extensive or little/absent peri-tumoral lymphocyte infiltrate (see Jass (1987)); (2) Klintrup-Mäkinen grade, in which overall inflammatory cell reaction is scored in hematoxylin and eosin (H&E)-stained slides at the invasive margin (IM) on either a 3-point scale (0=no increase of inflammatory cells at IM; 1=mild and patchy increase of inflammatory cells at IM without destruction of invading cancer cell islets; 2=a band-like infiltrate at the IM with some destruction of cancer cell islets; and 3=very prominent inflammatory reaction, forming a cup-like zone at the invasive margin, and destruction of cancer cell islets); or a 2-point scale (low grade inflammation (scores 0-1 as described above) or high grade inflammation (scores 2-3 as described above), see Galon et al. (2014); and (3) Galon IMMUNOSCORE, in which slides are immunohistochemically stained for at least two lymphocyte populations (CD3/CD45RO, CD3/CD8 or CD8/CD45RO), and cell densities are separately scored in the tumor core (TC) and IM on a 2 point scale (0=low; 1=high), which scores are then integrated into a composite score from 0 (e.g., CD3 TC low, CD3 IM low, CD8 TC low, CD8 IM low) to 4 (e.g., CD3 TC high, CD3 IM high, CD8 TC high, CD8 IM high) (see Galon et al (2014); Galon (2016a); Galon (2016b); U.S. Pat. No. 8,481,271).

These approaches are not quantitative, but instead use binary scoring systems based on gross observations of relative quantities.

Some attempts have been made to automate such scoring of the immune context.

For example, the Galon IMMUNOSCORE from HalioDx is implemented on an automated digital pathology platform from Definiens. TC and IM regions are separately annotated in an H&E image, which is registered to images of serial sections immunohistochemically stained for CD3 and CD8. The software overlays a 0.8 mm tile in each region, calculates a cell density for each tile within the region, and then reports the density for the entire region as a mean of the three most infiltrated tiles of the region. See Anitei et al. (2014). "High" and "low" scores are determined by defining a cutpoint in mean cell density using a minimum P value approach. Id.

U.S. Pat. No. 9,298,968 describes a cell analysis system that: (1) digitizes stained tissue sections; (2) extracts cell features; (3) stratifies the tissue into separate compartments containing tumor cells or other relevant cell types based on the extracted features; (4) detects and characterizes cells within compartments of interest that stain above a defined threshold level for an inflammatory cell type marker; (5) derives an immune system state score for the tissue section based on the values or statistics of inflammatory cell type markers; and (6) uses the score to stratify patients. Although the '968 patent contemplates the necessity of a cutoff definition and scoring system, it does not appear to provide a concrete methodology for defining such a cutoff or implementing a scoring system. Rather, common approaches such as delineating between "positive" and "negative" regions and applying qualitative histological scoring grades based on intensity (such as 0, 1+, 2+, and 3+) are mentioned without explication for how such scoring systems could be integrated into a useful prognostic score. Therefore, the '968 patent only describes, at an aspirational level, a system that might be useful for automating analysis, but does not describe any specific prognostic analyses.

Forrest et al. (2014) propose an automated method of calculating a Klintrup-Mäkinen grade using the SLIDEPATH Tissue Image Analysis Version 2.0 software from Leica Biosystems. The invasive margin is annotated in H&E sections and immune cell densities (expressed as nuclei/$mm^2$) are automatically detected in the annotated regions on the basis of staining intensities, cell size and size of nuclei. Three serial sections for each tumor are tested and the cell density is expressed as the mean of the three sections. The mean cell densities are then assigned a grade of 0, 1, 2, or 3 based on the quartile in which the mean density falls, or in a category of "weak" (Grades 0 and 1) or "strong" (grades 2 and 3).

Each of the foregoing methods, whether automated or manual, relies on a binary scoring system in which a wide variety of potential cell counts are binned together and considered to be effectively the same. While such an approach can make manual analysis and score computation relatively easy, it does so at the expense of the accuracy of the prognosis. Thus, each method could result in misprognosis and/or missed opportunity for selection of an effective treatment for many patients.

BRIEF SUMMARY OF THE INVENTION

This disclosure relates generally to the quantitative assessment of immune cells in tumor samples including, for example, T-lymphocytes (immune cells positive for the CD3 biomarker), using a continuous scoring function to calculate an immune context score (ICS) for the tumor sample. Using a continuous scoring function instead of a binned approach improves the prognostic and predictive accuracy.

In an embodiment, a method is provided comprising: (a) annotating a region of interest (ROI) on a digital image of a tumor tissue section; (b) calculating a feature vector including a feature metric comprising a quantitative measure of one or more types of immune cells in the ROI; (c) applying a continuous scoring function to the feature vector to calculate an immune context score for the tumor tissue section. In an embodiment, one or more types of immune cells are detected morphologically (such as in an image of a sample stained with hematoxylin and eosin) and/or on the basis of cells expression of one or more immune cell markers. In an embodiment, the continuous scoring function is a non-linear time-to-event function, such as a function derived from a Cox proportional hazard model. In an exemplary embodiment the "time to event" is selected from the group consisting of recurrence free survival, progression free survival, and overall survival.

In another embodiment, a computer-implemented method is provided comprising causing a computer processor to execute a set of computer-executable functions stored on a memory, the set of computer-executable functions comprising: (A) obtaining a digital image of a tumor section, wherein the tumor section is histochemically stained for at least one human immune cell marker; (B) annotating one or more regions of interest (ROI) in the digital image; and (C) applying a scoring function to the ROI, wherein the scoring function comprises: (C1) calculating a feature vector for the ROI, the feature vector comprising one or more feature metrics for the human immune cell marker; and (C2) applying a continuous scoring function to the feature vector to obtain an immune context score for the tumor tissue section.

The one or more immune cell markers includes at least CD3 or total lymphocytes as detected by hematoxylin & eosin staining. In some embodiments, at least one additional T-lymphocyte-specific marker may also be included, such as CD8 (marker for cytotoxic T-lymphocytes), CD4 (marker for helper T-lymphocytes), FoxP3 (marker for regulatory T-lymphocytes), CD45RA (marker for naïve T-lymphocytes), and CD45RO (marker for memory T-lymphocytes). In one specific embodiment, at least two markers including human CD3 (or total lymphocytes as detected by H&E staining) and human CD8 are used, in which case a single section of the tumor tissue may be labeled with both markers, or serial sections may be used. In other cases, at least one of the immune cell biomarkers is lymphocytes identified in a hematoxylin & eosin stained section.

In an embodiment, the ROI includes at least a portion of a tumor core (TC) region or an invasive margin (IM) or peri-tumoral (PT) region. In some embodiments, multiple ROIs are used, with at least one ROI including a portion of a TC region and a separate ROI including a portion of an IM or PT region. In yet other embodiments, an ROI is selected that encompasses a portion of both the TC and IM or PT regions. In still other embodiments, a single ROI encompassing a portion of both the TC and IM or PT regions is used.

In some embodiments, at least one feature metric is derived from a quantity of cells expressing the human immune cell marker or a total area of the ROI expressing the human immune cell marker. In other embodiments, the feature metric is selected from the group consisting of:

- an area density of cells expressing the human immune cell marker within the ROI (number of positive cells over area of ROI),
- an area expression level density of human immune cell marker expression (area of human immune cell marker expression over area of ROI),
- a linear density of cells expressing the human immune cell marker (total number of cells expressing the human immune cell marker within a threshold distance from an edge of the ROI over the linear length of the edge, such as the linear length of the leading edge of the invasive margin),
- a ratio between the number of cells expressing the human immune cell marker and the total number of cells in the ROI,
- a ratio between the number of cells expressing the human immune cell marker and the total number of tumor cells in the ROI,
- a ratio between the number of cells expressing the human immune cell marker and the total number of immune cells in the ROI,
- an area percentage of the total ROI having a density of cells expressing the human immune cell marker above a predetermined threshold (i.e. area of ROI having cell density above a threshold value over total area of the ROI), or
- a linear percentage of an edge of the ROI in proximity to a mass of cells expressing the human immune cell marker at a density above a predetermined threshold (i.e., total number of pixels along the ROI edge (such as the leading edge of the invasive margin) with a predetermined number of pixels of a center having a minimum number of positive cells at a minimal density over the total number of pixels constituting the edge).

In some embodiments, the feature metric is a total metric. In other embodiments, the feature metric is a mean or median of the feature metric for a plurality of control regions of the ROI.

In some embodiments, the continuous scoring function is applied to one or more normalized feature metrics, the normalized feature metrics obtained by applying a normalization factor to the feature metric, the normalization factor being equal to a pre-determined upper limit or lower limit of the feature metric. In an embodiment, the normalization factor is obtained by evaluating a distribution of the feature metric values across a representative population of samples, identifying a skew in the distribution of feature metric values, and identifying a value at which a pre-determined number of samples fall beyond, wherein the value is selected as the normalization factor.

In another specific embodiment, a method is provided comprising: (a) annotating a one or more region(s) of interest (ROI) on a digital image of a tumor tissue section, wherein at least one of the ROIs includes at least a portion of an invasive margin region; (b) detecting and quantitating cells expressing human CD3 in the ROI or detecting and quantitating total lymphocytes in the ROI; (c) detecting and quantitating cells expressing human CD8 in the ROI; (d) calculating a density of CD3+ cells within the ROI or a density of total lymphocytes in the ROI, and optionally normalizing the CD3+ cell density or lymphocyte cell density; (e) calculating a density of CD8+ cells within the ROI and optionally normalizing the CD8+ cell density; (f) computing a feature vector including the CD8+ cell density and either or both of the CD3+ cell density and the total lymphocyte cell density, and applying a continuous scoring function to the feature vector to obtain an immune context score (ICS) for the tumor. In an embodiment, the at least one ROI including a portion of an IM region is an IM ROI or a peri-tumoral (PT) ROI. In an embodiment, the densities are area cell densities or linear cell densities. In an embodiment, the continuous scoring function is of the general form of formula 2:

$$ICS_{cox} = \exp(-b_1 * CD3_D - b_2 * CD8_D + b_3 * CD3_D * CD8_D) \quad \text{Formula 2}$$

wherein:
$CD3_D$ is a density of $CD3^+$ cells of the ROI or a density of total lymphocytes of the ROI,
$CD8_D$ is a density of $CD8^+$ cells of the ROI, and
$b_1$, $b_2$, and $b_3$ are constants obtained from applying a Cox proportional hazard model to a dataset comprising survival data, CD3+ or total lymphocyte cell density data, and CD8+ cell density data for each individual of a cohort of patients having the cancer type of the tumor tissue section.

In another embodiment, the continuous scoring function is of the general form of formula 2, wherein $|b_1|>|b_2|>|b_3|$. In another embodiment, the continuous scoring function is of the general form of formula 2, wherein the $CD3_D$ and $CD8_D$ cell densities are normalized cell densities, and $|b_1|>|b_2|>|b_3|$. In another embodiment, the continuous scoring function is a function according to Formula 2, wherein $CD3_D$ and $CD8_D$ are normalized area cell densities and wherein $|b_1|>|b_2|>|b_3|$. In another embodiment, the tumor is a colorectal tumor. In another embodiment, the tumor is a stage II colorectal tumor.

Also provided herein are systems for scoring an immune context of a tumor tissue sample, the systems including at least a computer processor and a memory, wherein the memory stores a set computer executable instructions to be executed by the computer processor, the set of computer executable instructions including any of the processes and methods described herein. In some embodiments, the systems include automated slide stainers for histochemically labelling sections of the tumor tissue sample, and/or means for generating digital images of the histochemically stained sections, such as microscopes operably linked to digital cameras or scanner systems. In further embodiments, the systems may further include a laboratory information system (LIS) for tracking and/or controlling processes to be performed on the samples, sections, and digital images.

DETAILED DESCRIPTION OF THE INVENTION

I. Definitions

Figure 1:
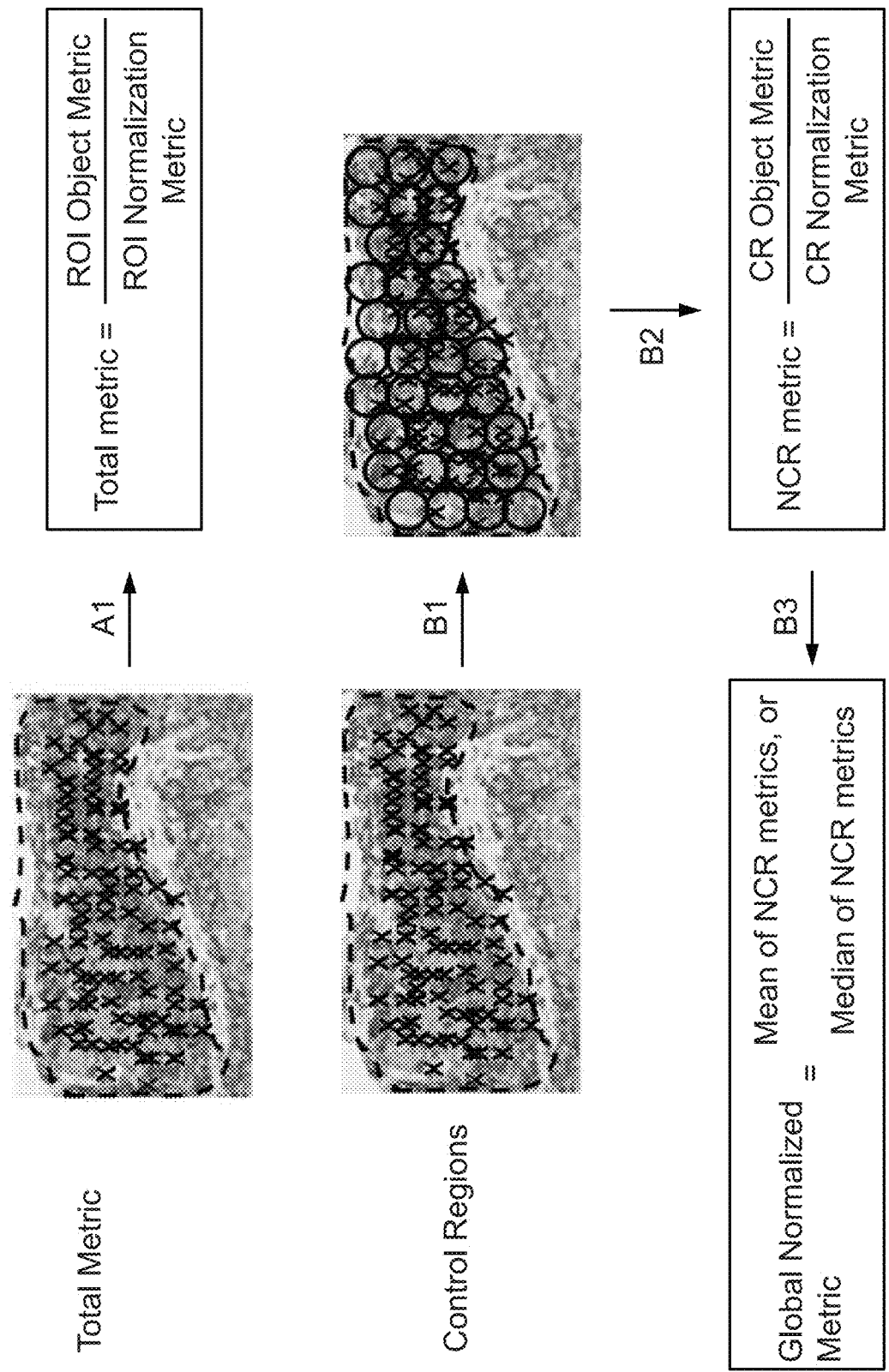
FIG. 1 illustrates two different methods of calculating feature metrics for ROIs. Dashed lines in the images illustrate the boundary of an ROI. "X"s in the image indicate objects of interest marked in the image. Circles in the image are control regions that may be used to calculate global metrics for the control region.

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier (4th ed. 2007); Sambrook et al., MOLECULAR CLONING, A LABORATORY MANUAL, Cold Springs Harbor Press (Cold Springs Harbor, N.Y. 1989). The term "a" or "an" is intended to mean "one or more." The terms "comprise," "comprises," and "comprising," when preceding the recitation of a step or an element, are intended to mean that the addition of further steps or elements is optional and not excluded.

Antibody: The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

Antibody fragment: An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

Biomarker: As used herein, the term "biomarker" shall refer to any molecule or group of molecules found in a biological sample that can be used to characterize the biological sample or a subject from which the biological sample is obtained. For example, a biomarker may be a molecule or group of molecules whose presence, absence, or relative abundance is:
- characteristic of a particular cell or tissue type or state;
- characteristic of a particular pathological condition or state; or
- indicative of the severity of a pathological condition, the likelihood of progression or regression of the pathological condition, and/or the likelihood that the pathological condition will respond to a particular treatment.

As another example, the biomarker may be a cell type or a microorganism (such as a bacteria, mycobacteria, fungi, viruses, and the like), or a substituent molecule or group of molecules thereof.

Biomarker-specific reagent: A specific detection reagent that is capable of specifically binding directly to one or more biomarkers in the cellular sample, such as a primary antibody.

Cellular sample: As used herein, the term "cellular sample" refers to any sample containing intact cells, such as cell cultures, bodily fluid samples or surgical specimens taken for pathological, histological, or cytological interpretation.

Continuous scoring function: A "continuous scoring function" is a mathematical formula into which the actual magnitude for one or more variables is input (optionally subject to upper and/or lower limits on the value and/or application of a normalization factor). In some examples, the value input into the continuous scoring function is the actual magnitude of the variable. In other examples, the value input into the continuous scoring function is the absolute value of the variable up to (and/or down to, as appropriate) a predetermined cutoff, wherein all absolute values beyond the cutoff value are assigned the cutoff value. In other examples, the value input into the continuous scoring function is a normalized value of the variable. By way of contrast, in a "non-continuous scoring function" (also referred to herein as a "binary scoring function"), each variable is assigned to a pre-determined "bin" (for example, "high," "medium," or "low"), and the same value is input into the mathematical function for all members of the same bin. For example, assume that the variable being assessed is a density of CD8+ T-cells. In a continuous scoring function, the value input into the function is the density of CD8+ T-cells (optionally subject to certain upper- and/or lower-limits and/or normalization). In a non-continuous or binary scoring function, the density value is first analyzed to determine whether it falls into a "high density" or a "low density" bin, and the value that is input into the non-continuous scoring function is whatever arbitrary value is assigned to members of that bin (for example, 0 for low, 1 for high). Thus, consider two samples, a first having a density of 500 CD8+ cells/mm$^2$ and a second having a density of 700 CD8+ cells/mm$^2$. The values input into a continuous scoring function would be 500 and 700, respectively (or modified based upon maximum or minimum cutoff values and/or normalization factor (s)). The values input into a non-continuous scoring function would depend on the bin in which they fall. If the "high bin" encompasses both 500 and 700 cells/mm$^2$, then a value of 1 would be input into the non-continuous scoring function for each sample. If the cutoff between "high" and "low" bins fell somewhere between 500 and 700 cells/mm$^2$, then a value of 0 would be input into a non-continuous scoring function for the first sample, and a value of 1 would be input into a non-continuous scoring function for the second sample. If the "low bin" encompasses both 500 and 700 cells/mm$^2$, then a value of 0 would be input into the non-continuous scoring function for each sample. Please note that these values are intended to illustrate the difference between a continuous scoring function and a non-continuous scoring function, and should not be construed as in any way limiting the scope of the disclosure unless recited in a claim.

Cox proportional hazard model: A model of formula 1:

$$\frac{h(t)}{h_0(t)} = \exp(b_1 X_1 + b_2 X_2 + \ldots b_p X_p) \quad \text{Formula 1}$$

wherein $$\frac{h(t)}{h_0(t)}$$

is the ratio between the expected hazard at time t (h(t)) and a baseline hazard ($h_0(t)$), and $b_1$, $b_2$ . . . $b_p$ are constants extrapolated for each of the independent variables. As used throughout, the ratio $$\text{``}\frac{h(t)}{h_0(t)}\text{''}$$

will be referred to as the "Cox immune context score" or "$ICS_{cox}$." A reference to "Cox model" in this specification shall mean "Cox proportional hazard model."

Detection reagent: A "detection reagent" is any reagent that is used to deposit a stain in proximity to a biomarker-specific reagent in a cellular sample. Non-limiting examples include biomarker-specific reagents (such as primary antibodies), secondary detection reagents (such as secondary antibodies capable of binding to a primary antibody), tertiary detection reagents (such as tertiary antibodies capable of binding to secondary antibodies), enzymes directly or indirectly associated with the biomarker specific reagent, chemicals reactive with such enzymes to effect deposition of a fluorescent or chromogenic stain, wash reagents used between staining steps, and the like.

Detectable moiety: A molecule or material that can produce a detectable signal (such as visually, electronically or otherwise) that indicates the presence (i.e. qualitative analysis) and/or concentration (i.e. quantitative analysis) of the detectable moiety deposited on a sample. A detectable signal can be generated by any known or yet to be discovered mechanism including absorption, emission and/or scattering of a photon (including radio frequency, microwave frequency, infrared frequency, visible frequency and ultraviolet frequency photons). The term "detectable moiety" includes chromogenic, fluorescent, phosphorescent, and luminescent molecules and materials, catalysts (such as enzymes) that convert one substance into another substance to provide a detectable difference (such as by converting a colorless substance into a colored substance or vice versa, or by producing a precipitate or increasing sample turbidity). In some examples, the detectable moiety is a fluorophore, which belongs to several common chemical classes including coumarins, fluoresceins (or fluorescein derivatives and analogs), rhodamines, resorufins, luminophores and cyanines. Additional examples of fluorescent molecules can be found in Molecular Probes Handbook—A Guide to Fluorescent Probes and Labeling Technologies, Molecular Probes, Eugene, Oreg., ThermoFisher Scientific, 11$^{th}$ Edition. In other embodiments, the detectable moiety is a molecule detectable via brightfield microscopy, such as dyes including diaminobenzidine (DAB), 4-(dimethylamino) azobenzene-4'-sulfonamide (DABSYL), tetramethylrhodamine (DISCOVERY Purple), N,N'-biscarboxypentyl-5,5'-disulfonato-indo-dicarbocyanine (Cy5), and Rhodamine 110 (Rhodamine).

Extra-tumoral region: A contiguous region of tissue not located in a tumor region.

Feature metric: A value indicative of an expression level of a biomarker in a sample. Examples include: expression intensity (for example, on a 0+, 1+, 2+, 3+ scale), number of cells positive for the biomarker, cell density (for example, number of biomarker-positive cells over an area of an ROI, number of biomarker-positive cells over a linear distance of an edge defining an ROI, and the like), pixel density (i.e. number of biomarker-positive pixels over an area of an ROI, number of biomarker-positive pixels over a linear distance of an edge defining an ROI, and the like), etc. A feature metric can be a total metric or a global metric.

Histochemical detection: A process involving labelling biomarkers or other structures in a tissue sample with biomarker-specific reagents and detection reagents in a manner that permits microscopic detection of the biomarker or other structures in the context of the cross-sectional relationship between the structures of the tissue sample. Examples include immunohistochemistry (IHC), chromogenic in situ hybridization (CISH), fluorescent in situ hybridization (FISH), silver in situ hybridization (SISH), and hematoxylin and eosin (H&E) staining of formalin-fixed, paraffin-embedded tissue sections.

Immune checkpoint molecule: A protein expressed by an immune cell whose activation down-regulates a cytotoxic T-cell response. Examples include PD-1, TIM-3, LAG-3, and CTLA-4.

Immune escape biomarker: A biomarker expressed by a tumor cell that helps the tumor avoid a T-cell mediated immune response. Examples of immune escape biomarkers include PD-L1, PD-L2, and IDO.

Immunological biomarker: A biomarker that is characteristic of or impacts upon an immune response to an abnormal cell, including but not limited to biomarkers that: are indicative of a particular class of immune cell (such as a CD3), characterize an immune response (such as the presence, absence, or amount of cytokine proteins or particular immune cell subtype(s)), or that are expressed by, presented by, or otherwise located on non-immune cell structure that affect the type or extent of responses of immune cell (such as cell surface expressed antigens, MHC-ligand complexes, and immune escape biomarkers).

Intra-tumoral region: Tissue located inside of a tumor region.

Invasive margin (IM): The interface between invasive neoplastic tissue and normal tissue. When used in the context of an ROI, "IM" refers to an ROI restricted to a region of a tumor identified by an expert reader as encompassing an invasive margin.

Monoclonal antibody: An antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, or a combination thereof.

Multiplex histochemical stain: A histochemical staining method in which multiple biomarker-specific reagents that bind to different biomarkers are applied to a single section and stained with different color stains.

Non-linear continuous scoring function: A continuous scoring function having the general structure of anything other than $f(x)=a+bx$, wherein x is a variable and a and b are constants. Thus, for example, "non-linear continuous scoring function" includes non-linear algebraic functions (such as non-constant, non-linear polynomial functions; rational functions; and nth root functions) and transcendental functions (such as exponential functions, hyperbolic functions, logarithmic functions, and power functions).

Normalize: To adjust a feature metric by a fixed factor so that different feature metrics are expressed on the same scale.

Normalization factor: A fixed factor applied to a feature metric to obtain a normalized feature metric.

Normalized feature metric: A feature metric, the value of which has been adjusted by a normalization factor.

Peri-tumoral (PT) region: The region of a tumor in the immediate vicinity of the invasive margin, which may also include a portion of the extra-tumoral tissue and a portion of the tumor core.

Peri-tumoral (PT) ROI: An ROI including at least a portion of the IM region, and optionally extra-tumoral tissue in the immediate vicinity of the IM region and/or a portion of the tumor core region in the immediate vicinity of the IM. For example, "PT ROI" may encompass all pixels within a defined distance of any point on the interface between tumor cells and non-tumor cells, or it may encompass an ROI of a defined width centered on the interface between tumor cells and non-tumor cells, or it may encompass an plurality of defined shapes each centered at a point on the interface between tumor cells and non-tumor cells (such as a plurality of overlapping circles, each centered at a discrete point on the interface between tumor cells and non-tumor cells).

Sample: As used herein, the term "sample" shall refer to any material obtained from a subject capable of being tested for the presence or absence of a biomarker.

Secondary detection reagent: A specific detection reagent capable of specifically binding to a biomarker-specific reagent.

Section: When used as a noun, a thin slice of a tissue sample suitable for microscopic analysis, typically cut using a microtome. When used as a verb, the process of generating a section.

Serial section: As used herein, the term "serial section" shall refer to any one of a series of sections cut in sequence by a microtome from a tissue sample. For two sections to be considered "serial sections" of one another, they do not necessarily need to be consecutive sections from the tissue, but they should generally contain sufficiently similar tissue structures in the same spatial relationship, such that the structures can be matched to one another after histological staining.

Simplex histochemical stain: A histochemical staining method in which a single biomarker-specific reagent is applied to a single section and stained with a single color stain.

Specific detection reagent: Any composition of matter that is capable of specifically binding to a target chemical structure in the context of a cellular sample. As used herein, the phrase "specific binding," "specifically binds to," or "specific for" or other similar iterations refers to measurable and reproducible interactions between a target and a specific detection reagent, which is determinative of the presence of the target in the presence of a heterogeneous population of molecules including biological molecules. For example, an antibody that specifically binds to a target is an antibody that binds this target with greater affinity, avidity, more readily, and/or with greater duration than it binds to other targets. In one embodiment, the extent of binding of a specific detection reagent to an unrelated target is less than about 10% of the binding of the antibody to the target as measured, e.g., by a radioimmunoassay (RIA). In certain embodiments, a biomarker-specific reagent that specifically binds to a target has a dissociation constant (Kd) of $\leq 1$ µM, $\leq 100$ nM, $\leq 10$ nM, $\leq 1$ nM, or $\leq 0.1$ nM. In another embodiment, specific binding can include, but does not require exclusive binding. Exemplary specific detection reagents include nucleic acid probes specific for particular nucleotide sequences; antibodies and antigen binding fragments thereof; and engineered specific binding compositions, including ADNECTINs (scaffold based on 10th FN3 fibronectin; Bristol-Myers-Squibb Co.), AFFIBODYs (scaffold based on Z domain of protein A from *S. aureus*; Affibody AB, Solna, Sweden), AVIMERs (scaffold based on domain A/LDL receptor; Amgen, Thousand Oaks, Calif.), dAbs (scaffold based on VH or VL antibody domain; GlaxoSmithKline PLC, Cambridge, UK), DARPins (scaffold based on Ankyrin repeat proteins; Molecular Partners AG, Zürich, CH), ANTI-CALINs (scaffold based on lipocalins; Pieris AG, Freising, DE), NANOBODYs (scaffold based on VHH (camelid Ig); Ablynx N/V, Ghent, BE), TRANS-BODYs (scaffold based on Transferrin; Pfizer Inc., New York, N.Y.), SMIPs (Emergent Biosolutions, Inc., Rockville, Md.), and TETRANEC-TINs (scaffold based on C-type lectin domain (CTLD), tetranectin; Borean Pharma A/S, Aarhus, DK). Descriptions of such engineered specific binding structures are reviewed by Wurch et al., *Development of Novel Protein Scaffolds as Alternatives to Whole Antibodies for Imaging and Therapy: Status on Discovery Research and Clinical Validation*, Current Pharmaceutical Biotechnology, Vol. 9, pp. 502-509 (2008), the content of which is incorporated by reference.

Stain: When used as a noun, the term "stain" shall refer to any substance that can be used to visualize specific molecules or structures in a cellular sample for microscopic analysis, including brightfield microscopy, fluorescent microscopy, electron microscopy, and the like. When used as a verb, the term "stain" shall refer to any process that results in deposition of a stain on a cellular sample.

Subject: As used herein, the term "subject" or "individual" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

Test sample: A tumor sample obtained from a subject having an unknown outcome at the time the sample is obtained.

Time-to-event model: A mathematical model in which the variables are modeled against their ability to predict the likelihood that a defined event will occur by a time t.

Tissue sample: As used herein, the term "tissue sample" shall refer to a cellular sample that preserves the cross-sectional spatial relationship between the cells as they existed within the subject from which the sample was obtained.

Tumor core (TC): The region of an invasive neoplastic lesion that is not the invasive margin. In the context of an ROI, "TC" refers to a portion of a whole tumor region that is neither IM nor excluded from the ROI as an artifact.

Tumor sample: A tissue sample obtained from a tumor.

Whole tumor (WT) region: A portion of a tissue section characterized by one or more contiguous regions composed substantially entirely of invasive neoplastic cells, including both TC and IM regions.

Whole tumor ROI: An ROI limited to a whole tumor region.

II. Biomarker Descriptions

CD3: CD3 is a cell surface receptor complex that is frequently used as a defining biomarker for cells having a T-cell lineage. The CD3 complex is composed of 4 distinct polypeptide chains: CD3-gamma chain, CD3-delta chain, CD3epsilon chain, and CD3-zeta chain. CD3-gamma and CD3-delta each form heterodimers with CD3-epsilon (εγ-homodimer and εδ-heterodimer) while CD3-zeta forms a homodimer (ζζ-homodimer). Functionally, the cy-homodimer, εδ-heterodimer, and ζζ-homodimer form a signaling complex with T-cell receptor complexes. Exemplary sequences for (and isoforms and variants of) the human CD3-gamma chain, CD3-delta chain, CD3epsilon chain, and CD3-zeta chain can be found at Uniprot Accesion Nos. P09693 (the canonical amino acid sequence for which is disclosed herein at SEQ ID NO: 1), P04234 (the canonical amino acid sequence for which is disclosed herein at SEQ ID NO: 2), P07766 (the canonical amino acid sequence for which is disclosed herein at SEQ ID NO: 3), and P20963 (the canonical amino acid sequence for which is disclosed herein at SEQ ID NO: 4), respectively. As used herein, the term "human CD3 protein biomarker" encompasses any CD3-gamma chain, CD3-delta chain, CD3epsilon chain, and CD3-zeta chain polypeptide having a canonical human sequence and natural variants thereof that maintain the function of the canonical sequence; εγ-homodimers, εδ-heterodimers, and ζζ-homodimers including one or more of CD3-gamma chain, CD3-delta chain, CD3epsilon chain, and CD3-zeta chain polypeptide having a canonical human sequence and natural variants thereof that maintain the function of the canonical sequence; and any signaling complex including one or more of the foregoing CD3 homodimers or heterodimers. In some embodiments, a human CD3 protein biomarker-specific agent encompasses any biomarker-specific agent that specifically binds a structure (such as an epitope) within CD3-gamma chain polypeptide (such as the polypeptide at SEQ ID NO: 1), CD3-delta chain polypeptide (such as the polypeptide at SEQ ID NO: 2), CD3epsilon chain polypeptide (such as the polypeptide at SEQ ID NO: 3), or CD3-zeta chain polypeptide (such as the polypeptide at SEQ ID NO: 4), or that binds to a structure (such as an epitope) located within εγ-homodimer, εδ-heterodimer, or ζζ-homodimer.

CD4: CD4 is a member of the immunoglobulin superfamily, encoded by the CD4 gene on chromosome 12. CD4 is frequently used as a marker for helper T-cells. Exemplary sequences for (and isoforms and variants of) the human CD4 receptor can be found at Uniprot Accesion Nos. P01730 (the canonical amino acid sequence for which is disclosed herein at SEQ ID NO: 5). As used herein, the term "human CD4 protein biomarker" encompasses any CD4 polypeptide having a canonical human sequence and natural variants thereof that maintain the function of the canonical sequence. In some embodiments, a human CD4 protein biomarker-specific agent encompasses any biomarker-specific agent that specifically binds a structure (such as an epitope) within a human CD4 polypeptide (such as the polypeptide at SEQ ID NO: 5).

CD8: CD8 is a heterodimeric, disulphide linked, transmembrane glycoprotein found on the cytotoxic-suppressor T cell subset, on thymocytes, on certain natural killer cells, and in a subpopulation of bone marrow cells. Exemplary sequences for (and isoforms and variants of) the human alpha- and beta-chain of the CD8 receptor can be found at Uniprot Accesion Nos. P01732 (the canonical amino acid sequence for which is disclosed herein at SEQ ID NO: 6) and P10966 (the canonical amino acid sequence for which is disclosed herein at SEQ ID NO: 7), respectively. As used herein, the term "human CD8 protein biomarker" encompasses any CD8-alpha chain polypeptide having a canonical human sequence and natural variants thereof that maintain the function of the canonical sequence; any CD8-beta chain polypeptide having a canonical human sequence and natural variants thereof that maintain the function of the canonical sequence; any dimers including a CD8-alpha chain polypeptide having a canonical human sequence and natural variants thereof that maintain the function of the canonical sequence and/or a CD8-beta chain polypeptide having a canonical human sequence and natural variants thereof that maintain the function of the canonical sequence. In some embodiments, a human CD8 protein biomarker-specific agent encompasses any biomarker-specific agent that specifically binds a structure (such as an epitope) within CD8-alpha chain polypeptide (such as the polypeptide at SEQ ID NO: 6), CD8-beta chain polypeptide (such as the polypeptide at SEQ ID NO: 7), or that binds to a structure (such as an epitope) located within a CD8 dimer.

CD45: CD45 is a transmembrane glycoprotein expressed on most nucleated cells of haematopoietic origin. CD45, encoded by the PTPRC gene on chromosome 1, has various isoforms, based on differential splicing of exons 4, 5 and 6. On human leucocytes, five different isoforms of CD45, named ABC, AB, BC, B and 0, have been identified. These isoforms are recognized by CD45RA, CD45RB, CD45RC and CD45RO antibodies. CD45RA antibodies recognize the extracellular A domain in the two isoforms, ABC (Mr 220 000), and AB (Mr 200 000). All the CD45 isoforms share the same intracellular segment, which has been shown to have tyrosine phosphatase activity. Various leucocytes express characteristic CD45 isoforms, thus T cells express CD45 isoforms corresponding to their development and activation. B cells predominantly express the ABC isoform, and monocytes and dendritic cells predominantly express the B and 0 isoforms. Granulocytes principally express only the B and 0 isoforms (2). As used herein, a "CD45RA biomarker" is any protein recognized by a CD45RA antibody. As used herein, a "CD45RO biomarker" is any protein recognized by a CD45RO antibody.

CTLA-4: CTLA-4 (also known as CD152), is an immune checkpoint protein expressed by the CTLA4 gene on chromosome 2 of humans. Exemplary sequences for (and isoforms and variants of) the human CTLA-4 protein can be found at Uniprot Accesion No. P16410 (the canonical amino acid sequence for which is disclosed herein at SEQ ID NO: 8).

FoxP3: Forkhead box protein P3 (FoxP3) is a transcriptional regulator that is involved in the development and inhibitory function of regulatory T-cells ($T_{reg}$) that is encoded by the FOXP3 gene of the X chromosome. Exemplary sequences for (and isoforms and variants of) the human FOXP3 protein can be found at Uniprot Accesion No. Q9BZS1 (the canonical amino acid sequence for which is disclosed herein at SEQ ID NO: 9). In some embodiments, a human FoxP3 protein biomarker-specific agent encompasses any biomarker-specific agent that specifically binds a structure (such as an epitope) within a human FoxP3 polypeptide (such as the polypeptide at SEQ ID NO: 9).

PD-1: Programmed death-1 (PD-1) is a member of the CD28 family of receptors encoded by the PDCD1 gene on chromosome 2. Exemplary sequences for (and isoforms and variants of) the human PD-1 protein can be found at Uniprot Accesion No. Q15116 (the canonical amino acid sequence for which is disclosed herein at SEQ ID NO: 10). In some embodiments, a human PD-1 protein biomarker-specific agent encompasses any biomarker-specific agent that specifically binds a structure (such as an epitope) within a human PD-1 polypeptide (such as the polypeptide at SEQ ID NO: 10).

PD-L1: Programmed death ligand 1 (PD-L1) is a type 1 transmembrane protein encoded by the CD274 gene on chromosome 9. PD-L1 acts as a ligand for PD-1 and CD80. Exemplary sequences for (and isoforms and variants of) the human PD-L1 protein can be found at Uniprot Accesion No. Q9NZQ7 (the canonical amino acid sequence for which is disclosed herein at SEQ ID NO: 11). In some embodiments, a human PD-L1 protein biomarker-specific agent encompasses any biomarker-specific agent that specifically binds a structure (such as an epitope) within a human PD-L1 polypeptide (such as the polypeptide at SEQ ID NO: 11).

PD-L2: Programmed death ligand 2 (PD-L2) is a transmembrane protein encoded by the PDCD1LG2 gene on chromosome 9. PD-L2 acts as a ligand for PD-1. Exemplary sequences for (and isoforms and variants of) the human PD-L2 protein can be found at Uniprot Accesion No. Q9BQ51 (the canonical amino acid sequence for which is disclosed herein at SEQ ID NO: 12). In some embodiments, a human PD-L2 protein biomarker-specific agent encompasses any biomarker-specific agent that specifically binds a structure (such as an epitope) within a human PD-L2 polypeptide (such as the polypeptide at SEQ ID NO: 12).

TIM-3: T-cell immunoglobulin mucin receptor 3, also known as TIM-3, is an immune checkpoint protein encoded by the HAVCR2 gene located on human chromosome 5. Exemplary sequences for (and isoforms and variants of) the human TIM-3 protein can be found at Uniprot Accesion No. Q8TDQ0 (the canonical amino acid sequence for which is disclosed herein at SEQ ID NO: 13). In some embodiments, a human TIM-3 protein biomarker-specific agent encompasses any biomarker-specific agent that specifically binds a structure (such as an epitope) within a human TIM3 polypeptide (such as the polypeptide at SEQ ID NO: 13).

LAG3: Lymphocyte activation gene 3 protein (LAG3) is a member of the immunoglobulin (Ig) superfamily encoded by the LAG3 gene on human chromosome 12. Exemplary sequences for (and isoforms and variants of) the human LAG3 protein can be found at Uniprot Accesion No. P18627 (the canonical amino acid sequence for which is disclosed herein at SEQ ID NO: 14). In some embodiments, a human LAG3 protein biomarker-specific agent encompasses any biomarker-specific agent that specifically binds a structure (such as an epitope) within a human LAG3 polypeptide (such as the polypeptide at SEQ ID NO: 14).

IDO: Indoleamine 2,3-dioxygenase 1 (IDO) is an enzyme encoded by the IDO1 gene on human chromosome 8. Exemplary sequences for (and isoforms and variants of) the human IDO protein can be found at Uniprot Accesion No. P14902 (the canonical amino acid sequence for which is disclosed herein at SEQ ID NO: 15). In some embodiments, a human IDO protein biomarker-specific agent encompasses any biomarker-specific agent that specifically binds a structure (such as an epitope) within a human IDO1 polypeptide (such as the polypeptide at SEQ ID NO: 15).

III. Generation of the Continuous Scoring Function

Prior scoring methods (such as the Galon IMMUNOSCORE) rely on establishing pre-defined bins of expression levels for the selected immunological biomarkers (such as "high" and "low" bins or "high," "medium," and "low" bins). Any expression level that falls within the bin is assigned the exact same score, regardless of whether it is found at the highest end of the bin or the lowest end of the bin. In contrast, the present methods use a continuous scoring function, which we have found allows for better discrimination between risk groups.

The continuous scoring functions of the present methods and systems are generally derived from tumor samples from a cohort of patients with known outcomes and having the indication of interest. A panel of biomarkers to test is selected, the samples of the cohort are stained for the biomarkers, and feature metrics for the biomarkers are calculated from one or more ROIs (which feature metrics optionally may be normalized and/or subject to upper or lower limits). The feature metrics for the samples are modeled against the outcomes using a one or more of a variety of models, including "time-to-event" models (such as Cox proportional hazard models for overall survival, progression-free survival, or recurrence-free survival) and binary event models (such as logistic regression models). Once a candidate continuous scoring function is identified, one or more cutoffs optionally may be selected to separate the cohort into groups according to their ICS (for example "high risk" and "low risk" groups), for example by using ROC curves, and the cutoffs are tested using Kaplan-Meier curves comparing the groups. The candidate continuous scoring function and cutoff combination showing the desired separation between groups is then selected. This function may then be used in an immune scoring system and methods as described herein.

III.A. Samples and Sample Preparation for Generation of the Continuous Scoring Function The continuous scoring function is typically modeled on tissue sections obtained from a cohort of subjects having a tumor. In some embodiments, the tumor is a solid tumor, such as a carcinoma, lymphoma, or sarcoma. In an embodiment, the tumor is a tumor of the skin, breast, head and/or neck, lung, upper gastrointestinal tract (including the esophagus and stomach), female reproductive system (including uterine, fallopian, and ovarian tumors), lower gastrointestinal tract (including the colon, rectal, and anal tumors), urogenital tract, exocrine, endocrine, renal, neural, or of lymphocytic origin. In an embodiment, subject has a melanoma, breast cancer, ovarian cancer, pancreatic cancer, head and neck cancer, lung cancer, esophageal cancer, gastric cancer, colorectal cancer (including cancer of the colon, rectum, and anus), prostate, urothelial cancer, or lymphoma. In specific embodiments, the tumor is a melanoma, lung, bladder, breast, prostate, or colorectal cancer.

The samples are typically tissue samples processed in a manner compatible with histochemical staining, including, for example, fixation (such as with formalin), embedding in a wax matrix (such as paraffin), and sectioning (such as with a microtome). No specific processing step is required by the present disclosure, so long as the sample obtained is compatible with histochemical staining of the sample for the biomarkers of interest and generating a digital image of the stained sample. In a specific embodiment, the continuous scoring function is modeled using microtome sections of formalin-fixed, paraffin-embedded (FFPE) samples. Additionally, for generation of the continuous scoring function, the samples of the cohort should be samples with a known outcome, such as recurrence of disease, progression of disease, death from disease, or overall death. Where the continuous scoring function is modeled on a Cox proportional hazard function, the outcome is typically time to recurrence, time to progression, and/or time to death.

III.B. Biomarker Panels

When generating the continuous scoring function, a panel of immunological biomarkers is typically tested for their ability (either alone or in combination) to predict the tumor prognosis, risk of progression, and/or likelihood of responding to a particular treatment course. In the present embodiments, a panel typically includes biomarkers for identifying at least one immune cell type, including T-lymphocytes (such as cytotoxic T-lymphocytes, helper T-lymphocytes, and regulatory T-lymphocytes). In some embodiments, the immune cell type may be detected based upon the expression of a cell surface marker specific for that immune cell type. In another embodiment, the immune cell type may be detected morphologically in an H&E stained tissue section.

In some embodiments, the at least one immune cell is a lymphocyte detected morphologically. In such an embodiment, an ROI is identified in a histochemically stained section of the sample, and total lymphocytes are detected and quantitated in the ROI. An example of an automated method of detecting lymphocytes using deep neural networks is disclosed by Chen & Srinivas (2016).

In some embodiments, the at least one immune cell is a T-lymphocyte. In such a case, at least one section of the sample is labeled with a human CD3 protein biomarker-specific reagent in combination with appropriate detection reagents. In some cases, it may also be desirable to analyze subtypes of T-lymphocytes. For example, where cytotoxic T-lymphocytes are to be detected, at least one section of the sample is labeled with a human CD3 protein biomarker-specific reagent in combination with appropriate detection reagents (or is labeled with hematoxylin and eosin where total lymphocytes are to be identified morphologically), and at least one section of the sample is labeled with a human CD8 protein biomarker-specific reagent in combination with appropriate detection reagents. Where helper T-lymphocytes are to be detected, at least one section of the sample is labeled with a human CD3 protein biomarker-specific reagent in combination with appropriate detection reagents (or is labeled with hematoxylin and eosin where total lymphocytes are to be identified morphologically), and at least one section of the sample is labeled with a human CD4 protein biomarker-specific reagent in combination with appropriate detection reagents. Where regulatory T-lymphocytes are to be detected, at least one section of the sample is labeled with a human CD3 protein biomarker-specific reagent in combination with appropriate detection reagents (or is labeled with hematoxylin and eosin where total lymphocytes are to be identified morphologically), and at least one section of the sample is labeled with a human FoxP3 protein biomarker-specific reagent in combination with appropriate detection reagents. Where naïve T-lymphocytes are to be detected, at least one section of the sample is labeled with a human CD3 protein biomarker-specific reagent in combination with appropriate detection reagents (or is labeled with hematoxylin and eosin where total lymphocytes are to be identified morphologically), and at least one section of the sample is labeled with a human CD45RA protein biomarker-specific reagent in combination with appropriate detection reagents. Where memory T-lymphocytes are to be detected, at least one section of the sample is labeled with a human CD3 protein biomarker-specific reagent in combination with appropriate detection reagents (or is labeled with hematoxylin and eosin where total lymphocytes are to be identified morphologically), and at least one section of the sample is labeled with a human CD45RO protein biomarker-specific reagent in combination with appropriate detection reagents.

It may also be of interest to evaluate the samples for the presence of or level of expression of immune checkpoint molecules and/or immune escape molecules, which may indicate active down-regulation of the immune response by the tumor or associated immune cells. In such a case, at least one section of the sample is labeled with one or more of: a human PD-1 protein biomarker-specific reagent, a human TIM-3 protein biomarker-specific reagent, a human LAG-3 protein biomarker-specific reagent, a human CTLA-4 protein biomarker-specific reagent, a human PD-L1 protein biomarker-specific reagent, a human PD-L2 protein biomarker-specific reagent, and/or a human IDO protein biomarker-specific reagent, each in combination with appropriate detection reagents.

Non-limiting exemplary panels of biomarkers are set forth below in Table 1:

TABLE 1

| Panel | Biomarkers | Object correlated with each biomarker |
|---|---|---|
| 1 | CD3 | Total T-lymphocytes (CD3+) |
| 2 | CD3 | Total T-lymphocytes (CD3+) |
|   | CD8 | Cytotoxic T-Lymphocytes (CD8+) |
| 3 | CD3 | Total T-lymphocytes (CD3+) |
|   | FoxP3 | Regulatory T-lymphocytes (FoxP3+) |
| 4 | CD3 | Total T-lymphocytes (CD3+) |
|   | CD8 | Cytotoxic T-Lymphocytes (CD8+) |
|   | FoxP3 | Regulatory T-lymphocytes (FoxP3+) |

TABLE 1-continued

| Panel | Biomarkers | Object correlated with each biomarker |
|---|---|---|
| 5a | CD3 | Total T-lymphocytes (CD3+) |
| | PD-L1 | Total PD-L1 expression (expressed as area of ROI containing PD-L1 positive staining) |
| 5b | CD3 | Total T-lymphocytes (CD3+) |
| | PD-L1 | Total PD-L1 expression (expressed as total number of cells in ROI staining positive for PD-L1) |
| 5c | CD3 | Total T-lymphocytes (CD3+) |
| | PD-L1 | PD-L1+ tumor cells |
| | | PD-L1+ non-tumor cells |
| 5d | CD3 | Total T-lymphocytes (CD3+) |
| | PD-L1 | PD-L1+ immune cells |
| | | PD-L1+ non-immune cells |
| 5e | CD3 | Total T-lymphocytes (CD3+) |
| | PD-L1 | PD-L1+ tumor cells |
| | | PD-L1+ immune cells |
| 5f | CD3 | Total T-lymphocytes (CD3+) |
| | PD-L1 | PD-L1+ tumor cells |
| 5g | CD3 | Total T-lymphocytes (CD3+) |
| | PD-L1 | PD-L1+ immune cells |
| 5h | CD3 | Total T-lymphocytes (CD3+) |
| | PD-L1 | PD-L1+ membrane staining |
| 6a | CD3 | Total T-lymphocytes (CD3+) |
| | CD8 | Cytotoxic T-Lymphocytes (CD8+) |
| | PD-L1 | Total PD-L1 expression (expressed as area of ROI containing PD-L1 positive staining) |
| 6b | CD3 | Total T-lymphocytes (CD3+) |
| | CD8 | Cytotoxic T-Lymphocytes (CD8+) |
| | PD-L1 | Total PD-L1 expression (expressed as total number of cells in ROI staining positive for PD-L1) |
| 6c | CD3 | Total T-lymphocytes (CD3+) |
| | CD8 | Cytotoxic T-lymphocytes (CD8+) |
| | PD-L1 | PD-L1+ tumor cells |
| | | PD-L1+ non-tumor cells |
| 6d | CD3 | Total T-lymphocytes (CD3+) |
| | CD8 | Cytotoxic T-Lymphocytes (CD8+) |
| | PD-L1 | PD-L1+ immune cells |
| | | PD-L1+ non-immune cells |
| 6e | CD3 | Total T-lymphocytes (CD3+) |
| | CD8 | Cytotoxic T-Lymphocytes (CD8+) |
| | PD-L1 | PD-L1+ tumor cells |
| | | PD-L1+ immune cells |
| 6f | CD3 | Total T-lymphocytes (CD3+) |
| | CD8 | Cytotoxic T-Lymphocytes (CD8+) |
| | PD-L1 | PD-L1+ tumor cells |
| 6g | CD3 | Total T-lymphocytes (CD3+) |
| | CD8 | Cytotoxic T-Lymphocytes (CD8+) |
| | PD-L1 | PD-L1+ immune cells |
| 6h | CD3 | Total T-lymphocytes (CD3+) |
| | CD8 | Cytotoxic T-Lymphocytes (CD8+) |
| | PD-L1 | PD-L1+ membrane staining |
| 7 | CD3 | Total T-lymphocytes (CD3+) |
| | CD45RO | Memory T-lymphocytes (CD45RO+) |
| 8 | CD8 | Cytotoxic T-lymphocytes (CD8+) |
| | CD45RO | Memory T-lymphocytes (CD45RO+) |
| 9 | CD3 | Total T-lymphocytes (CD3+) |
| | CD45RA | Naïve T-lymphocytes (CD45RA+) |
| 10 | CD8 | Cytotoxic T-lymphocytes (CD8+) |
| | CD45RA | Naïve T-lymphocytes (CD45RA+) |
| 11 | CD3 | Total T-lymphocytes (CD3+) |
| | CD4 | Helper T-lymphocytes (CD4+) |
| 12 | CD8 | Cytotoxic T-lymphocytes (CD8+) |
| | CD4 | Helper T-lymphocytes (CD4+) |
| 13 | CD3 | Total T-lymphocytes (CD3+) |
| | CD8 | Cytotoxic T-Lymphocytes (CD8+) |
| | FoxP3 | Regulatory T-lymphocytes (FoxP3+) |
| | CD4 | Helper T-lymphocytes (CD4+) |
| 14 | CD8 | Cytotoxic T-Lymphocytes (CD8+) |
| | FoxP3 | Regulatory T-lymphocytes (FoxP3+) |
| | CD4 | Helper T-lymphocytes (CD4+) |

III.C. Histochemical Staining of Samples

The images used to generate the continuous scoring function, as well as images to which the continuous scoring function may be applied, may be obtained from a histochemically-stained tissue section. Sections of the samples are stained by applying a panel of one or more biomarker-specific reagents in combination with a set of appropriate detection reagents to generate a biomarker-stained section. Biomarker staining is typically accomplished by contacting a section of the sample with a biomarker-specific reagent under conditions that facilitate specific binding between the biomarker and the biomarker-specific reagent. The sample is then contacted with a set of detection reagents that interact with the biomarker-specific reagent to facilitate deposition a detectable moiety in close proximity the biomarker, thereby generating a detectable signal localized to the biomarker. Typically, wash steps are performed between application of different reagents to prevent unwanted non-specific staining of tissues. Where multiple biomarkers are being evaluated, a single serial section may be stained for each biomarker in a simplex staining scheme, or one or more serial sections may be stained for a plurality of the biomarkers in a multiplex staining scheme, or a combination of both simplex and multiplex stains. Biomarker-stained sections may optionally be additionally stained with a contrast agent (such as a hematoxylin stain) to visualize macromolecular structures. Additionally, a serial section of the biomarker-stained section may be stained with a morphological stain to facilitate ROI identification.

III.C.1. Labeling Schemes and Associated Reagents

The biomarker-specific reagent facilitates detection of the biomarker by mediating deposition of a detectable moiety in close proximity to the biomarker-specific reagent.

In some embodiments, the detectable moiety is directly conjugated to the biomarker-specific reagent, and thus is deposited on the sample upon binding of the biomarker-specific reagent to its target (generally referred to as a direct labeling method). Direct labeling methods are often more directly quantifiable, but often suffer from a lack of sensitivity. In other embodiments, deposition of the detectable moiety is effected by the use of a detection reagent associated with the biomarker-specific reagent (generally referred to as an indirect labeling method).

Indirect labeling methods have the increase the number of detectable moieties that can be deposited in proximity to the biomarker-specific reagent, and thus are often more sensitive than direct labeling methods, particularly when used in combination with dyes.

In some embodiments, an indirect method is used, wherein the detectable moiety is deposited via an enzymatic reaction localized to the biomarker-specific reagent. Suitable enzymes for such reactions are well-known and include, but are not limited to, oxidoreductases, hydrolases, and peroxidases. Specific enzymes explicitly included are horseradish peroxidase (HRP), alkaline phosphatase (AP), acid phosphatase, glucose oxidase, β-galactosidase, β-glucuronidase, and β-lactamase. The enzyme may be directly conjugated to the biomarker-specific reagent, or may be indirectly associated with the biomarker-specific reagent via a labeling conjugate. As used herein, a "labeling conjugate" comprises:

(a) a specific detection reagent; and (b) an enzyme conjugated to the specific detection reagent, wherein the enzyme is reactive with the chromogenic substrate, signaling conjugate, or enzyme-reactive dye under appropriate reaction conditions to effect in situ generation of the dye and/or deposition of the dye on the tissue sample.

In non-limiting examples, the specific detection reagent of the labeling conjugate may be a secondary detection reagent (such as a species-specific secondary antibody bound to a primary antibody, an anti-hapten antibody bound to a hapten-conjugated primary antibody, or a biotin-binding protein bound to a biotinylated primary antibody), a tertiary detection reagent (such as a species-specific tertiary antibody bound to a secondary antibody, an anti-hapten antibody bound to a hapten-conjugated secondary antibody, or a biotin-binding protein bound to a biotinylated secondary antibody), or other such arrangements. An enzyme thus localized to the sample-bound biomarker-specific reagent can then be used in a number of schemes to deposit a detectable moiety.

In some cases, the enzyme reacts with a chromogenic compound/substrate. Particular non-limiting examples of chromogenic compounds/substrates include 4-nitrophenylphospate (pNPP), fast red, bromochloroindolyl phosphate (BCIP), nitro blue tetrazolium (NBT), BCIP/NBT, fast red, AP Orange, AP blue, tetramethylbenzidine (TMB), 2,2'-azino-di-[3-ethylbenzothiazoline sulphonate] (ABTS), o-dianisidine, 4-chloronaphthol (4-CN), nitrophenyl-β-D-galactopyranoside (ONPG), o-phenylenediamine (OPD), 5-bromo-4-chloro-3-indolyl-β-galactopyranoside (X-Gal), methylumbelliferyl-β-D-galactopyranoside (MU-Gal), p-nitrophenyl-α-D-galactopyranoside (PNP), 5-bromo-4-chloro-3-indolyl-β-D-glucuronide (X-Gluc), 3-amino-9-ethyl carbazol (AEC), fuchsin, iodonitrotetrazolium (INT), tetrazolium blue, or tetrazolium violet.

In some embodiments, the enzyme can be used in a metallographic detection scheme. Metallographic detection methods include using an enzyme such as alkaline phosphatase in combination with a water-soluble metal ion and a redox-inactive substrate of the enzyme. In some embodiments, the substrate is converted to a redox-active agent by the enzyme, and the redox-active agent reduces the metal ion, causing it to form a detectable precipitate. (see, for example, U.S. patent application Ser. No. 11/015,646, filed Dec. 20, 2004, PCT Publication No. 2005/003777 and U.S. Patent Application Publication No. 2004/0265922; each of which is incorporated by reference herein in its entirety). Metallographic detection methods include using an oxidoreductase enzyme (such as horseradish peroxidase) along with a water soluble metal ion, an oxidizing agent and a reducing agent, again to for form a detectable precipitate. (See, for example, U.S. Pat. No. 6,670,113, which is incorporated by reference herein in its entirety).

In some embodiments, the enzymatic action occurs between the enzyme and the dye itself, wherein the reaction converts the dye from a non-binding species to a species deposited on the sample. For example, reaction of DAB with a peroxidase (such as horseradish peroxidase) oxidizes the DAB, causing it to precipitate.

In yet other embodiments, the detectable moiety is deposited via a signaling conjugate comprising a latent reactive moiety configured to react with the enzyme to form a reactive species that can bind to the sample or to other detection components. These reactive species are capable of reacting with the sample proximal to their generation, i.e. near the enzyme, but rapidly convert to a non-reactive species so that the signaling conjugate is not deposited at sites distal from the site at which the enzyme is deposited. Examples of latent reactive moieties include: quinone methide (QM) analogs, such as those described at WO2015124703A1, and tyramide conjugates, such as those described at, WO2012003476A2, each of which is hereby incorporated by reference herein in its entirety. In some examples, the latent reactive moiety is directly conjugated to a dye, such as N,N'-biscarboxypentyl-5,5'-disulfonato-indodicarbocyanine (Cy5), 4-(dimethylamino) azobenzene-4'-sulfonamide (DAB SYL), tetramethylrhodamine (DISCO Purple), and Rhodamine 110 (Rhodamine) In other examples, the latent reactive moiety is conjugated to one member of a specific binding pair, and the dye is linked to the other member of the specific binding pair. In other examples, the latent reactive moiety is linked to one member of a specific binding pair, and an enzyme is linked to the other member of the specific binding pair, wherein the enzyme is (a) reactive with a chromogenic substrate to effect generation of the dye, or (b) reactive with a dye to effect deposition of the dye (such as DAB). Examples of specific binding pairs include:

(1) a biotin or a biotin derivative (such as desthiobiotin) linked to the latent reactive moiety, and a biotin-binding entity (such as avidin, streptavidin, deglycosylated avidin (such as NEUTRAVIDIN), or a biotin binding protein having a nitrated tyrosine at its biotin binding site (such as CAPTAVIDIN)) linked to a dye or to an enzyme reactive with a chromogenic substrate or reactive with a dye (for example, a peroxidase linked to the biotin-binding protein when the dye is DAB); and (2) a hapten linked to the latent reactive moiety, and an anti-hapten antibody linked to a dye or to an enzyme reactive with a chromogenic substrate or reactive with a dye (for example, a peroxidase linked to the biotin-binding protein when the dye is DAB).

Non-limiting examples of biomarker-specific reagent and detection reagent combinations are set forth in Table 2 are specifically included.

TABLE 2

A. Biomarker-specific reagent linked directly to detectable moiety
Biomarker-specific reagent-Dye conjugate
B. Biomarker-specific reagent linked to enzyme reacting with detectable moiety
Biomarker-specific reagent-Enzyme conjugate + DAB
Biomarker-specific reagent-Enzyme conjugate + Chromogen
C. Biomarker-specific reagent linked to Enzyme reacting with detectable moiety

| | |
|---|---|
| C1. Signaling conjugate comprises detectable moiety | Biomarker-specific reagent-Enzyme conjugate + QM-Dye conjugate |
| | Biomarker-specific reagent-Enzyme conjugate + Tyramide-Dye conjugate |
| C2. Signaling conjugate comprises enzyme that reacts directly with detectable moiety | Biomarker-specific reagent-Enzyme conjugate + QM-Enzyme conjugate + DAB |
| | Biomarker-specific reagent-Enzyme conjugate + QM-Enzyme conjugate + Chromogen |
| | Biomarker-specific reagent-Enzyme conjugate + Tyramide-Enzyme conjugate + DAB |
| | Biomarker-specific reagent-Enzyme conjugate + Tyramide-Enzyme conjugate + Chromogen |
| C3. Signaling conjugate comprises enzyme that reacts with second signaling | Biomarker-specific reagent-Enzyme conjugate + QM-Enzyme conjugate + QM-Dye conjugate |
| | Biomarker-specific reagent-Enzyme conjugate + QM-Enzyme |

TABLE 2-continued

| | |
|---|---|
| conjugate comprising detectable moiety | conjugate + Tyramide-Dye conjugate<br>Biomarker-specific reagent-Enzyme conjugate + Tyramide-Enzyme conjugate + QM-Dye conjugate<br>Biomarker-specific reagent-Enzyme conjugate + Tyramide-Enzyme conjugate + Tyramide-Dye conjugate |
| C4. Signaling conjugate comprises member of a specific binding pair and other member of binding pair is linked to detectable moiety | Biomarker-specific reagent-Enzyme conjugate + Tyramide-(biotin/hapten) conjugate + Dye-(avidin/anti-hapten biomarker-specific reagent) conjugate<br>Biomarker-specific reagent-Enzyme conjugate + QM-(biotin/hapten) conjugate + Dye-(avidin/anti-hapten biomarker-specific reagent) conjugate |
| C5. Signaling conjugate comprises member of a specific binding pair and other member of binding pair is linked to enzyme reactive with detectable moiety | Biomarker-specific reagent-Enzyme conjugate + QM-(biotin/hapten) conjugate + Enzyme-(avidin/anti-hapten biomarker-specific reagent) conjugate + DAB<br>Biomarker-specific reagent-Enzyme conjugate + QM-(biotin/hapten) conjugate + Enzyme-(avidin/anti-hapten biomarker-specific reagent) conjugate + Chromogen<br>Biomarker-specific reagent-Enzyme conjugate + Tyramide-(biotin/hapten) conjugate + Enzyme-(avidin/anti-hapten biomarker-specific reagent) conjugate + DAB<br>Biomarker-specific reagent-Enzyme conjugate + Tyramide-(biotin/hapten) conjugate + Enzyme-(avidin/anti-hapten biomarker-specific reagent) conjugate + Chromogen |
| C6. Signaling conjugate comprises member of a specific binding pair and other member of binding pair is linked to enzyme reactive with second detectable moiety linked to a detectable moiety | Biomarker-specific reagent-Enzyme conjugate + QM-(biotin/hapten) conjugate + Enzyme-(avidin/anti-hapten biomarker-specific reagent) conjugate + Tyramide-Dye conjugate<br>Biomarker-specific reagent-Enzyme conjugate + QM-(biotin/hapten) conjugate + Enzyme-(avidin/anti-hapten biomarker-specific reagent) conjugate + QM-Dye conjugate<br>Biomarker-specific reagent-Enzyme conjugate + Tyramide-(biotin/hapten) conjugate + Enzyme-(avidin/anti-hapten biomarker-specific reagent) conjugate + Tyramide-Dye conjugate<br>Biomarker-specific reagent-Enzyme conjugate + Tyramide-(biotin/hapten) conjugate + Enzyme-(avidin/anti-hapten biomarker-specific reagent) conjugate + QM-Dye conjugate |
| D. Biomarker-specific reagent linked to member of specific binding pair | |
| D1. Dye linked to other member of specific binding pair | Biomarker-specific reagent-(biotin/hapten) conjugate + Dye-(avidin/anti-hapten biomarker-specific reagent) conjugate |
| D2. Enzyme linked to other member of specific binding pair, wherein the enzyme is reactive with detectable moiety | Biomarker-specific reagent-(biotin/hapten) conjugate + Enzyme-(avidin/anti-hapten biomarker-specific reagent) conjugate + DAB<br>Biomarker-specific reagent-(biotin/hapten) conjugate + Enzyme-(avidin/anti-hapten biomarker-specific reagent) conjugate + Chromogen<br>Biomarker-specific reagent-(biotin/hapten) conjugate + Enzyme-(avidin/anti-hapten biomarker-specific reagent) conjugate + QM-Dye conjugate<br>Biomarker-specific reagent-(biotin/hapten) conjugate + Enzyme-(avidin/anti-hapten biomarker-specific reagent) conjugate + Tyramide-Dye conjugate |
| E. Secondary detection reagent linked directly to detectable moiety | |
| Biomarker-specific reagent + 2° specific detection reagent-Dye conjugate | |
| F. Secondary detection reagent linked to Enzyme reacting with detectable moiety | |
| Biomarker-specific reagent + 2° specific detection reagent-Enzyme conjugate + DAB | |
| Biomarker-specific reagent + 2° specific detection reagent-Enzyme conjugate + Chromogen | |
| G. Secondary detection reagent linked to Enzyme reacting with detectable moiety | |
| G1. Signaling conjugate comprises detectable moiety | Biomarker-specific reagent + 2° specific detection reagent-Enzyme conjugate + QM-Dye conjugate<br>Biomarker-specific reagent + 2° specific detection reagent-Enzyme conjugate + Tyramide-Dye conjugate |
| G2. Signaling conjugate comprises enzyme that reacts directly with detectable moiety | Biomarker-specific reagent + 2° specific detection reagent-Enzyme conjugate + QM-Enzyme conjugate + DAB<br>Biomarker-specific reagent + 2° specific detection reagent-Enzyme conjugate + QM-Enzyme conjugate + Chromogen<br>Biomarker-specific reagent + 2° specific detection reagent-Enzyme conjugate + Tyramide-Enzyme conjugate + DAB<br>Biomarker-specific reagent + 2° specific detection reagent-Enzyme conjugate + Tyramide-Enzyme conjugate + Chromogen |
| G3. Signaling conjugate comprises enzyme that reacts | Biomarker-specific reagent + 2° specific detection reagent-Enzyme conjugate + QM-Enzyme conjugate + QM- |

TABLE 2-continued

| | |
|---|---|
| with second signaling conjugate comprising detectable moiety | Dye conjugate<br>Biomarker-specific reagent + 2° specific detection reagent-Enzyme conjugate + QM-Enzyme conjugate + Tyramide-Dye conjugate<br>Biomarker-specific reagent + 2° specific detection reagent-Enzyme conjugate + Tyramide-Enzyme conjugate + QM-Dye conjugate<br>Biomarker-specific reagent + 2° specific detection reagent-Enzyme conjugate + Tyramide-Enzyme conjugate + Tyramide-Dye conjugate |
| G4. Signaling conjugate comprises member of a specific binding pair and other member of binding pair is linked to detectable moiety | Biomarker-specific reagent + 2° specific detection reagent-Enzyme conjugate + Tyramide-(biotin/hapten) conjugate + Dye-(avidin/anti-hapten biomarker-specific reagent) conjugate<br>Biomarker-specific reagent + 2° specific detection reagent-Enzyme conjugate + QM-(biotin/hapten) conjugate + Dye-(avidin/anti-hapten biomarker-specific reagent) conjugate |
| G5. Signaling conjugate comprises member of a specific binding pair and other member of binding pair is linked to enzyme reactive with detectable moiety | Biomarker-specific reagent + 2° specific detection reagent-Enzyme conjugate + QM-(biotin/hapten) conjugate + Enzyme-(avidin/anti-hapten biomarker-specific reagent) conjugate + DAB<br>Biomarker-specific reagent + 2° specific detection reagent-Enzyme conjugate + QM-(biotin/hapten) conjugate + Enzyme-(avidin/anti-hapten biomarker-specific reagent) conjugate + Chromogen<br>Biomarker-specific reagent + 2° specific detection reagent-Enzyme conjugate + Tyramide-(biotin/hapten) conjugate + Enzyme-(avidin/anti-hapten biomarker-specific reagent) conjugate + DAB<br>Biomarker-specific reagent + 2° specific detection reagent-Enzyme conjugate + Tyramide-(biotin/hapten) conjugate + Enzyme-(avidin/anti-hapten biomarker-specific reagent) conjugate + Chromogen |
| G6. Signaling conjugate comprises member of a specific binding pair and other member of binding pair is linked to enzyme reactive with second detectable moiety linked to a detectable moiety | Biomarker-specific reagent + 2° specific detection reagent-Enzyme conjugate + QM-(biotin/hapten) conjugate + Enzyme-(avidin/anti-hapten biomarker-specific reagent) conjugate + Tyramide-Dye conjugate<br>Biomarker-specific reagent + 2° specific detection reagent-Enzyme conjugate + QM-(biotin/hapten) conjugate + Enzyme-(avidin/anti-hapten biomarker-specific reagent) conjugate + QM-Dye conjugate<br>Biomarker-specific reagent + 2° specific detection reagent-Enzyme conjugate + Tyramide-(biotin/hapten) conjugate + Enzyme-(avidin/anti-hapten biomarker-specific reagent) conjugate + Tyramide-Dye conjugate<br>Biomarker-specific reagent + 2° specific detection reagent-Enzyme conjugate + Tyramide-(biotin/hapten) conjugate + Enzyme-(avidin/anti-hapten biomarker-specific reagent) conjugate + QM-Dye conjugate |
| H. Secondary detection reagent linked to member of specific binding pair | |
| H1. Dye linked to other member of specific binding pair | Biomarker-specific reagent + 2° specific detection reagent-(biotin/hapten) conjugate + Dye-(avidin/anti-hapten biomarker-specific reagent) conjugate |
| H2. Enzyme linked to other member of specific binding pair, wherein the enzyme is reactive with detectable moiety | Biomarker-specific reagent + 2° specific detection reagent-(biotin/hapten) conjugate + Enzyme-(avidin/anti-hapten biomarker-specific reagent) conjugate + DAB<br>Biomarker-specific reagent + 2° specific detection reagent-(biotin/hapten) conjugate + Enzyme-(avidin/anti-hapten biomarker-specific reagent) conjugate + Chromogen<br>Biomarker-specific reagent + 2° specific detection reagent-(biotin/hapten) conjugate + Enzyme-(avidin/anti-hapten biomarker-specific reagent) conjugate + QM-Dye conjugate<br>Biomarker-specific reagent + 2° specific detection reagent-(biotin/hapten) conjugate + Enzyme-(avidin/anti-hapten biomarker-specific reagent) conjugate + Tyramide-Dye conjugate |

I. Tertiary specific detection reagent linked directly to detectable moiety
Biomarker-specific reagent + 2° specific detection reagent + 3° specific detection reagent-Dye conjugate J. Tertiary specific detection reagent linked to Enzyme reacting with detectable moiety
Biomarker-specific reagent + 2° specific detection reagent + 3° specific detection reagent-Enzyme conjugate + DAB
Biomarker-specific reagent + 2° specific detection reagent + 3° specific detection reagent-Enzyme conjugate + Chromogen TABLE 2-continued K. Tertiary specific detection reagent linked to Enzyme reacting with detectable moiety

| | |
|---|---|
| K1. Signaling conjugate comprises detectable moiety | Biomarker-specific reagent + 2° specific detection reagent + 3° specific detection reagent-Enzyme conjugate + QM-Dye conjugate |
| | Biomarker-specific reagent + 2° specific detection reagent + 3° specific detection reagent-Enzyme conjugate + Tyramide-Dye conjugate |
| K2. Signaling conjugate comprises enzyme that reacts directly with detectable moiety | Biomarker-specific reagent + 2° specific detection reagent + 3° specific detection reagent-Enzyme conjugate + QM-Enzyme conjugate + DAB |
| | Biomarker-specific reagent + 2° specific detection reagent + 3° specific detection reagent-Enzyme conjugate + QM-Enzyme conjugate + Chromogen |
| | Biomarker-specific reagent + 2° specific detection reagent + 3° specific detection reagent-Enzyme conjugate + Tyrantide-Enzyme conjugate + DAB |
| | Biomarker-specific reagent + 2° specific detection reagent + 3° specific detection reagent-Enzyme conjugate + Tyramide-Enzyme conjugate + Chromogen |
| K3. Signaling conjugate comprises enzyme that reacts with second signaling conjugate comprising detectable moiety | Biomarker-specific reagent + 2° specific detection reagent + 3° specific detection reagent-Enzyme conjugate + QM-Enzyme conjugate + QM-Dye conjugate |
| | Biomarker-specific reagent + 2° specific detection reagent + 3° specific detection reagent-Enzyme conjugate + QM-Enzyme conjugate + Tyramide-Dye conjugate |
| | Biomarker-specific reagent + 2° specific detection reagent + 3° specific detection reagent-Enzyme conjugate + Tyramide-Enzyme conjugate + QM-Dye conjugate |
| | Biomarker-specific reagent + 2° specific detection reagent + 3° specific detection reagent-Enzyme conjugate + Tyramide-Enzyme conjugate + Tyramide-Dye conjugate |
| K4. Signaling conjugate comprises member of a specific binding pair and other member of binding pair is linked to detectable moiety | Biomarker-specific reagent + 2° specific detection reagent + 3° specific detection reagent-Enzyme conjugate + Tyramide-(biotin/hapten) conjugate + Dye-(avidin/anti-hapten biomarker-specific reagent) conjugate |
| | Biomarker-specific reagent + 2° specific detection reagent + 3° specific detection reagent-Enzyme conjugate + QM-(biotin/hapten) conjugate + Dye-(avidin/anti-hapten biomarker-specific reagent) conjugate |
| K5. Signaling conjugate comprises member of a specific binding pair and other member of binding pair is linked to enzyme reactive with detectable moiety | Biomarker-specific reagent + 2° specific detection reagent + 3° specific detection reagent-Enzyme conjugate + QM-(biotin/hapten) conjugate + Enzyme-(avidin/anti-hapten biomarker-specific reagent) conjugate + DAB |
| | Biomarker-specific reagent + 2° specific detection reagent + 3° specific detection reagent-Enzyme conjugate + QM-(biotin/hapten) conjugate + Enzyme-(avidin/anti-hapten biomarker-specific reagent) conjugate + Chromogen |
| | Biomarker-specific reagent + 2° specific detection reagent + 3° specific detection reagent-Enzyme conjugate + Tyramide-(biotin/hapten) conjugate + Enzyme -(avidin/anti-hapten biomarker-specific reagent) conjugate + DAB |
| | Biomarker-specific reagent + 2° specific detection reagent + 3° specific detection reagent-Enzyme conjugate + Tyramide-(biotin/hapten) conjugate + Enzyme -(avidin/anti-hapten biomarker-specific reagent) conjugate + Chromogen |
| K6. Signaling conjugate comprises member of a specific binding pair and other member of binding pair is linked to enzyme reactive with second detectable moiety linked to a detectable moiety | Biomarker-specific reagent + 2° specific detection reagent + 3° specific detection reagent-Enzyme conjugate + QM-(biotin/hapten) conjugate + Enzyme-(avidin/anti-hapten biomarker-specific reagent) conjugate + Tyramide-Dye conjugate |
| | Biomarker-specific reagent + 2° specific detection reagent + 3° specific detection reagent-Enzyme conjugate + QM-(biotin/hapten) conjugate + Enzyme-(avidin/anti-hapten biomarker-specific reagent) conjugate + QM-Dye conjugate |
| | Biomarker-specific reagent + 2° specific detection reagent + 3° specific detection reagent-Enzyme conjugate + Tyramide-(biotin/hapten) conjugate + Enzyme-(avidin/anti-hapten biomarker-specific reagent) conjugate + Tyramide-Dye conjugate |
| | Biomarker-specific reagent + 2° specific detection reagent + 3° specific detection reagent-Enzyme conjugate + Tyramide-(biotin/hapten) conjugate + Enzyme- |

TABLE 2-continued

| | |
|---|---|
| | (avidin/anti-hapten biomarker-specific reagent) conjugate + QM-Dye conjugate |
| L. Tertiary specific detection reagent linked to member of specific binding pair | |
| L1. Dye linked to other member of specific binding pair | Biomarker-specific reagent + 2° specific detection reagent + 3° specific detection reagent-(biotin/hapten) conjugate + Dye-(avidin/anti-hapten biomarker-specific reagent) conjugate |
| L2. Enzyme linked to other member of specific binding pair, wherein the enzyme is reactive with detectable moiety | Biomarker-specific reagent + 2° specific detection reagent + 3° specific detection reagent-(biotin/hapten) conjugate + Enzyme-(avidin/anti-hapten biomarker-specific reagent) conjugate + DAB<br>Biomarker-specific reagent + 2° specific detection reagent + 3° specific detection reagent-(biotin/hapten) conjugate + Enzyme-(avidin/anti-hapten biomarker-specific reagent) conjugate + Chromogen<br>Biomarker-specific reagent + 2° specific detection reagent + 3° specific detection reagent-(biotin/hapten) conjugate + Enzyme-(avidin/anti-hapten biomarker-specific reagent) conjugate + QM-Dye conjugate<br>Biomarker-specific reagent + 2° specific detection reagent + 3° specific detection reagent-(biotin/hapten) conjugate + Enzyme-(avidin/anti-hapten biomarker-specific reagent) conjugate + Tyramide-Dye conjugate |

In a specific embodiment, the biomarker-specific reagents and the specific detection reagents set forth in Table 2 are antibodies. As would be appreciated by a person having ordinary skill in the art, the detection scheme for each of the biomarker-specific reagent may be the same, or it may be different.

Non-limiting examples of commercially available detection reagents or kits comprising detection reagents suitable for use with present methods include: VENTANA ULTRAVIEW detection systems (secondary antibodies conjugated to enzymes, including HRP and AP); VENTANA IVIEW detection systems (biotinylated anti-species secondary antibodies and streptavidin-conjugated enzymes); VENTANA OPTIVIEW detection systems (anti-species secondary antibody conjugated to a hapten and an anti-hapten tertiary antibody conjugated to an enzyme multimer); VENTANA Amplification kit (unconjugated secondary antibodies, which can be used with any of the foregoing VENTANA detection systems to amplify the number of enzymes deposited at the site of primary antibody binding); VENTANA OPTIVIEW Amplification system (Anti-species secondary antibody conjugated to a hapten, an anti-hapten tertiary antibody conjugated to an enzyme multimer, and a tyramide conjugated to the same hapten. In use, the secondary antibody is contacted with the sample to effect binding to the primary antibody. Then the sample is incubated with the anti-hapten antibody to effect association of the enzyme to the secondary antibody. The sample is then incubated with the tyramide to effect deposition of additional hapten molecules. The sample is then incubated again with the anti-hapten antibody to effect deposition of additional enzyme molecules. The sample is then incubated with the detectable moiety to effect dye deposition); VENTANA DISCOVERY, DISCOVERYOMNIMAP, DISCOVERY ULTRAMAP anti-hapten antibody, secondary antibody, chromogen, fluorophore, and dye kits, each of which are available from Ventana Medical Systems, Inc. (Tucson, Ariz.); POWERVISION and PowerVision+ IHC Detection Systems (secondary antibodies directly polymerized with HRP or AP into compact polymers bearing a high ratio of enzymes to antibodies); and DAKO EnVision™+ System (enzyme labeled polymer that is conjugated to secondary antibodies).

III.C.2. Multiplex Labeling Schemes

In some embodiments, the biomarker-specific reagents and detection reagents are applied in a multiplex staining method. In multiplex methods, the biomarker-specific reagents and detection reagents must be applied in a manner that allows the different biomarkers to be differentially labeled.

One way to accomplish differential labelling of different biomarkers is to select combinations of biomarker-specific reagents, detection reagents, and enzyme combinations that will not result in off-target cross-reactivity between different antibodies or detection reagents (termed "combination staining"). For example, where secondary detection reagents are used, each secondary detection reagent is capable of binding to only one of the primary antibodies used on the section. For example, primary antibodies could be selected that are derived from different animal species (such as mouse, rabbit, rat, and got antibodies), in which case species-specific secondary antibodies may be used. As another example, each primary antibody may include a different hapten or epitope tag, and the secondary antibodies are selected to specifically bind to the hapten or epitope tag. Additionally, each set of detection reagents should be adapted to deposit a different detectable entity on the section, such as by depositing a different enzyme in proximity to each biomarker-specific reagent. An example of such an arrangement is shown at U.S. 8,603,765. Such arrangements have the potential advantage of being able to have each set of biomarker-specific reagents and associated specific binding reagents present on the sample at the same time and/or to perform staining with cocktails of biomarker-specific reagents and detection reagents, thereby reducing the number of staining steps. However, such arrangements may not always be feasible, as reagents may cross-react with different enzymes, and the various antibodies may cross-react with one another, leading to aberrant staining.

Another way to accomplish differential labelling of different biomarkers is to sequentially stain the sample for each biomarker. In such an embodiment, a first biomarker-specific reagent is reacted with the section, followed by a secondary detection reagent to the first biomarker-specific reagent and other detection reagents resulting in deposition of a first detectable entity. The section is then treated to remove the biomarker-specific reagents and associated detection reagents from the section while leaving the deposited stain in place. The process is repeated for subsequent biomarker-specific reagent. Examples of methods for removing the biomarker-specific reagents and associated detection reagents include heating the sample in the presence of a buffer that elutes the antibodies from the sample (termed a "heat-kill method"), such as those disclosed by Stack et al., Multiplexed immunohistochemistry, imaging, and quantitation: A review, with an assessment of Tyramide signal amplification, multispectral imaging and multiplex analysis, Methods, Vol. 70, Issue 1, pp 46-58 (November 2014), and PCT/EP2016/057955, the contents of which are incorporated by reference.

As will be appreciated by the skilled artisan, combination staining and sequential staining methods may be combined. For example, where only a subset of the primary antibodies is compatible with combination staining, the sequential staining method can be modified, wherein the antibodies compatible with combination staining are applied to the sample using a combination staining method, and the remaining antibodies are applied using a sequential staining method.

III.C.3. Counterstaining

If desired, the biomarker-stained slides may be counterstained to assist in identifying morphologically relevant areas for identifying ROIs, either manually or automatically. Examples of counterstains include chromogenic nuclear counterstains, such as hematoxylin (stains from blue to violet), Methylene blue (stains blue), toluidine blue (stains nuclei deep blue and polysaccharides pink to red), nuclear fast red (also called Kernechtrot dye, stains red), and methyl green (stains green); non-nuclear chromogenic stains, such as eosin (stains pink); fluorescent nuclear stains, including 4', 6-diamino-2-pheylindole (DAPI, stains blue), propidium iodide (stains red), Hoechst stain (stains blue), nuclear green DCS1 (stains green), nuclear yellow (Hoechst 5769121, stains yellow under neutral pH and stains blue under acidic pH), DRAQ5 (stains red), DRAQ7 (stains red); fluorescent non-nuclear stains, such as fluorophore-labelled phalloidin, (stains filamentous actin, color depends on conjugated fluorophore).

III.C.4. Morphological Staining of Samples

In certain embodiments, it is also desirable to morphologically stain a serial section of the biomarker-stained section. This section can be used to identify the ROIs from which scoring is conducted. Basic morpohological staining techniques often rely on staining nuclear structures with a first dye, and staining cytoplasmic structures with a second stain. Many morphological stains are known, including but not limited to, hematoxylin and eosin (H&E) stain and Lee's Stain (Methylene Blue and Basic Fuchsin). In a specific embodiment, at least one serial section of each biomarker-stained slide is H&E stained. Any method of applying H&E stain may be used, including manual and automated methods. In an embodiment, at least one section of the sample is an H&E stained sampled stained on a automated staining system. Automated systems for performing H&E staining typically operate on one of two staining principles: batch staining (also referred to as "dip'n dunk") or individual slide staining. Batch stainers generally use vats or baths of reagents in which many slides are immersed at the same time. Individual slide stainers, on the other hand, apply reagent directly to each slide, and no two slides share the same aliquot of reagent. Examples of commercially available H&E stainers include the VENTANA SYMPHONY (individual slide stainer) and VENTANA HE 600 (individual slide stainer) series H&E stainers from Roche; the DAKO COVERSTAINER (batch stainer) from Agilent Technologies; the LEICA ST4020 Small Linear Stainer (batch stainer), LEICA ST5020 MULTISTAINER (batch stainer), and the LEICA ST5010 AUTOSTAINER XL series (batch stainer) H&E stainers from Leica Biosystems Nussloch GmbH.

III.D. ROI Selection and Feature Metric Calculation

The ROIs selected in the present methods must perform at least two functions: (1) define a biologically significant region from which the immune cells and/or biomarkers are detected and quantitated; and (2) define a metric against which the immune cells and/or biomarkers can be compared to obtain the feature metric. Therefore, the ROI must be defined in a manner that encompasses a biologically relevant location of the tissue section and defines a metric that can allow the raw expression level of the biomarker to be compared across different samples. Examples of morphological regions of a tumor-containing tissue section that may have utility as a ROI include: a whole tumor (WT) region, an invasive margin (IM) region, a tumor core (TC) region; and a peri-tumoral (PT) region.

The ROI may be limited to the morphological region, may be expanded to include regions outside of the morphological region (i.e. by extending the margin of the ROI a defined distance outside of the morphological region), or may be restricted to a sub-region of the morphological region (for example, by shrinking the ROI a defined distance inside of the circumference of the morphological region or by identifying regions within the ROI having certain characteristics (such as a baseline density of certain cell types)). Where the morphological region is an edge region, the ROI may be defined as, for example, all points within a defined distance of any point of the edge, all points on one side of the edge within a defined distance of any point of the edge, a minimal geometric region (such as a circle, oval, square, rectangle, etc.) encompassing the entire edge region, all points within a circle having a defined radius centered on a center point of the edge region, etc.

In some embodiments, the same ROI may be used for all sections and biomarkers. For example, a morphologically defined ROI may be identified in an H&E-stained section of the sample and used for all biomarker-stained sections. In other embodiments, different ROIs may be used for different biomarkers.

For example, an H&E stained slide could be used to identify a particular morphological region used as a first ROI. A second ROI or ROIs may then be identified in one of the biomarker-stained sections, for example, used for identifying regions having a class of cells at a certain threshold density. The second ROI or ROIs may then be used for quantification of an expression level of subsequent ROIs. Non-limiting examples where different ROIs are used for different biomarkers include the scenarios described in Table 3:

TABLE 3

| Biomarker Panel | ROI Description | Utility of ROI |
|---|---|---|
| Immune cell + one or more markers for a | 1. Whole tumor (optionally including stroma) | Identify all immune cell-rich regions proximal to the tumor |

TABLE 3-continued

| Biomarker Panel | ROI Description | Utility of ROI |
|---|---|---|
| subset of the immune cell | 2. Immune cell-rich region(s) | Quantify immune cells and/or subsets thereof within the immune cell-rich regions identified from (1) |
| Immune cell + one or more markers for a subset of the immune cell | 1. Morphological sub-region of the sample (such as a tumoral region, stromal region, peri-tumoral region, IM region, and/or TC region, up to and including the whole section) | Identify immune cell-rich regions within the defined morphological region |
| | 2. Immune cell-rich region(s) within the morphological region | Quantify immune cells and/or subsets thereof within the immune cell-rich regions identified from (1) |
| Immune cell + one or more markers for a subset of the immune cell | 1. Morphological region of the sample (up to and including the whole sample) | Identify all immune cell-rich regions proximal to the tumor |
| | 2. Morphological sub-region of the previously-defined region (such as a tumoral region, stromal region, peri-tumoral region, IM region, and/or TC region) | Identify immune cell-rich regions falling at least partially within the morphological sub-region |
| | 3. Immune cell-rich region(s) falling at least partially within the peri-tumoral region | Quantify immune cell marker-positive and/or subsets thereof within the immune cell-rich regions identified from (2) |
| Immune cell + Immune escape marker | 1. Whole tumor | Identify all immune cell-rich regions proximal to the tumor |
| | 2. Immune cell-rich region(s) expanded a defined distance surrounding the region | Characterize extent of immune escape marker expression proximal to immune-rich regions |
| Immune cell + one or more markers for a subset of the immune cell + Immune escape marker | 1. Whole tumor (optionally including stroma) | a. Identify all immune cell-rich regions proximal to the tumor; b. Characterize extent of immune escape marker in sample |
| | 2. Immune cell-rich region(s) | Quantify immune cells and/or subsets thereof within the immune cell-rich regions identified from (1a) |
| Immune cell + one or more markers for a subset of the immune cell + Immune escape marker | 1. Whole tumor (optionally including stroma) | Identify all immune cell-rich regions proximal to the tumor |
| | 2. Immune cell-rich region(s) | Quantify immune cells and/or subsets thereof within the immune cell-rich regions identified from (1) |
| | 3. Immune cell-rich region(s) from (2) expanded defined distance surrounding the region | Characterize extent of immune escape marker expression proximal to immune cell-rich regions |
| Immune cell + one or more markers for a subset of the immune cell + Immune escape marker | 1. Morphological sub-region(s) of the sample (such as a tumoral region, stromal region, peri-tumoral region, IM region, and/or TC region) | a. Identify all immune cell-rich regions within the morphological sub-region; b. Characterize extent of immune escape marker expression in the sub-region |
| | 2. Immune cell-rich region(s) within the morphological region | Quantify immune cells and/or subsets thereof within the immune cell-rich regions identified from (1a) |
| Immune cell + one or more markers for a subset of the immune cell + Immune escape marker | 1. Morphological region of the sample (up to and including the whole sample) | a. Identify all immune cell-rich regions proximal to the tumor; b. Characterize extent of immune escape marker expression in the sub-region |
| | 2. Morphological sub-region of the previously-defined region (such as a tumoral region, stromal region, peri-tumoral region, IM region, and/or TC region) | Identify immune cell-rich regions falling at least partially within the morphological sub-region |
| | 3. Immune cell-rich region(s) falling at least partially within the peri-tumoral region | Quantify immune cell marker-positive and/or subsets thereof within the immune cell-rich regions identified from (2) |
| Immune cell + one or more markers for a subset of the immune cell + Immune escape marker | 1. Morphological region of the sample (up to and including the whole sample) | Identify all immune cell-rich regions proximal to the tumor |
| | 2. Morphological sub-region of the previously-defined region (such as a tumoral region, stromal region, peri-tumoral region, IM region, and/or TC region) | Identify immune cell-rich regions falling at least partially within the morphological sub-region |
| | 3. Immune cell-rich region(s) falling at least partially within the | Quantify immune cell marker-positive and/or subsets thereof |

TABLE 3-continued

| Biomarker Panel | ROI Description | Utility of ROI |
| --- | --- | --- |
| | peri-tumoral region | within the immune cell-rich regions identified from (2) |
| | 4. Immune cell-rich region(s) falling at least partially within the peri-tumoral region expanded defined distance surrounding the region(s) | Characterize extent of immune escape marker expression proximal to immune-cell rich regions |

In an example, the Immune cell of Table 3 is a CD3+ cell or a lymphocyte identified morphologically. As used in this table 3, an "immune cell-rich region" is a region having an area above a threshold area with a density of immune cells above a threshold density (such as, for example, CD3+-cells or lymphocytes identified morphologically).

In some embodiments, the ROI is manually identified in the digital image. For example, a trained expert may manually delineate one or more morphological region(s) (such as an IM, TC, or WT region) on a digital image of the sample. The area(s) delineated in the image may then be used as the ROI for calculation of the feature metrics.

In other embodiments, a computer-implemented system may assist the user in annotating the ROI (termed, "semi-automated ROI annotation"). For example, the user may delineate one or more regions on the digital image, which the system then automatically transforms into a complete ROI. For example, if the desired ROI is an IM region, a user can delineate an IM region or a WT region, and the system applies a pattern recognition function that uses computer vision and machine learning to identify regions having similar morphological characteristics to an IM region. Thus, for example, an IM ROI could be annotated in a semi-automated manner by a method comprising:
  (a) a user annotates the IM in an H&E image of the sample by outlining the IM region; and
  (b) a computer system applies a pattern recognition function to identify additional areas of the sample that have the morphological characteristics of the outlined area, wherein the IM ROI includes the area annotated by the user and the areas automatically identified by the system.

In another example, an IM ROI could be annotated in a semi-automated manner by a method comprising:
  (a) a user annotates the IM in an H&E image of the sample by outlining the IM region; and
  (b) the computer system automatically identifies a line tracing a center line that bisects the outlined IM region across the length of the IM, and applies a pattern recognition function to identify areas of the tissue similar to the tissue within a pre-defined distance of the centerline, wherein the IM ROI includes the area outlined by the user and the areas automatically identified by the system.

In another example, an IM ROI could be annotated in a semi-automated manner by a method comprising:
  (a) a user annotates an IM region in an H&E image of the sample by tracing one or more edges of the IM region, such as an edge separating the IM region from an extra-tumoral region, an edge defining a center line bisecting the IM region lengthwise, and/or an edge separating the TC and IM regions; and
  (b) the computer system applies a pattern recognition function to identify areas of the tissue similar to the tissue within a pre-defined distance of the annotated edge, wherein the IM ROI includes the area outlined by the user and the areas automatically identified by the system.

In another example, an IM ROI could be annotated in a semi-automated manner by a method comprising:
  (a) a user outlines a WT region and an IM region in an H&E image of the sample; and
  (b) the computer system applies a pattern recognition function to identify areas of the WT region similar to the tissue within IM region, wherein the IM ROI includes the area outlined by the user and the areas automatically identified by the system.

In another example, an IM ROI could be annotated in a semi-automated manner by a method comprising:
  (a) a user outlines a WT region in an H&E image of the sample; and
  (b) the computer system applies a pattern recognition function that automatically identifies areas of the WT region having morphological characteristics of an IM region, wherein the IM ROI includes the areas automatically identified by the system.

As another example, a PT ROI could be identified by the user annotating an IM region or a WT region (or an edge defining one or more of such regions), and the computer system automatically translates the annotation into a PT region. Thus, for example, a PT ROI could be annotated in a semi-automated manner by a method comprising:
  (a) a user annotates the IM in an H&E image of the sample by outlining the IM region; and
  (b) the computer system automatically annotates a PT ROI encompassing the outlined IM region, and all points within a pre-defined distance of the outline of the IM region.

In another example, a PT ROI could be annotated in a semi-automated manner by a method comprising:
  (a) a user annotates the IM in an H&E image of the sample; and
  (b) the computer system automatically identifies a line tracing a center line that bisects the outlined IM region across the length of the IM, and annotates a PT ROI encompassing all points within a pre-defined distance of the center line.

In another example, a PT ROI could be annotated in a semi-automated manner by a method comprising:
  (a) a user annotates an IM region in an H&E image of the sample by tracing one or more edges of the IM region, such as an edge separating the IM region from an extra-tumoral region, an edge defining a center line bisecting the IM region lengthwise, and/or an edge separating the TC and IM regions; and
  (b) the computer system automatically annotates a PT ROI including all points within a pre-determined distance of the user-annotated edge(s).

In another example, a PT ROI could be annotated in a semi-automated manner by a method comprising:

(a) a user annotates the IM in an H&E image of the sample; and (b) the computer system automatically identifies expands the annotate region by a pre-defined distance, and then applies a pattern recognition function that automatically identifies areas outside of the expanded ROI that are morphologically similar to the expanded.

In another example, a PT ROI could be annotated in a semi-automated manner by a method comprising:

(a) a user annotates an IM region in an H&E image of the sample by tracing one or more edges the IM region, such as an edge separating the IM region from an extra-tumoral region, an edge defining a center line bisecting the IM region lengthwise, and/or an edge separating the TC and IM regions; and (b) the computer system automatically identifies annotates a first PT ROI including all regions within a pre-determined distance of the user-annotated edge(s), and then applies a pattern recognition function that automatically identifies second and subsequent PT ROIs by identifying regions of the sample having morphological characteristics similar to the first PT ROI.

In another example, a PT ROI could be annotated in a semi-automated manner by a method comprising:

(a) a user outlines a WT region and an IM region in an H&E image of the sample; and (b) the computer system automatically expands the IM region to have a pre-defined width and applies a pattern recognition function to identify areas of the WT region similar to the tissue within the expanded IM region, wherein the PT ROI includes the expanded IM ROI and the areas automatically identified by the system.

In another example, a PT ROI could be annotated in a semi-automated manner by a method comprising:

(a) a user outlines a WT region in an H&E image of the sample; and (b) the computer system annotates a PT ROI, the PT ROI encompassing all points within a predefined distance of the outline of the WT region.

Many other arrangements could be used as well. In cases in which ROI generation is semi-automated, the user may be given an option to modify the ROI annotated by the computer system, such as by expanding the ROI, annotating regions of the ROI or objects within the ROI to be excluded from analysis, etc.

In other embodiments, computer system may automatically suggest an ROI without any direct input from the user (termed an "automated ROI annotation"). For example, a previously-trained tissue segmentation function or other pattern recognition function may be applied to an unannotated image to identify the desired morphological region to use as an ROI. The user may be given an option to modify the ROI annotated by the computer system, such as by expanding the ROI, annotating regions of the ROI or objects within the ROI to be excluded from analysis, etc.

The feature metric is calculated by applying a metric of the ROI to the raw expression data of the biomarker within the ROI. Examples of ROI metrics that could be used for feature metric calculation include: area of the ROI; total number of cells within the ROI; total number of specific cell types within the ROI (such as tumor cells, immune cells, stromal cells, cells positive for a first biomarker, etc.), length of an edge defining the ROI (such as circumference of the ROI, or a length of a centerline bisecting the ROI), number of cells defining the edge of the ROI, etc. Specific examples of feature metrics include:

an area density of cells expressing the biomarker within the ROI (number of positive cells over area of ROI), an area density of biomarker-positive pixels (number of biomarker-positive pixels over area of ROI), a linear density of cells expressing the biomarker (total number of cells expressing the biomarker within the ROI over the linear length of the edge, such as the linear length of an edge defining the ROI (such as a circumference of the ROI, a line bisecting the ROI, a barrier between two morphological regions (such as an interface between a TC and IM region or an IM and an extra-tumoral region)), a linear density of biomarker-positive pixels (total number of biomarker-positive pixels within the ROI over the linear length of an edge defining the ROI (such as a circumference of the ROI, a line bisecting the ROI, a barrier between two morphological regions (such as an interface between a TC and IM region or an IM and an extra-tumoral region)), a ratio between the number of cells expressing the biomarker and the total number of cells in the ROI, a ratio between the number of cells expressing the biomarker and the total number of tumor cells in the ROI, a ratio between the number of cells expressing the biomarker and the total number of an immune cell type or subtype in the ROI, an area percentage of the total ROI having a density of cells expressing the biomarker above a predetermined threshold (i.e. area of ROI having cell density above a threshold value over total area of the ROI), or a linear percentage of an edge of the ROI in proximity to a mass of cells expressing the biomarker at a density above a predetermined threshold (i.e., number of pixels of the ROI edge within a maximum distance of a center or an edge of a mass of cells having a minimum number of positive cells at a minimal density over the total number of pixels constituting the ROI edge).

The feature metric may be based directly on the raw counts in the ROI (referred to hereafter as a "Total metric"), or based on a mean or median feature metric of a plurality of control regions within the ROI (hereafter referred to as a "global metric"). These two approaches are illustrated at FIG. 1. In both cases, an image of an IHC slide is provided having an ROI annotated (denoted as the region within the dashed line) and objects of interest identified. For the total metric approach, the feature metric is calculated by quantitating the relevant metric of all the marked features within the ROI ("ROI object metric") and dividing the ROI object metric (such as total marked objects or total area of marked biomarker expression, etc.) by the ROI metric (such as the area of the ROI, number of total cells within ROI, etc.) (step A1). For the global metric approach, a plurality of control regions (illustrated by the open circles) is overlaid on the ROI (step B1). A control region metric ("CR metric") is calculated by quantitating the relevant metric of the control region ("CR Object Metric") (such as total marked objects within the control region or total area of marked biomarker expression within the control region, etc.) and dividing it by a control region ROI metric ("CR ROI Metric") (such as the area of the control region, number of total cells within the control region, etc.) (step B2). A separate CR metric is calculated for each control region. The global metric is obtained by calculating the mean or the median of all CR metrics (Step B3).

Where control regions are used, any method of overlaying control regions for metric processing may be used. In a specific embodiment, the ROI may be divided into a plurality of grid spaces (which may be equal sized, randomly sized, or some combination of varying sizes), each grid space constituting a control region. Alternatively, a plurality of control regions having known sizes (which may be the same or different) may be placed adjacent to each other or overlapping one another to cover substantially the entire ROI. Other methods and arrangements may also be used, so long as the output is a feature metric for the ROI that can be compared across different samples.

Specific examples of biomarkers, associated ROIs and feature metrics are set forth below in Table 4. In each case, the "feature metric(s)" in Table 4 may refer to a total metric, to a control region metric, or to a global metric.

TABLE 4

| Biomarker Panel | Quantitative Biomarker Metric | ROI | Feature Metric(s) |
|---|---|---|---|
| Primary immune cell (e.g., CD3+ or lymphocytes) | Positive cells | Morphological region (such as TC, IM, Peri-tumor, or whole tumor) | Area density (number of positive cells over area of ROI)<br>Cell ratio (number of marker-positive cells relative to total cells in ROI) |
| Primary immune cell (e.g., CD3+ or lymphocytes identified morphologically) | Positive cells | Defined distance from leading edge of IM | Area density<br>Cell ratio<br>Linear density (number of positive cells over length of edge)<br>Linear cell ratio (number of positive cells relative to total tumor cells constituting edge) |
| Primary immune cell (e.g., CD3+ or lymphocytes identified morphologically) | Positive cells | Immune cell-rich regions within morphological region | Area ratio (area of immune cell-rich regions over total area of morphological region)<br>Cell ratio (Number of marker-positive cells within immune cell-rich regions over total cells in morphological region) |
| Secondary immune cell markers (e.g., CD8, FoxP3, etc.) | Marker-positive cells | Morphological region (such as TC, IM, Peri-tumor, or whole tumor) | Area density (number of positive cells over area of ROI)<br>Cell ratio (number of positive cells relative to total cells in ROI) |
| Secondary immune cell markers (e.g., CD8, FoxP3, etc.) | Marker-positive cells | Defined distance from leading edge of IM | Area density<br>Cell ratio<br>Linear density (number of positive cells over length of edge)<br>Linear cell ratio (number of positive cells relative to total tumor cells constituting edge) |
| Secondary immune cell markers (e.g., CD8, FoxP3, etc.) | Marker-positive cells | Immune cell-rich regions within morphological region | Secondary cell ratio (Marker-positive cells within immune cell-rich regions over total cells in morphological region)<br>Immune cell ratio (Marker-positive cells within immune cell-rich regions over total primary marker-cells in morphological region)<br>Secondary cell density (area of marker-positive cells within immune cell-rich regions over total area of morphological region) |
| Immune escape molecules | Marker-positive cells | Morphological region (such as TC, IM, Peri-tumor, or whole tumor) | Area density (number of positive cells over area of ROI)<br>Cell ratio (number of marker-positive cells relative to total cells in ROI)<br>Immune cell ratio (number of marker-positive cells to total immune cells in ROI)<br>Tumor cell ratio (number of marker-positive cells to total tumor cells in ROI) |
| Immune escape molecules | Marker-positive cells | Defined distance from leading edge of IM | Area density<br>Cell ratio<br>Linear density (number of positive cells over length of edge)<br>Linear cell ratio (number of positive cells relative to total tumor cells constituting edge) |
| Immune escape molecules | Marker-positive cells | Immune cell-rich regions within morphological region | Area ratio (area of marker-positive cells in morphological region relative to area of immune cell-rich regions)<br>Cell ratio (number of marker-positive cells in morphological region relative to number of immune cells in immune cell-rich regions) |
| Immune escape molecules | Marker-positive tumor cells | Morphological region (such as TC, IM, Peri-tumor, or whole tumor) | Area density (number of positive tumor cells over area of ROI)<br>Cell ratio (number of marker-positive tumor cells relative to total cells in ROI)<br>Immune cell ratio (number of marker-positive tumor cells to total immune cells in ROI)<br>Tumor cell ratio (number of marker-positive tumor cells to total tumor cells in ROI) |

TABLE 4-continued

| Biomarker Panel | Quantitative Biomarker Metric | ROI | Feature Metric(s) |
|---|---|---|---|
| Immune escape molecules | Marker-positive tumor cells | Defined distance from leading edge of IM | Marker-positive cell ratio (number of marker-positive tumor cells to total marker-positive cells in ROI) Area density Cell ratio Linear density (number of marker-positive tumor cells over length of edge) Linear cell ratio (number of marker-positive tumor cells relative to total tumor cells constituting edge) |
| Immune escape molecules | Marker-positive tumor cells | Immune cell-rich regions within morphological region | Area ratio (area of marker-positive tumor cells in morphological region relative to area of immune cell-rich regions) Cell ratio (number of marker-positive tumor cells in morphological region relative to number of immune cells in immune cell-rich regions) |
| Immune escape molecules | Marker-positive immune cells | Morphological region (such as TC, IM, Peri-tumor, or whole tumor) | Area density (number of marker-positive immune cells over area of ROI) Cell ratio (number of marker-positive immune cells relative to total cells in ROI) Immune cell ratio (number of marker-positive immune cells to total immune cells in ROI) Tumor cell ratio (number of marker-positive immune cells to total tumor cells in ROI) Marker-positive cell ratio (number of marker-positive immune cells to total marker-positive cells in ROI) |
| Immune escape molecules | Marker-positive immune cells | Defined distance from leading edge of IM | Area density Cell ratio Linear density (number of marker-positive immune cells over length of edge) Linear cell ratio (number of marker-positive immune cells relative to total tumor cells constituting edge) |
| Immune escape molecules | Marker-positive immune cells | Immune cell-rich regions within morphological region | Area ratio (area of marker-positive immune cells in morphological region relative to area of immune cell-rich regions) Cell ratio (number of marker-positive immune cells in morphological region relative to number of immune cells in immune cell-rich regions) |
| Immune escape molecules | Membrane expression level | Morphological region (such as TC, IM, Peri-tumor, or whole tumor) | Area density (area of marker-positive membrane staining over total area of ROI) Cell density (area of marker-positive membrane staining relative to total cells in ROI) Membrane area ratio (area of marker-positive membrane staining relative to total membrane area in ROI) Tumor cell density (area of marker-positive membrane staining relative to total tumor cells in ROI) |
| Immune escape molecules | Membrane expression level | Defined distance from leading edge of IM | Area density Cell density Linear density (area of marker-positive membrane staining over length of edge) |
| Immune escape molecules | Membrane expression level | Immune cell-rich regions within morphological region | Area ratio (area of marker-positive membrane staining in morphological region relative to area of immune cell-rich regions) Cell density (area of marker-positive membrane staining in morphological region relative to number of cells in immune cell-rich regions) |
| Immune Escape Molecules | Positive pixels | Morphological region (such as TC, IM, Peri-tumor, or whole tumor) | Area ratio (area of marker-positive pixels over total area of ROI) Cell density (area of marker-positive pixels relative to total cells in ROI) Tumor cell density (area of marker-positive pixels relative to total tumor cells in ROI) Immune cell density (area of marker-positive pixels relative to total immune cells in ROI) |
| Immune Escape Molecules | Positive pixels | Defined distance from leading edge of IM | Area ratio (area of marker-positive pixels over total area of ROI) Cell density (area of marker-positive pixels |

TABLE 4-continued

| Biomarker Panel | Quantitative Biomarker Metric | ROI | Feature Metric(s) |
|---|---|---|---|
| Immune Escape Molecules | Positive pixels | Immune cell-rich regions within morphological region | relative to total cells in ROI)<br>Tumor cell density (area of marker-positive pixels relative to total tumor cells in ROI)<br>Immune cell density (area of marker-positive pixels relative to total immune cells in ROI)<br>Linear density (number of marker-positive pixels relative to length of edge)<br>Linear cell ratio (number of marker-positive pixels relative to total tumor cells constituting edge)<br>Area ratio (area of marker-positive pixels in morphological region relative to area of immune cell-rich regions)<br>Cell density (area of marker-positive pixels in morphological region relative to number of cells in immune cell-rich regions) |

Specific exemplary combinations of biomarker panels, ROIs and feature metrics are set forth in Table 5:

TABLE 5

| Panel | ROI(s) | Feature metric(s) |
|---|---|---|
| CD3 only | TC region | CD3+ cell density |
| CD3 only | IM region | CD3+ cell density |
| CD3 only | PT region | CD3+ cell density |
| CD3 only | TC region + IM region | 1. CD3+ cell density in TC region<br>2. CD3+ cell density in IM region |
| CD3 only | TC region + PT region | 1. CD3+ cell density in TC region<br>2. CD3+ cell density in PT region |
| CD3 + CD8 | PT region | CD3+ cell density<br>CD8+ cell density |
| CD3 + CD8 | IM region | CD3+ cell density<br>CD8+ cell density |
| CD3 + CD8 | WT region | CD3+ cell density<br>CD8+ cell density |
| CD3 + CD8 | 1. IM region<br>2. TC region | CD3+ cell density from IM region<br>CD8+ cell density from IM region<br>CD3+ cell density from TC region<br>CD8+ cell density from TC region |
| CD3 + CD8 | 1. PT region<br>2. TC region | CD3+ cell density from PT region<br>CD8+ cell density from PT region<br>CD3+ cell density from TC region<br>CD8+ cell density from TC region |
| CD3 + CD8 | 1. PT region<br>2. CD3-rich region(s) within PT region | CD3-rich area ratio (area of CD3-rich region relative to area of PT region)<br>CD8+ cell density within CD3-rich regions |
| CD3 + CD8 | 1. IM region<br>2. CD3-rich region(s) within IM region | CD3-rich area ratio (area of CD3-rich region relative to area of IM region)<br>CD8+ cell density within CD3-rich regions |
| CD3 + CD8 | 1. WT region<br>2. CD3-rich region(s) within WT region | CD3-rich area ratio (area of CD3-rich region relative to area of WT region)<br>CD8+ cell density within CD3-rich regions |
| CD3 + CD8 | 1. IM region<br>2. CD3-rich region(s) within IM region<br>3. TC region<br>4. CD3-rich region(s) within TC region | CD3-rich area ratio of IM (area of CD3-rich regions in IM relative to area of IM region)<br>CD8+ cell density within CD3-rich regions of IM<br>CD3-rich area ratio of TC (area of CD3-rich regions in TC relative to area of TC region)<br>CD8+ cell density within CD3-rich regions of TC |
| CD3 + CD8 | 1. PT region<br>2. CD3-rich region(s) within PT region<br>3. TC region<br>4. CD3-rich region(s) within TC region | CD3-rich area ratio of PT (area of CD3-rich regions in PT relative to area of PT region)<br>CD8+ cell density within CD3-rich regions of PT<br>CD3-rich area ratio of TC (area of CD3-rich regions in TC relative to area of TC region)<br>CD8+ cell density within CD3-rich regions of TC |
| CD3 + CD8 | 1. PT region<br>2. CD3-poor region(s) within PT region | CD3-poor area ratio (area of CD3-poor region relative to area of PT region)<br>CD8+ cell density within CD3-poor regions |
| CD3 + CD8 | 1. IM region<br>2. CD3-poor region(s) within IM region | CD3-poor area ratio (area of CD3-poor region relative to area of IM region)<br>CD8+ cell density within CD3-poor regions |

TABLE 5-continued

| Panel | ROI(s) | Feature metric(s) |
|---|---|---|
| CD3 + CD8 | 1. WT region<br>2. CD3-poor region(s)<br>within WT region | CD3-poor area ratio (area of CD3-poor region relative to area of WT region)<br>CD8+ cell density within CD3-rpoor regions |
| CD3 + CD8 | 1. IM region<br>2. CD3-poor region(s)<br>within IM region<br>3. TC region<br>4. CD3-poor region(s)<br>within TC region | CD3-poor area ratio of IM (area of CD3-poor regions in IM relative to area of IM region)<br>CD8+ cell density within CD3-poor regions of IM<br>CD3-poor area ratio of TC (area of CD3-poor regions in TC relative to area of TC region)<br>CD8+ cell density within CD3-poor regions of TC |
| CD3 + CD8 | 1. PT region<br>2. CD3-poor region(s)<br>within PT region<br>3. TC region<br>4. CD3-poor region(s)<br>within TC region | CD3-poor area ratio of PT (area of CD3-poor regions in PT relative to area of PT region)<br>CD8+ cell density within CD3-poor regions of PT<br>CD3-poor area ratio of TC (area of CD3-poor regions in TC relative to area of TC region)<br>CD8+ cell density within CD3-poor regions of TC |
| CD3 + CD4 | PT region | CD3+ cell density<br>CD4+ cell density |
| CD3 + CD4 | IM region | CD3+ cell density<br>CD4+ cell density |
| CD3 + CD4 | WT region | CD3+ cell density<br>CD4+ cell density |
| CD3 + CD4 | 1. IM region<br>2. TC region | CD3+ cell density from IM region<br>CD4+ cell density from IM region<br>CD3+ cell density from TC region<br>CD4+ cell density from TC region |
| CD3 + CD4 | 1. PT region<br>2. TC region | CD3+ cell density from PT region<br>CD4+ cell density from PT region<br>CD3+ cell density from TC region<br>CD4+ cell density from TC region |
| CD3 + CD4 | 1. PT region<br>2. CD3-rich region(s)<br>within PT region | CD3-rich area ratio (area of CD3-rich region relative to area of PT region)<br>CD4+ cell density within CD3-rich regions |
| CD3 + CD4 | 1. IM region<br>2. CD3-rich region(s)<br>within IM region | CD3-rich area ratio (area of CD3-rich region relative to area of IM region)<br>CD4+ cell density within CD3-rich regions |
| CD3 + CD4 | 1. WT region<br>2. CD3-rich region(s)<br>within WT region | CD3-rich area ratio (area of CD3-rich region relative to area of WT region)<br>CD4+ cell density within CD3-rich regions |
| CD3 + CD4 | 1. IM region<br>2. CD3-rich region(s)<br>within IM region<br>3. TC region<br>4. CD3-rich region(s)<br>within TC region | CD3-rich area ratio of IM (area of CD3-rich regions in IM relative to area of IM region)<br>CD4+ cell density within CD3-rich regions of IM<br>CD3-rich area ratio of TC (area of CD3-rich regions in TC relative to area of TC region)<br>CD4+ cell density within CD3-rich regions of TC |
| CD3 + CD4 | 1. PT region<br>2. CD3-rich region(s)<br>within IM region<br>3. TC region<br>4. CD3-rich region(s)<br>within TC region | CD3-rich area ratio of PT (area of CD3-rich regions in PT relative to area of IM region)<br>CD4+ cell density within CD3-rich regions of IM<br>CD3-rich area ratio of TC (area of CD3-rich regions in TC relative to area of TC region)<br>CD4+ cell density within CD3-rich regions of TC |
| CD3 + CD4 | 1. PT region<br>2. CD3-poor region(s)<br>within PT region | CD3-poor area ratio (area of CD3-poor region relative to area of PT region)<br>CD4+ cell density within CD3-poor regions |
| CD3 + CD4 | 1. IM region<br>2. CD3-poor region(s)<br>within IM region | CD3-poor area ratio (area of CD3-poor region relative to area of IM region)<br>CD4+ cell density within CD3-poor regions |
| CD3 + CD4 | 1. WT region<br>2. CD3-poor region(s)<br>within WT region | CD3-rich area ratio (area of CD3-poor region relative to area of WT region)<br>CD4+ cell density within CD3-poor regions |
| CD3 + CD4 | 1. IM region<br>2. CD3-poor region(s)<br>within IM region<br>3. TC region<br>4. CD3-poor region(s)<br>within TC region | CD3-poor area ratio of IM (area of CD3-poor regions in IM relative to area of IM region)<br>CD4+ cell density within CD3-poor regions of IM<br>CD3-poor area ratio of TC (area of CD3-poor regions in TC relative to area of TC region)<br>CD4+ cell density within CD3-poor regions of TC |
| CD3 + CD4 | 1. PT region<br>2. CD3-poor region(s)<br>within IM region<br>3. TC region<br>4. CD3-poor region(s)<br>within TC region | CD3-poor area ratio of PT (area of CD3-poor regions in PT relative to area of IM region)<br>CD4+ cell density within CD3-poor regions of IM<br>CD3-poor area ratio of TC (area of CD3-poor regions in TC relative to area of TC region)<br>CD4+ cell density within CD3-poor regions of TC |
| CD3 + CD45RA | PT region | CD3+ cell density<br>CD45RA+ cell density |
| CD3 + CD45RA | IM region | CD3+ cell density<br>CD45RA+ cell density |
| CD3 + CD45RA | WT region | CD3+ cell density<br>CD45RA+ cell density |
| CD3 + | 1. IM region | CD3+ cell density from IM region |

TABLE 5-continued

| Panel | ROI(s) | Feature metric(s) |
|---|---|---|
| CD45RA | 2. TC region | CD45RA+ cell density from IM region |
| | | CD3+ cell density from TC region |
| | | CD45RA+ cell density from TC region |
| CD3 + | 1. PT region | CD3+ cell density from PT region |
| CD45RA | 2. TC region | CD45RA+ cell density from PT region |
| | | CD3+ cell density from TC region |
| | | CD45RA+ cell density from TC region |
| CD3 + | 1. PT region | CD3-rich area ratio (area of CD3-rich region |
| CD45RA | 2. CD3-rich region(s) | relative to area of PT region) |
| | within PT region | CD45RA+ cell density within CD3-rich regions |
| CD3 + | 1. IM region | CD3-rich area ratio (area of CD3-rich region |
| CD45RA | 2. CD3-rich region(s) | relative to area of IM region) |
| | within IM region | CD45RA+ cell density within CD3-rich regions |
| CD3 + | 1. WT region | CD3-rich area ratio (area of CD3-rich region |
| CD45RA | 2. CD3-rich region(s) | relative to area of WT region) |
| | within WT region | CD45RA+ cell density within CD3-rich regions |
| CD3 + | 1. IM region | CD3-rich area ratio of IM (area of CD3-rich |
| CD45RA | 2. CD3-rich region(s) | regions in IM relative to area of IM region) |
| | within IM region | CD45RA+ cell density within CD3-rich regions of IM |
| | 3. TC region | CD3-rich area ratio of TC (area of CD3-rich |
| | 4. CD3-rich region(s) | regions in TC relative to area of TC region) |
| | within TC region | CD45RA+ cell density within CD3-rich regions of TC |
| CD3 + | 1. PT region | CD3-rich area ratio of PT (area of CD3-rich |
| CD45RA | 2. CD3-rich region(s) | regions in PT relative to area of PT region) |
| | within PT region | CD45RA+ cell density within CD3-rich regions of PT |
| | 3. TC region | CD3-rich area ratio of TC (area of CD3-rich |
| | 4. CD3-rich region(s) | regions in TC relative to area of TC region) |
| | within TC region | CD45RA+ cell density within CD3-rich regions of TC |
| CD3 + | 1. PT region | CD3-poor area ratio (area of CD3-poor region |
| CD45RA | 2. CD3-poor region(s) | relative to area of PT region) |
| | within PT region | CD45RA+ cell density within CD3-poor regions |
| CD3 + | 1. IM region | CD3-poor area ratio (area of CD3-poor region |
| CD45RA | 2. CD3-poor region(s) | relative to area of IM region) |
| | within IM region | CD45RA+ cell density within CD3-poor regions |
| CD3 + | 1. WT region | CD3-poor area ratio (area of CD3-poor region |
| CD45RA | 2. CD3-poor region(s) | relative to area of WT region) |
| | within WT region | CD45RA+ cell density within CD3-poor regions |
| CD3 + | 1. IM region | CD3-poor area ratio of IM (area of CD3-poor |
| CD45RA | 2. CD3-poor region(s) | regions in IM relative to area of IM region) |
| | within IM region | CD45RA+ cell density within CD3-poor regions of IM |
| | 3. TC region | CD3-poor area ratio of TC (area of CD3-poor |
| | 4. CD3-poor region(s) | regions in TC relative to area of TC region) |
| | within TC region | CD45RA+ cell density within CD3-poor regions of TC |
| CD3 + | 1. PT region | CD3-poor area ratio of PT (area of CD3-poor |
| CD45RA | 2. CD3-poor region(s) | regions in PT relative to area of PT region) |
| | within PT region | CD45RA+ cell density within CD3-poor regions of PT |
| | 3. TC region | CD3-poor area ratio of TC (area of CD3-poor |
| | 4. CD3-poor region(s) | regions in TC relative to area of TC region) |
| | within TC region | CD45RA+ cell density within CD3-poor regions of TC |
| CD3 + | PT region | CD3+ cell density |
| CD45RO | | CD45RO+ cell density |
| CD3 + | IM region | CD3+ cell density |
| CD45RO | | CD45RO+ cell density |
| CD3 + | WT region | CD3+ cell density |
| CD45RO | | CD45RO+ cell density |
| CD3 + | 1. IM region | CD3+ cell density from IM region |
| CD45RO | 2. TC region | CD45RO+ cell density from IM region |
| | | CD3+ cell density from TC region |
| | | CD45RO+ cell density from TC region |
| CD3 + | 1. PT region | CD3+ cell density from PT region |
| CD45RO | 2. TC region | CD45RO+ cell density from PT region |
| | | CD3+ cell density from TC region |
| | | CD45RO+ cell density from TC region |
| CD3 + | 1. PT region | CD3-rich area ratio (area of CD3-rich region |
| CD45RO | 2. CD3-rich region(s) | relative to area of PT region) |
| | within PT region | CD45RO+ cell density within CD3-rich regions |
| CD3 + | 1. IM region | CD3-rich area ratio (area of CD3-rich region |
| CD45RO | 2. CD3-rich region(s) | relative to area of IM region) |
| | within IM region | CD45RO+ cell density within CD3-rich regions |
| CD3 + | 1. WT region | CD3-rich area ratio (area of CD3-rich region |
| CD45RO | 2. CD3-rich region(s) | relative to area of WT region) |
| | within WT region | CD45RO+ cell density within CD3-rich regions |
| CD3 + | 1. IM region | CD3-rich area ratio of IM (area of CD3-rich |
| CD45RO | 2. CD3-rich region(s) | regions in IM relative to area of IM region) |
| | within IM region | CD45RO+ cell density within CD3-rich regions of IM |
| | 3. TC region | CD3-rich area ratio of TC (area of CD3-rich |
| | 4. CD3-rich region(s) | regions in TC relative to area of TC region) |
| | within TC region | CD45RO+ cell density within CD3-rich regions of TC |

TABLE 5-continued

| Panel | ROI(s) | Feature metric(s) |
|---|---|---|
| CD3 + CD45RO | 1. PT region<br>2. CD3-rich region(s) within IM region<br>3. TC region<br>4. CD3-rich region(s) within TC region | CD3-rich area ratio of PT (area of CD3-rich regions in PT relative to area of IM region)<br>CD45RO+ cell density within CD3-rich regions of PT<br>CD3-rich area ratio of TC (area of CD3-rich regions in TC relative to area of TC region)<br>CD45RO+ cell density within CD3-rich regions of TC |
| CD3 + CD45RO | 1. PT region<br>2. CD3-poor region(s) within PT region | CD3-poor area ratio (area of CD3-poor region relative to area of PT region)<br>CD45RO+ cell density within CD3-poor regions |
| CD3 + CD45RO | 1. IM region<br>2. CD3-poor region(s) within IM region | CD3-poor area ratio (area of CD3-poor region relative to area of IM region)<br>CD45RO+ cell density within CD3-poor regions |
| CD3 + CD45RO | 1. WT region<br>2. CD3-poor region(s) within WT region | CD3-poor area ratio (area of CD3-poor region relative to area of WT region)<br>CD45RO+ cell density within CD3-poor regions |
| CD3 + CD45RO | 1. IM region<br>2. CD3-poor region(s) within IM region<br>3. TC region<br>4. CD3-poor region(s) within TC region | CD3-poor area ratio of IM (area of CD3-poor regions in IM relative to area of IM region)<br>CD45RO+ cell density within CD3-poor regions of IM<br>CD3-poor area ratio of TC (area of CD3-poor regions in TC relative to area of TC region)<br>CD45RO+ cell density within CD3-poor regions of TC |
| CD3 + CD45RO | 1. PT region<br>2. CD3-poor region(s) within IM region<br>3. TC region<br>4. CD3-poor region(s) within TC region | CD3-poor area ratio of PT (area of CD3-poor regions in PT relative to area of IM region)<br>CD45RO+ cell density within CD3-poor regions of PT<br>CD3-poor area ratio of TC (area of CD3-poor regions in TC relative to area of TC region)<br>CD45RO+ cell density within CD3-poor regions of TC |
| CD3 + FOXP3 | PT region | CD3+ cell density<br>FOXP3+ cell density |
| CD3 + FOXP3 | IM region | CD3+ cell density<br>FOXP3+ cell density |
| CD3 + FOXP3 | WT region | CD3+ cell density<br>FOXP3+ cell density |
| CD3 + FOXP3 | 1. IM region<br>2. TC region | CD3+ cell density from IM region<br>FOXP3+ cell density from IM region<br>CD3+ cell density from TC region<br>FOXP3+ cell density from TC region |
| CD3 + FOXP3 | 1. PT region<br>2. TC region | CD3+ cell density from PT region<br>FOXP3+ cell density from PT region<br>CD3+ cell density from TC region<br>FOXP3+ cell density from TC region |
| CD3 + FOXP3 | 1. PT region<br>2. CD3-rich region(s) within PT region | CD3-rich area ratio (area of CD3-rich region relative to area of PT region)<br>FOXP3+ cell density within CD3-rich regions |
| CD3 + FOXP3 | 1. IM region<br>2. CD3-rich region(s) within IM region | CD3-rich area ratio (area of CD3-rich region relative to area of IM region)<br>FOXP3+ cell density within CD3-rich regions |
| CD3 + FOXP3 | 1. WT region<br>2. CD3-rich region(s) within WT region | CD3-rich area ratio (area of CD3-rich region relative to area of WT region)<br>FOXP3+ cell density within CD3-rich regions |
| CD3 + FOXP3 | 1. IM region<br>2. CD3-rich region(s) within IM region<br>3. TC region<br>4. CD3-rich region(s) within TC region | CD3-rich area ratio of IM (area of CD3-rich regions in IM relative to area of IM region)<br>FOXP3+ cell density within CD3-rich regions of IM<br>CD3-rich area ratio of TC (area of CD3-rich regions in TC relative to area of TC region)<br>FOXP3+ cell density within CD3-rich regions of TC |
| CD3 + FOXP3 | 1. PT region<br>2. CD3-rich region(s) within PT region<br>3. TC region<br>4. CD3-rich region(s) within TC region | CD3-rich area ratio of PT (area of CD3-rich regions in PT relative to area of PT region)<br>FOXP3+ cell density within CD3-rich regions of PT<br>CD3-rich area ratio of TC (area of CD3-rich regions in TC relative to area of TC region)<br>FOXP3+ cell density within CD3-rich regions of TC |
| CD3 + FOXP3 | 1. PT region<br>2. CD3-poor region(s) within PT region | CD3-poor area ratio (area of CD3-poor region relative to area of PT region)<br>FOXP3+ cell density within CD3-poor regions |
| CD3 + FOXP3 | 1. IM region<br>2. CD3-poor region(s) within IM region | CD3-poor area ratio (area of CD3-poor region relative to area of IM region)<br>FOXP3+ cell density within CD3-poor regions |
| CD3 + FOXP3 | 1. WT region<br>2. CD3-poor region(s) within WT region | CD3-poor area ratio (area of CD3-poor region relative to area of WT region)<br>FOXP3+ cell density within CD3-poor regions |
| CD3 + FOXP3 | 1. IM region<br>2. CD3-poor region(s) within IM region<br>3. TC region<br>4. CD3-poor region(s) within TC region | CD3-poor area ratio of IM (area of CD3-poor regions in IM relative to area of IM region)<br>FOXP3+ cell density within CD3-poor regions of IM<br>CD3-poor area ratio of TC (area of CD3-poor regions in TC relative to area of TC region)<br>FOXP3+ cell density within CD3-poor regions of TC |

TABLE 5-continued

| Panel | ROI(s) | Feature metric(s) |
|---|---|---|
| CD3 + FOXP3 | 1. PT region<br>2. CD3-poor region(s) within PT region<br>3. TC region<br>4. CD3-poor region(s) within TC region | CD3-poor area ratio of PT (area of CD3-poor regions in PT relative to area of PT region)<br>FOXP3+ cell density within CD3-poor regions of PT<br>CD3-poor area ratio of TC (area of CD3-poor regions in TC relative to area of TC region)<br>FOXP3+ cell density within CD3-poor regions of TC |

The densities listed in Table 5 may in each case be a total metric or a global metric, and, unless otherwise stated, may in each case be an area density (i.e. number of positive cells over area of the ROI) or a linear density (i.e. number of positive cells over a linear length metric of the ROI, such as an edge length, a circumference, etc.). In each of these examples, the metrics related to CD3-cells may be replaced with total lymphocytes identified in an H&E-stained slide. All of the metrics listed in the "Feature metric" column of Table 5 may be normalized and/or subject to upper and/or lower limits, if desired. As used in this table 5, a "CD3-rich region" is a region having an area above a threshold area with a density of CD3+ cells (or total lymphocytes as identified by H&E stain) above a threshold density. As used in this table 5, a "CD3-poor region" is a region having an area above a threshold area with a density of CD3+ cells (or total lymphocytes as identified by H&E stain) below a threshold density.

III.E. Normalized Feature Metrics

If desired, the calculated feature metrics may optionally converted to a normalized feature vector.

In the typical example, before the continuous scoring function is modeled, the feature metrics calculated for the samples of the cohort are plotted, and the distribution is evaluated to identify any rightward or leftward skew. Biologically meaningful cutoffs (maximum cutoffs for right-skewed distributions, and/or minimum cutoffs for left-skewed distributions) are identified, and each sample having a value beyond the cutoff (above in the case of a right-skewed distribution, or below in the case of left-skewed distribution) is assigned a feature metric equal to the cutoff value. The cutoff value (hereafter referred to as the "normalization factor") is then applied to each feature metric. In the case of a right-skewed distribution, the feature metric is divided by the normalization factor to obtain the normalized feature metric, in which case the feature metric is expressed on a maximum scale (i.e. the value of the normalized metric will not exceed a pre-determined maximum, such as 1, 10, 100, etc.). Similarly, in the case of a left-skewed distribution, the feature metric is divided by the normalization factor to obtain the normalized feature metric, in which case the feature metric is expressed on a minimum scale (i.e. the value of the normalized metric will not fall below a pre-determined minimum, such as 1, 10, 100, etc.). If desired, the normalized feature metric may also be multiplied by or divided by a pre-determined constant value to obtain the desired scale (for example, for right skewed distributions, multiplied by 100 to obtain a percentage of the normalization factor instead of a fraction of the normalization factor). Normalized feature metrics may be calculated for test samples by applying the normalization factor and/or maximum and/or minimum cutoffs identified for modeling to the feature metric calculated for the test sample.

III.F. Modeling the Continuous Scoring Function

In order to identify the continuous scoring function, the feature metrics from the cohort of patients are modeled for their ability to predict the relative tumor prognosis, risk of progression, and/or likelihood of responding to a particular treatment course. In an embodiment, a "time-to-event" model is used. These models test each variable for the ability to predict the relative risk of a defined event occurring at any given time point. The "event" in such a case is typically overall survival, recurrence-free survival, and progression-free survival. In one example, the "time-to event" model is a Cox proportional hazard model for overall survival, recurrence-free survival, or progression-free survival. The Cox proportional hazard model can be written as formula 1:

$$ICS_{cox} = \exp(b_1 X_1 + b_2 X_2 + \ldots b_p X_p) \qquad \text{Formula 1}$$

in each case, wherein $X_1$, $X_2$, ... $X_p$ are the values of the feature metric(s) (which optionally may be subject to maximum and/or minimum cutoffs, and/or normalization), $b_1$, $b_2$ ... $b_p$ are constants extrapolated from the model for each of the feature metric(s). For each patient sample of the test cohort, data is obtained regarding the outcome being tracked (time to death, time to recurrence, or time to progression) and the feature metric for each biomarker being analyzed. Candidate Cox proportional models are generated by entering the feature metric data and survival data for each individual of the cohort into a computerized statistical analysis software suite (such as The R Project for Statistical Computing (available at r-project.org), SAS, MATLAB, among others). Each candidate model is tested for predictive ability using a concordance index, such as C-index. The model having the highest concordance score using the selected concordance index is selected as the continuous scoring function.

Additionally, one or more stratification cutoffs may be selected to separate the patients into "risk bins" according to relative risk (such as "high risk" and "low risk," quartiles, deciles, etc.). In one example, stratification cutoffs are selected using receiver operator characteristic (ROC) curves. ROC curves allow users to balance the sensitivity of the model (i.e. prioritize capturing as many "positive" or "high risk" candidates as possible) with the specificity of the model (i.e. minimizing false-positives for "high risk candidates"). In an embodiment, a cutoff between high risk and low risk bins for overall survival, recurrence-free survival or progression-free survival is selected, the cutoff chosen having the sensitivity and specificity balanced.

IV. Immune Context Scoring with a Continuous Scoring Function

After the continuous scoring function has been modeled and optional stratification cutoffs have been selected, the continuous scoring function may be applied to images of test samples to calculate an immune context score (ICS) for the test sample. The test samples are typically similar to the sample types used for modeling the continuous scoring function, except that outcomes are not yet known. The test samples are stained for the biomarkers relevant to the continuous scoring function and the relevant feature metrics are calculated, and if they are being used, the normalization factor(s) and/or maximum and/or minimum cutoffs are applied to the feature metrics to obtain the normalized feature metrics. The ICS is calculated by applying the continuous scoring function to the feature metrics or the normalized feature metrics. The immune context score may then be integrated into diagnostic and/or treatment decisions by a clinician, including, for example, by integrating the immune context score with clinical variables that relate to the outcome being measured.

IV.A. Clinical Applications of Certain Immune Context Scores

IV.A.1. Colorectal Cancer

In an embodiment, the continuous scoring function is developed for colorectal cancer as a function of patient prognosis, and the output of the continuous scoring function is used to determine a course of treatment for the patient. In an embodiment, the treatment course selected is based on the stage of the cancer, optionally in combination with other diagnostic factors. In a specific embodiment, the continuous scoring function uses a CD3 density and a CD8 density (each of which may be normalized and/or subject to maximum and/or minimum cutoffs), each density obtained from a WT region, from a PT region, from an IM region, from a PT and a TC region, or from an IM and a TC region. In an embodiment, the densities are area densities or linear densities. In an embodiment, each density is derived from a total metric or global metric. In an embodiment, the continuous scoring function is prognostic of 3 year recurrence-free survival. In another embodiment, the continuous scoring function is prognostic of 3 year progression-free survival. In another embodiment, the continuous scoring function is prognostic of 3 year overall survival. In another embodiment, the continuous scoring function is prognostic of 3 year disease-specific survival.

Stage 0 colorectal cancers are cancers that have not grown beyond the inner lining of the colon. Stage I colorectal cancers are cancers that have not spread outside of the colon wall itself or into nearby lymph nodes. Stage 0 and Stage I cancers are typically treated surgically, followed by post-surgical monitoring. In such a case, the course of treatment for the patient guided by the immune context score may relate to the extent and type of post-surgical monitoring of the patient and/or whether to administer a chemotherapy. For example, where an immune context score indicates a relatively high risk of recurrence or progression, post-surgical treatment may include intensified monitoring efforts, for example, by increasing the frequency of follow-up colonoscopies, monitoring circulating tumor cells (CTCs), etc.

Stage II colorectal cancers are cancers that have grown through the wall of the colon, and possibly into nearby tissue, but have not yet spread to the lymph nodes. Surgical removal of the tumor and nearby lymph nodes is typically performed at this stage, and may be accompanied by chemotherapy (typically adjuvant chemotherapy and/or radiation therapy for colon cancers; or as a neoadjuvant and/or adjuvant treatment for rectal cancers). Common chemotherapies include fluoropyrimidine-based, optionally in combination with leucovorin. Radiation therapy may also be appropriate at this stage. In one specific non-limiting embodiment, a method of treating a stage II colorectal cancer may comprise:

for subjects having a high risk of recurrence or progression as determined by an immune context score (optionally in combination with other diagnostic criteria), administering an adjuvant therapy comprising a fluoropyrimidine-based chemotherapy, optionally in combination with leucovorin and optionally in combination with radiation therapy; or for subjects having a low risk of recurrence or progression as determined by an immune context score (optionally in combination with other diagnostic criteria), administering a therapy course that includes post-surgical monitoring and does not include chemotherapy or a reduced course of chemotherapy.

In one specific embodiment, a continuous scoring function for prognosing stage II colorectal cancer is developed, wherein the continuous scoring function incorporates CD3-positive area cell densities and optionally CD8-positive area cell densities into an immune context score. In an embodiment, the ICS includes at least CD3 area cell densities in a tumor core region or in an invasive margin or peritumoral region. In another embodiment, the ICS includes CD3 cell density in both a tumor core region and an invasive margin or peritumoral region. In another embodiment, the ICS includes a CD3-positive cell density in an invasive margin or peritumoral region and includes a CD8-positive cell density in the invasive margin or peritumoral region. In another embodiment, the ICS includes a CD3-positive cell density in a tumor core region and includes a CD8-positive cell density in the tumor core region region. In one specific embodiment, the prognosis is made on the basis of the immune context score. In another specific embodiment, the prognosis is made on the basis of the immune context score in addition to one or more clinical variables. In an embodiment, the clinical variables are selected from the group consisting of age, sex, sidedness of the tumor, and number of lymph nodes harvested during tumor resection. In another embodiment, the clinical variables are integrated into a Cox proportional hazard model (referred to hereafter as a clinical model), and the clinical model is integrated with the ICS to generate a prognosis. In another embodiment, the ICS includes the one or more clinical variables.

IV.A.2. Breast cancer

In an embodiment, a continuous scoring function is developed for a breast cancer as a function of patient prognosis, and the output of the continuous scoring function is used to determine a course of treatment for the patient. In a specific embodiment, the continuous scoring function uses a normalized CD3 density and a normalized CD8 density, each density obtained from a peri-tumoral region, from an IM region, or from an IM and a TC region. In an embodiment, each normalized density is a global normalized metric. In an embodiment, the continuous scoring function is prognostic of at least 5 year recurrence-free survival. In another embodiment, the continuous scoring function is prognostic of at least 5 year progression-free survival. In another embodiment, the continuous scoring function is prognostic of at least 5 year overall survival. In another embodiment, the continuous scoring function is prognostic of at least 5 year disease-specific survival.

For stage I-stage III cancers, the primary treatment typically is surgical removal of the tumor or breast, optionally combined with radiation therapy and/or chemotherapy. Where the tumor is positive for estrogen receptor (ER) and/or progesterone receptor (PR) a hormone therapy (such as an aromatase inhibitor or an ER antagonists or partial agonists) is administered. Where the tumor is positive for HER2, a HER2-directed therapy (such as anti-HER2 monoclonal antibodies (including trastuzumab and pertuzumab) or small molecule HER2 inhibitors (including lapatinib) is administered. For stage I-III breast cancers, the immune context score may be used to determine whether or not to administer chemotherapy or radiation therapy as part of an adjuvant or neoadjuvant treatment course. In one specific non-limiting embodiment, an adjuvant or neodjuvant treatment course is selected for a stage I, stage II, or stage III invasive breast tumor, wherein:

for subjects having a high risk of recurrence or progression as determined by an immune context score (optionally in combination with other diagnostic criteria), the neoadjuvant or adjuvant treatment course includes chemotherapy and/or radiation therapy; or for subjects having a low risk of recurrence or progression as determined by an immune context score (optionally in combination with other diagnostic criteria), the neoadjuvant or adjuvant treatment course does not include chemotherapy and does not include radiation therapy.

In each case, the treatment course may further comprise hormone therapy for ER-positive or PR-positive tumors, and/or HER2-directed therapy for HER2-positive tumors.

For stage IV cancers, the primary treatment course is by radiation therapy, chemotherapy, hormone therapy, and/or HER2-directed therapy, although surgical removal of the tumor(s) or breast is done whenever possible. In this case, the immune context score may be used to determine whether or not to administer chemotherapy or radiation therapy as part of the treatment course. In one specific non-limiting embodiment, a treatment course is selected for a stage IV invasive breast tumor, wherein:

for subjects having a good prognosis as determined by an immune context score (optionally in combination with other diagnostic criteria), the treatment course comprises chemotherapy and/or radiation therapy; or for subjects having a poor prognosis as determined by an immune context score (optionally in combination with other diagnostic criteria), the treatment course does not include chemotherapy and does not include radiation therapy.

In each case, the treatment course may further comprise surgical removal of tumor(s), hormone therapy, HER2-directed therapy, and/or palliative therapy.

IV.A.3. Melanoma

In an embodiment, a continuous scoring function is developed for a melanoma as a function of patient prognosis, and the output of the continuous scoring function is used to determine a course of treatment for the patient. In a specific embodiment, the continuous scoring function uses a normalized CD3 density and a normalized CD8 density, each density obtained from a peri-tumoral region, from an IM region, or from an IM and a TC region. In an embodiment, each normalized density is a global normalized metric. In an embodiment, the continuous scoring function is prognostic of 3 year recurrence-free survival. In another embodiment, the continuous scoring function is prognostic of 3 year progression-free survival. In another embodiment, the continuous scoring function is prognostic of 3 year overall survival. In another embodiment, the continuous scoring function is prognostic of 3 year disease-specific survival.

For stage 0 melanomas, the primary treatment typically is surgical excision of the tumor (often accompanied by a margin of normal skin), and optionally including innate immune system (IIS)-activating therapies (such as imiquimod, a TLR7-activating small molecule) and/or radiation, although in some instances an IIS-activating therapy and/or radiation may be done instead of surgery. In an embodiment, the immune context score is used to determine whether or not to use radiation therapy in an adjuvant setting. In one specific non-limiting embodiment, a treatment course for a stage 0 melanoma is selected wherein:

for subjects having a high risk of recurrence or progression as determined by an immune context score (optionally in combination with other diagnostic criteria), an adjuvant treatment course is selected that includes radiation; or for subjects having a low risk of recurrence or progression as determined by an immune context score (optionally in combination with other diagnostic criteria), a neoadjuvant or adjuvant treatment course that does not include radiation therapy.

In each case, the treatment course may further comprise an IIS-activating therapy. In another embodiment, the immune context score is used to determine whether to use an IIS-activating therapy. In one specific non-limiting embodiment, a treatment course for a stage 0 melanoma is selected wherein:

for subjects having a high risk of recurrence or progression as determined by an immune context score (optionally in combination with other diagnostic criteria), the treatment course comprises surgically excision of the melanoma, and adjuvant IIS-activating therapy; or for subjects having a low risk of recurrence or progression as determined by an immune context score (optionally in combination with other diagnostic criteria), the treatment course comprises surgical excision of the melanoma, optionally with IIS-activating therapy and/or radiation therapy.

For stage I and stage II melanomas, the primary treatment typically is surgical excision of the tumor (often accompanied by a margin of normal skin and surrounding lymph nodes), and optionally including adjuvant cytokine therapy (such as interferon-alpha or interleukin-2). In an embodiment, the immune context score is used to determine whether or not to use a cytokine therapy. In one specific non-limiting embodiment, a treatment course for a stage I or stage II melanoma is selected wherein:

for subjects having a high risk of recurrence or progression as determined by an immune context score (optionally in combination with other diagnostic criteria), an adjuvant treatment course is selected that includes adjuvant cytokine therapy; or for subjects having a low risk of recurrence or progression as determined by an immune context score (optionally in combination with other diagnostic criteria), an adjuvant cytokine therapy is not administered.

In each case, the treatment course may further comprise an immunotherapy (such as an IIS-activating therapy, a checkpoint inhibitor therapy, an oncolytic virus therapy, or a Bacille Calmette-Guerin (BCG) vaccine) and/or a targeted therapy, including BRAF inhibitors (such as vemurafenib, dabrafenib, trametinib, and cobimetinib) and c-Kit inhibitors (such as imatinib and nilotinib).

For stage III, the primary treatment typically is surgical excision of the tumor (often accompanied by a margin of normal skin), optionally including adjuvant cytokine therapy, radiation therapy, immunotherapy, targeted therapy (such as BRAF inhibitors and/or c-Kit inhibitors), and/or chemotherapy (including: alkylating agents, such as dacarbazine and temozolomide; platinum-based chemotherapeutics such as cisplatin and carboplatin; and cytoskeletal drugs, such as vinblastine and paclitaxel). In an embodiment, the immune context score is used to determine whether or not to use a chemotherapy. In one specific non-limiting embodiment, a treatment course for a stage III melanoma is selected, wherein:

for subjects having a high risk of recurrence or progression or a poor prognosis as determined by an immune context score (optionally in combination with other diagnostic criteria), a treatment course is selected that includes a chemotherapy; or for subjects having a low risk of recurrence or progression or a good prognosis as determined by an immune context score (optionally in combination with other diagnostic criteria), a treatment course is selected that includes a chemotherapy.

In each case, the treatment course may further comprise adjuvant cytokine therapy, adjuvant immunotherapy (such as an IIS-activating therapy, a checkpoint inhibitor therapy, an oncolytic virus therapy, or a Bacille Calmette-Guerin (BCG) vaccine) and/or an adjuvant targeted therapy.

For stage IV, treatment typically includes one or more cytokine therapy, radiation therapy, immunotherapy, targeted therapy (such as BRAF inhibitors and/or c-Kit inhibitors), and/or chemotherapy (including: alkylating agents, such as dacarbazine and temozolomide; platinum-based chemotherapeutics such as cisplatin and carboplatin; and cytoskeletal drugs, such as vinblastine and paclitaxel), each with or without excision of the primary tumor and surgically-accessible metastases. In an embodiment, the immune context score is used to determine whether or not to include a chemotherapy or radiation therapy. In one specific non-limiting embodiment, a treatment course for a stage IV melanoma is selected, wherein:

for subjects having a poor prognosis as determined by an immune context score (optionally in combination with other diagnostic criteria), a treatment course is selected that does not include a chemotherapy and does not include a radiation therapy; or for subjects having a good prognosis as determined by an immune context score (optionally in combination with other diagnostic criteria), a treatment course is selected that includes a chemotherapy.

In each case, the treatment course may further comprise surgery, cytokine therapy, immunotherapy (such as an IIS-activating therapy, a checkpoint inhibitor therapy, an oncolytic virus therapy, or a Bacille Calmette-Guerin (BCG) vaccine), a targeted therapy, and/or a palliative therapy.

IV.B. Immune Context Scoring Systems

In an embodiment, an immune context scoring system is provided, the immune context scoring system adapted for calculating on an immune context score from one or more digital images of a test sample stained for one or more immunological markers, the one or more immunological markers including at least one immune cell marker. An exemplary immune context scoring system is illustrated at FIG. 2.

The immune context scoring system includes an image analysis system 100. Image analysis system 100 may include one or more computing devices such as desktop computers, laptop computers, tablets, smartphones, servers, application-specific computing devices, or any other type(s) of electronic device(s) capable of performing the techniques and operations described herein. In some embodiments, image analysis system 100 may be implemented as a single device. In other embodiments, image analysis system 100 may be implemented as a combination of two or more devices together achieving the various functionalities discussed herein. For example, image analysis system 100 may include one or more server computers and a one or more client computers communicatively coupled to each other via one or more local-area networks and/or wide-area networks such as the Internet.

Figure 2:
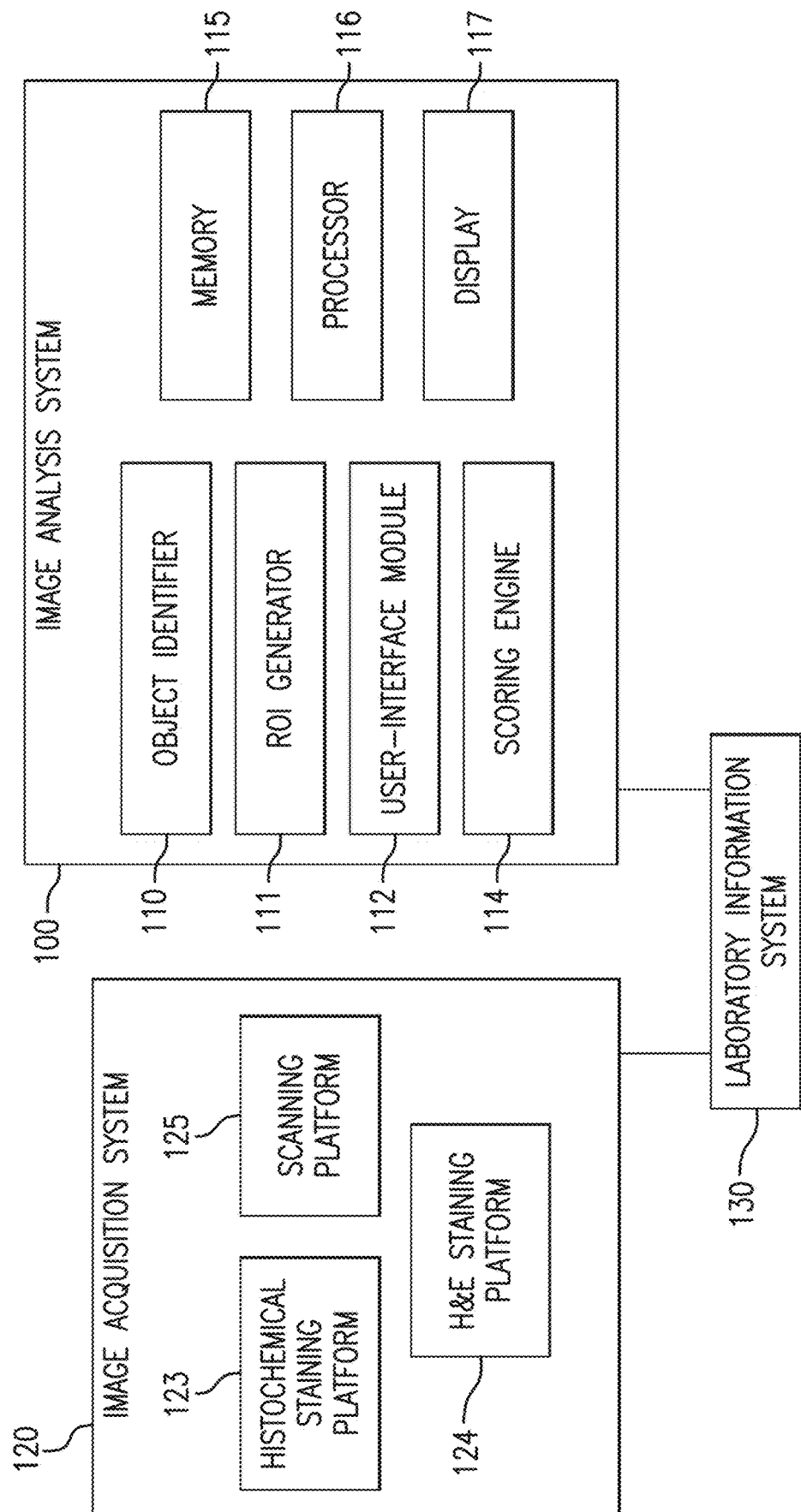
FIG. 2 illustrates an exemplary immune context scoring systems as disclosed herein.

As illustrated in FIG. 2, image analysis system 100 may include a memory 116, a processor 117, and a display 118. Memory 116 may include any combination of any type of volatile or non-volatile memories, such as random-access memories (RAMs), read-only memories such as an Electrically-Erasable Programmable Read-Only Memory (EEPROM), flash memories, hard drives, solid state drives, optical discs, and the like. For brevity purposes memory 116 is depicted in FIG. 2 as a single device, but it is appreciated that memory 116 can also be distributed across two or more devices.

Processor 117 may include one or more processors of any type, such as central processing units (CPUs), graphics processing units (GPUs), special-purpose signal or image processors, field-programmable gate arrays (FPGAs), tensor processing units (TPUs), and so forth. For brevity purposes processor 117 is depicted in FIG. 2 as a single device, but it is appreciated that processor 117 can also be distributed across any number of devices.

Display 118 may be implemented using any suitable technology, such as LCD, LED, OLED, TFT, Plasma, etc. In some implementations, display 118 may be a touch-sensitive display (a touchscreen).

As illustrated in FIG. 2, image analysis system 100 may also include an object identifier 110, a region of interest (ROI) generator 111, a user-interface module 112, and a scoring engine 114. While these modules are depicted in FIG. 2 as standalone modules, it will be evident to persons having ordinary skill in the art that each module may instead be implemented as a number of sub-modules, and that in some embodiments any two or more modules can be combined into a single module. Furthermore, in some embodiments, system 100 may include additional engines and modules (e.g., input devices, networking and communication modules, etc.) not depicted in FIG. 2 for brevity. Furthermore, in some embodiments, some of the blocks depicted in FIG. 2 may be disabled or omitted. As will be discussed in more detail below, the functionality of some or all modules of system 100 can be implemented in hardware, software, firmware, or as any combination thereof. Exemplary commercially-available software packages useful in implementing modules as disclosed herein include VENTANA VIRTUOSO; Definiens TISSUE STUDIO, DEVELOPER XD, and IMAGE MINER; and Visopharm BIOTOPIX, ONCOTOPIX, and STEREOTOPIX software packages.

After acquiring the image, image analysis system 100 may pass the image to an object identifier 110, which functions to identify and mark relevant objects and other features within the image that will later be used for scoring. Object identifier 110 may extract from (or generate for) each image a plurality of image features characterizing the various objects in the image as a well as pixels representing expression of the biomarker(s). The extracted image features may include, for example, texture features such as Haralick features, bag-of-words features and the like. The values of the plurality of image features may be combined into a high-dimensional vector, hereinafter referred to as the "feature vector" characterizing the expression of the biomarker. For example, if M features are extracted for each object and/or pixel, each object and/or pixel can be characterized by an M-dimensional feature vector. The output of object identifier 110 is effectively a map of the image annotating the position of objects and pixels of interest and associating those objects and pixels with a feature vector describing the object or pixels.

For biomarkers that are scored on the basis of the biomarker's association with a particular type of object (such as membranes, nuclei, cells, etc.), the features extracted by object identifier 110 may include features or feature vectors sufficient to categorize the objects in the sample as biomarker-positive objects of interest or biomarker-negative markers of interest and/or by level or intensity of biomarker staining of the object. In cases where the biomarker may be weighted differently depending on the object type that is expressing it (such as immune escape biomarkers such as PD-L1, which can be scored on the basis of tumor cell expression, immune cell expression, or both), the features extracted by object identifier 110 may include features relevant to determining the type of objects associated with biomarker-positive pixels. Thus, the objects may then be categorized at least on the basis of biomarker expression (for example, biomarker-positive or biomarker-negative cells) and, if relevant, a sub-type of the object (e.g. tumor cell, immune cell, etc.). In cases where extent of biomarker-expression is scored regardless of association with objects, the features extracted by object identifier 110 may include for example location and/or intensity of biomarker-positive pixels. The precise features extracted from the image will depend on the type of classification function being applied, and would be well-known to a person of ordinary skill in the art.

An example of objects identified for certain immunological biomarkers is set forth below in Table 6:

TABLE 6

| Biomarker | Object(s) |
| --- | --- |
| CD3 | CD3$^+$ cells |
| CD8 | CD8$^+$ cells, and/or |
| | CD8$^-$ immune cells, and/or |
| | CD8−/CD3+ cells |
| FoxP3 | FoxP3$^+$ cells, and/or |
| | CD3$^+$/FoxP3$^+$ cells, and/or |
| | CD3$^+$/FoxP3$^-$ cells |
| PD-L1 | PD-L1+ pixels, and/or |
| | PD-L1+ membrane, and/or |
| | PD-L1+ cells, |
| | PD-L1+ tumor cells, and/or |
| | PD-L1+ immune cells |

The image analysis system 100 may also pass the image to ROI generator 111. ROI generator 111 is used to identify the ROI or ROIs of the image from which the immune context score will be calculated. In cases where the object identifier 110 is not applied to the whole image, the ROI or ROIs generated by the ROI generator 111 may also be used to define a subset of the image on which object identifier 110 is executed.

In one embodiment, ROI generator 111 may be accessed through user-interface module 112. An image of the biomarker-stained sample (or a morphologically-stained serial section of the biomarker-stained sample) is displayed on a graphic user interface of the user interface module 112, and the user annotates one or more region(s) in the image to be considered ROIs. ROI annotation can take a number of forms in this example. For example, the user may manually define the ROI (referred to hereafter as "manual ROI annotation"). In other examples, the ROI generator 111 may assist the user in annotating the ROI (termed, "semi-automated ROI annotation"). For example, the user may delineate one or more regions on the digital image, which the system then automatically transforms into a complete ROI. For example, if the desired ROI is an IM region, a user delineates the IM region, and the system identifies similar morphological regions by, for example, using computer vision and machine learning. As another example, the user could annotate an edge in the image (such as, for example, a leading edge of an invasive margin of a tumor, an edge denoting a transition from tumor core to invasive margin, or an edge denoting a center of the invasive margin), and ROI generator 111 may automatically define an ROI based on the user-defined edge. For example, the user may annotate the edge of the invasive margin or the whole tumor in user interface module 112, and the ROI generator 111 creates an ROI using the edge as a guide, for example, by drawing an ROI encompassing all objects within a predefined distance of the edge, or within a predefined distance of one side of the edge, or within a first predefined distance on a first side of the edge and within a second predefined distance on a second side of the edge. Thus, for example, a PT ROI could be annotated in a semi-automated manner by a method comprising:
 (a) a user annotates the IM in an H&E image of the sample in the user interface 112 by tracing or outlining the IM region; and
 (b) the ROI generator 111 automatically annotates an ROI encompassing the outlined IM region, and all points within a pre-defined distance of the outline of the IM region.

In another example, a PT ROI could be annotated in a semi-automated manner by a method comprising:
 (a) a user annotates the IM in an H&E image of the sample in the user interface 112 by outlining the IM region; and
 (b) the ROI generator 111 automatically identifies a line tracing a center line that bisects the outlined IM region across the length of the IM, and annotates an ROI encompassing all points within a pre-defined distance of the center line.

In another example, a PT ROI could be annotated in a semi-automated manner by a method comprising:
 (a) a user annotates an IM region in an H&E image of the sample in the user interface 112 by tracing one or more edges of the IM region, such as an edge separating the IM region from an extra-tumoral region, an edge defining a center line bisecting the IM region lengthwise, and/or an edge separating the TC and IM regions; and
 (b) the ROI generator 111 automatically identifies annotates an ROI including all points within a pre-determined distance of the user-annotated edge(s).

In another example, an IM ROI could be annotated in a semi-automated manner by a method comprising:
 (a) a user annotates the IM in an H&E image of the sample in the user interface 112 by outlining the IM region; and
 (b) the ROI generator 111 automatically identifies regions outside of the user-annotated ROI that are morphologically similar to the user-annotated ROI using computer vision and machine learning, and generates a composite ROI including both the user-annotated ROI and the automatically identified regions.

In another example, an IM ROI could be annotated in a semi-automated manner by a method comprising:
 (a) a user annotates an IM region in an H&E image of the sample in the user interface 112 by tracing one or more edges the IM region, such as an edge separating the IM region from an extra-tumoral region, an edge defining a center line bisecting the IM region lengthwise, and/or an edge separating the TC and IM regions; and (b) the ROI generator 111 automatically identifies annotates an ROI including all regions within a pre-determined distance of the user-annotated edge(s) that are morphologically similar using computer vision and machine learning.

In other embodiments, a PT ROI could be identified in a semi-automated manner by a user outlining the IM region, and the ROI generator 111 automatically expanding the outlined IM region to have a minimum width at all points. Many other arrangements could be used as well. In cases in which ROI generation is semi-automated, the user may be given an option to modify the ROI annotated by ROI generator 111, such as by expanding the ROI, annotating regions of the ROI or objects within the ROI to be excluded from analysis, etc.

In other embodiments, ROI generator 111 may automatically suggest an ROI without any direct input from the user (for example, by applying a tissue segmentation function to an unannotated image), which the user may then choose to accept, reject, or edit as appropriate.

In some embodiments, ROI generator 111 may also include a registration function, whereby an ROI annotated in one section of a set of serial sections is automatically transferred to other sections of the set of serial sections. This functionality is especially useful when there are multiple biomarkers being analyzed, or when an H&E-stained serial section is provided along with the biomarker-labeled sections.

Figure 3B:
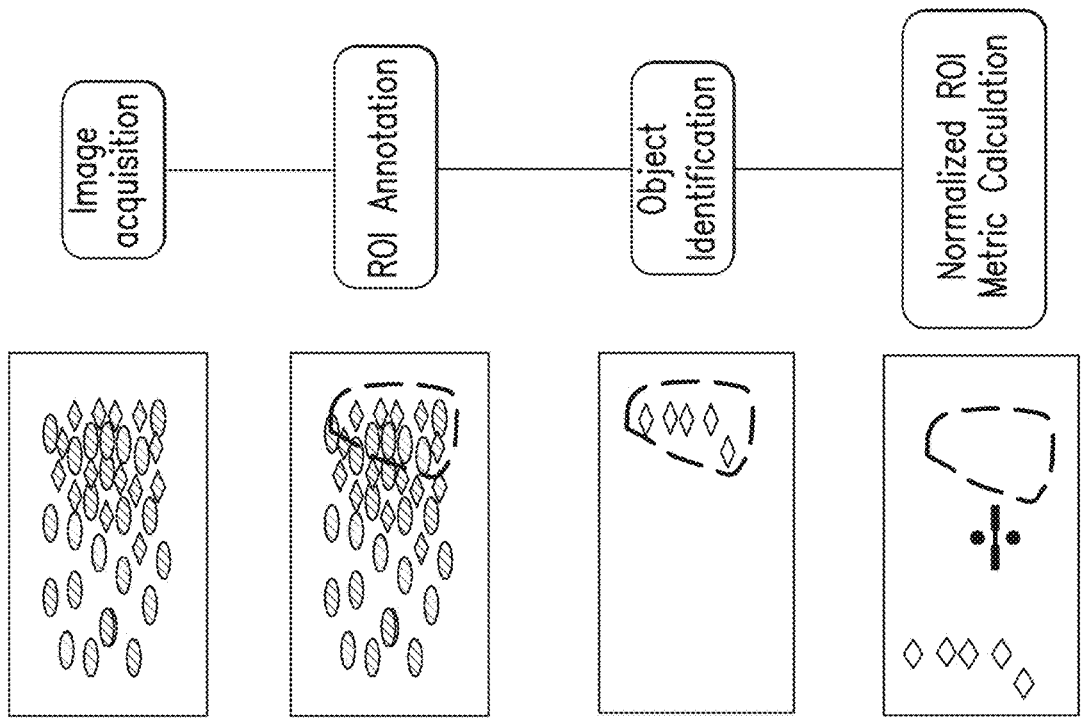
FIG. 3B illustrates an exemplary workflow implemented on an image analysis system as disclosed herein, wherein the object identification function is executed on only the ROI after the ROI generator function is executed.
Figure 3A:
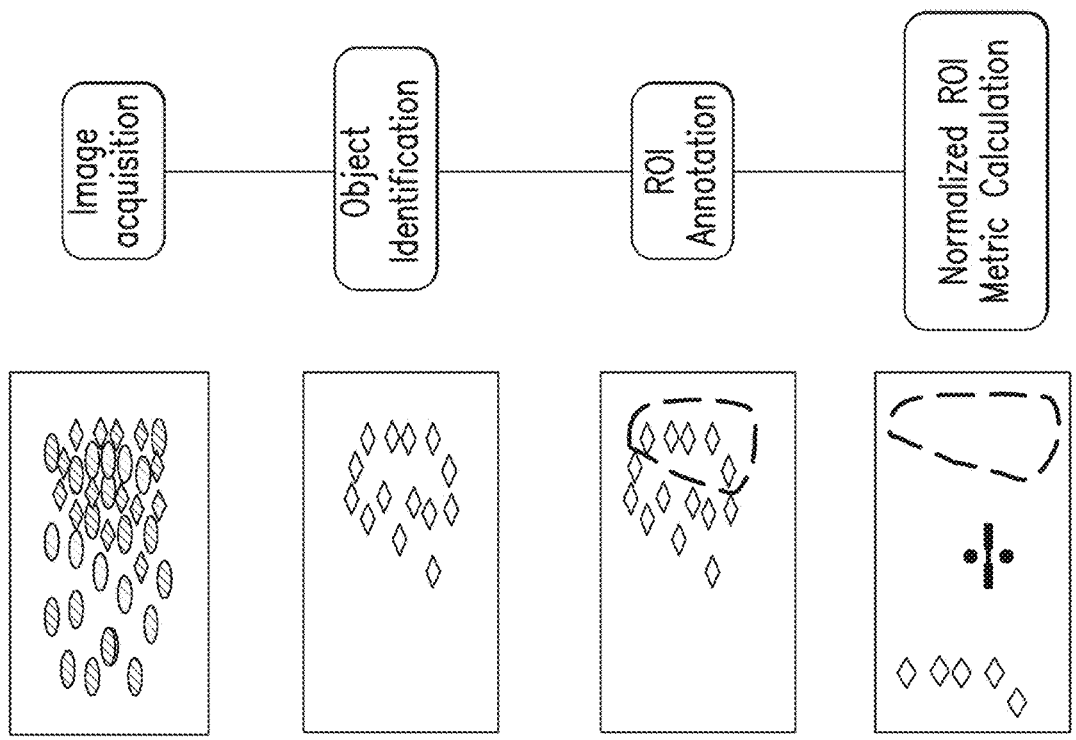
FIG. 3A illustrates an exemplary workflow implemented on an image analysis system as disclosed herein, wherein the object identification function is executed on the whole image before the ROI generator function is executed.

The object identifier 110 and the ROI generator 111 may be implemented in any order. For example, the object identifier 110 may be applied to the entire image first. The positions and features of the identified objects can then be stored and recalled later when the ROI generator 111 is implemented. In such an arrangement, a score can be generated by the scoring engine 113 immediately upon generation of the ROI. Such a workflow is illustrated at FIG. 3A. As can be seen at FIG. 3A, an image is obtained having a mixture of different objects (illustrated by dark ovals and dark diamonds). After the object identification task is implemented, all diamonds in the image are identified (illustrated by open diamonds). When the ROI is appended to the image (illustrated by the dashed line), only the diamonds located in the ROI region are included in the metric calculation for the ROI. A feature vector is then calculated including the feature metric and any additional metrics used by a continuous scoring function as described below. Alternatively, the ROI generator 111 can be implemented first. In this work flow, the object identifier 110 may be implemented only on the ROI (which minimizes computation time), or it may still be implemented on the whole image (which would allow on-the-fly adjustments without re-running the object identifier 110). Such a workflow is illustrated at FIG. 3B. As can be seen at FIG. 3B, an image is obtained having a mixture of different objects (illustrated by dark ovals and dark diamonds). The ROI is appended to the image (illustrated by the dashed line), but no objects have been marked yet. After the object identification task is implemented on the ROI, all diamonds in the ROI are identified (illustrated by open diamonds) and included in the feature metric calculation for the ROI. A feature vector is then calculated including the feature metric(s) and any additional metrics used by the continuous scoring function. It may also be possible to implement the object identifier 110 and ROI generator 111 simultaneously.

After both the object identifier 110 and ROI generator 111 have been implemented, a scoring engine 112 is implemented. The scoring engine 112 calculates feature metric(s) for the ROI from at least one ROI metric (such as ROI area or linear length of an ROI edge), relevant metrics for objects in the ROI (such as number of marker-positive objects), and, if being used, pre-determined maximum and/or minimum cutoffs and/or normalization factors. Where the feature metric is a global metric, the scoring engine 112 may also include a function that overlays a plurality of control regions in the ROI for calculating the CR metric. A ROI feature vector including the calculated feature metrics and any other variable derived from the ROI used by the continuous scoring function, and applies the continuous scoring function to the ROI feature vector.

Examples of ROI(s) and feature vectors associated with specific biomarker panels are listed at Table 7:

TABLE 7

| Panel | ROI | Feature metrics |
| --- | --- | --- |
| CD3 | TC region | CD3+ cell density |
| CD3 | IM region | CD3+ cell density |
| CD3 | PT region | CD3+ cell density |
| CD3 | TC region | CD3+ cell density in TC region |
|  | IM region | CD3+ cell density in IM region |
| CD3 | TC region | CD3+ cell density in TC region |
|  | PT region | CD3+ cell density in PT region |
| CD3 + CD8 | TC region | CD3+ cell density |
|  |  | CD8+ cell density |
| CD3 + CD8 | PT region | CD3+ cell density |
|  |  | CD8+ cell density |
| CD3 + CD8 | IM region | CD3+ cell density |
|  |  | CD8+ cell density |
| CD3 + CD8 | WT region | CD3+ cell density |
|  |  | CD8+ cell density |
| CD3 + CD8 | 1. IM region | CD3+ cell density from IM region |
|  | 2. TC region | CD8+ cell density from IM region |
|  |  | CD3+ cell density from TC region |
|  |  | CD8+ cell density from TC region |
| CD3 + CD8 | 1. PT region | CD3+ cell density from PT region |
|  | 2. TC region | CD8+ cell density from PT region |
|  |  | CD3+ cell density from TC region |
|  |  | CD8+ cell density from TC region |
| CD3 + CD8 | 1. PT region | CD3-rich area ratio (area of CD3-rich region |
|  | 2. CD3-rich region(s) | relative to area of PT region) |
|  | within PT region | CD8+ cell density within CD3-rich regions |

TABLE 7-continued

| Panel | ROI | Feature metrics |
|---|---|---|
| CD3 + CD8 | 1. IM region<br>2. CD3-rich region(s) within IM region | CD3-rich area ratio (area of CD3-rich region relative to area of IM region)<br>CD8+ cell density within CD3-rich regions |
| CD3 + CD8 | 1. WT region<br>2. CD3-rich region(s) within WT region | CD3-rich area ratio (area of CD3-rich region relative to area of WT region)<br>CD8+ cell density within CD3-rich regions |
| CD3 + CD8 | 1. IM region<br>2. CD3-rich region(s) within IM region<br>3. TC region<br>4. CD3-rich region(s) within TC region | CD3-rich area ratio of IM (area of CD3-rich regions in IM relative to area of IM region)<br>CD8+ cell density within CD3-rich regions of IM<br>CD3-rich area ratio of TC (area of CD3-rich regions in TC relative to area of TC region)<br>CD8+ cell density within CD3-rich regions of TC |
| CD3 + CD8 | 1. PT region<br>2. CD3-rich region(s) within PT region<br>3. TC region<br>4. CD3-rich region(s) within TC region | CD3-rich area ratio of PT (area of CD3-rich regions in PT relative to area of PT region)<br>CD8+ cell density within CD3-rich regions of PT<br>CD3-rich area ratio of TC (area of CD3-rich regions in TC relative to area of TC region)<br>CD8+ cell density within CD3-rich regions of TC |
| CD3 + CD8 | 1. PT region<br>2. CD3-poor region(s) within PT region | CD3-poor area ratio (area of CD3-poor region relative to area of PT region)<br>CD8+ cell density within CD3-poor regions |
| CD3 + CD8 | 1. IM region<br>2. CD3-poor region(s) within IM region | CD3-poor area ratio (area of CD3-poor region relative to area of IM region)<br>CD8+ cell density within CD3-poor regions |
| CD3 + CD8 | 1. WT region<br>2. CD3-poor region(s) within WT region | CD3-poor area ratio (area of CD3-poor region relative to area of WT region)<br>CD8+ cell density within CD3-rpoor regions |
| CD3 + CD8 | 1. IM region<br>2. CD3-poor region(s) within IM region<br>3. TC region<br>4. CD3-poor region(s) within TC region | CD3-poor area ratio of IM (area of CD3-poor regions in IM relative to area of IM region)<br>CD8+ cell density within CD3-poor regions of IM<br>CD3-poor area ratio of TC (area of CD3-poor regions in TC relative to area of TC region)<br>CD8+ cell density within CD3-poor regions of TC |
| CD3 + CD8 | 1. PT region<br>2. CD3-poor region(s) within PT region<br>3. TC region<br>4. CD3-poor region(s) within TC region | CD3-poor area ratio of PT (area of CD3-poor regions in PT relative to area of PT region)<br>CD8+ cell density within CD3-poor regions of PT<br>CD3-poor area ratio of TC (area of CD3-poor regions in TC relative to area of TC region)<br>CD8+ cell density within CD3-poor regions of TC |
| CD3 + CD4 | PT region | CD3+ cell density<br>CD4+ cell density |
| CD3 + CD4 | IM region | CD3+ cell density<br>CD4+ cell density |
| CD3 + CD4 | WT region | CD3+ cell density<br>CD4+ cell density |
| CD3 + CD4 | 1. IM region<br>2. TC region | CD3+ cell density from IM region<br>CD4+ cell density from IM region<br>CD3+ cell density from TC region<br>CD4+ cell density from TC region |
| CD3 + CD4 | 1. PT region<br>2. TC region | CD3+ cell density from PT region<br>CD4+ cell density from PT region<br>CD3+ cell density from TC region<br>CD4+ cell density from TC region |
| CD3 + CD4 | 1. PT region<br>2. CD3-rich region(s) within PT region | CD3-rich area ratio (area of CD3-rich region relative to area of PT region)<br>CD4+ cell density within CD3-rich regions |
| CD3 + CD4 | 1. IM region<br>2. CD3-rich region(s) within IM region | CD3-rich area ratio (area of CD3-rich region relative to area of IM region)<br>CD4+ cell density within CD3-rich regions |
| CD3 + CD4 | 1. WT region<br>2. CD3-rich region(s) within WT region | CD3-rich area ratio (area of CD3-rich region relative to area of WT region)<br>CD4+ cell density within CD3-rich regions |
| CD3 + CD4 | 1. IM region<br>2. CD3-rich region(s) within IM region<br>3. TC region<br>4. CD3-rich region(s) within TC region | CD3-rich area ratio of IM (area of CD3-rich regions in IM relative to area of IM region)<br>CD4+ cell density within CD3-rich regions of IM<br>CD3-rich area ratio of TC (area of CD3-rich regions in TC relative to area of TC region)<br>CD4+ cell density within CD3-rich regions of TC |
| CD3 + CD4 | 1. PT region<br>2. CD3-rich region(s) within IM region<br>3. TC region<br>4. CD3-rich region(s) within TC region | CD3-rich area ratio of PT (area of CD3-rich regions in PT relative to area of IM region)<br>CD4+ cell density within CD3-rich regions of IM<br>CD3-rich area ratio of TC (area of CD3-rich regions in TC relative to area of TC region)<br>CD4+ cell density within CD3-rich regions of TC |
| CD3 + CD4 | 1. PT region<br>2. CD3-poor region(s) within PT region | CD3-poor area ratio (area of CD3-poor region relative to area of PT region)<br>CD4+ cell density within CD3-poor regions |

TABLE 7-continued

| Panel | ROI | Feature metrics |
|---|---|---|
| CD3 + CD4 | 1. IM region<br>2. CD3-poor region(s) within IM region | CD3-poor area ratio (area of CD3-poor region relative to area of IM region)<br>CD4+ cell density within CD3-poor regions |
| CD3 + CD4 | 1. WT region<br>2. CD3-poor region(s) within WT region | CD3-rich area ratio (area of CD3-poor region relative to area of WT region)<br>CD4+ cell density within CD3-poor regions |
| CD3 + CD4 | 1. IM region<br>2. CD3-poor region(s) within IM region<br>3. TC region<br>4. CD3-poor region(s) within TC region | CD3-poor area ratio of IM (area of CD3-poor regions in IM relative to area of IM region)<br>CD4+ cell density within CD3-poor regions of IM<br>CD3-poor area ratio of TC (area of CD3-poor regions in TC relative to area of TC region)<br>CD4+ cell density within CD3-poor regions of TC |
| CD3 + CD4 | 1. PT region<br>2. CD3-poor region(s) within IM region<br>3. TC region<br>4. CD3-poor region(s) within TC region | CD3-poor area ratio of PT (area of CD3-poor regions in PT relative to area of IM region)<br>CD4+ cell density within CD3-poor regions of IM<br>CD3-poor area ratio of TC (area of CD3-poor regions in TC relative to area of TC region)<br>CD4+ cell density within CD3-poor regions of TC |
| CD3 + CD45RA | PT region | CD3+ cell density<br>CD45RA+ cell density |
| CD3 + CD45RA | IM region | CD3+ cell density<br>CD45RA+ cell density |
| CD3 + CD45RA | WT region | CD3+ cell density<br>CD45RA+ cell density |
| CD3 + CD45RA | 1. IM region<br>2. TC region | CD3+ cell density from IM region<br>CD45RA+ cell density from IM region<br>CD3+ cell density from TC region<br>CD45RA+ cell density from TC region |
| CD3 + CD45RA | 1. PT region<br>2. TC region | CD3+ cell density from PT region<br>CD45RA+ cell density from PT region<br>CD3+ cell density from TC region<br>CD45RA+ cell density from TC region |
| CD3 + CD45RA | 1. PT region<br>2. CD3-rich region(s) within PT region | CD3-rich area ratio (area of CD3-rich region relative to area of PT region)<br>CD45RA+ cell density within CD3-rich regions |
| CD3 + CD45RA | 1. IM region<br>2. CD3-rich region(s) within IM region | CD3-rich area ratio (area of CD3-rich region relative to area of IM region)<br>CD45RA+ cell density within CD3-rich regions |
| CD3 + CD45RA | 1. WT region<br>2. CD3-rich region(s) within WT region | CD3-rich area ratio (area of CD3-rich region relative to area of WT region)<br>CD45RA+ cell density within CD3-rich regions |
| CD3 + CD45RA | 1. IM region<br>2. CD3-rich region(s) within IM region<br>3. TC region<br>4. CD3-rich region(s) within TC region | CD3-rich area ratio of IM (area of CD3-rich regions in IM relative to area of IM region)<br>CD45RA+ cell density within CD3-rich regions of IM<br>CD3-rich area ratio of TC (area of CD3-rich regions in TC relative to area of TC region)<br>CD45RA+ cell density within CD3-rich regions of TC |
| CD3 + CD45RA | 1. PT region<br>2. CD3-rich region(s) within PT region<br>3. TC region<br>4. CD3-rich region(s) within TC region | CD3-rich area ratio of PT (area of CD3-rich regions in PT relative to area of PT region)<br>CD45RA+ cell density within CD3-rich regions of PT<br>CD3-rich area ratio of TC (area of CD3-rich regions in TC relative to area of TC region)<br>CD45RA+ cell density within CD3-rich regions of TC |
| CD3 + CD45RA | 1. PT region<br>2. CD3-poor region(s) within PT region | CD3-poor area ratio (area of CD3-poor region relative to area of PT region)<br>CD45RA+ cell density within CD3-poor regions |
| CD3 + CD45RA | 1. IM region<br>2. CD3-poor region(s) within IM region | CD3-poor area ratio (area of CD3-poor region relative to area of IM region)<br>CD45RA+ cell density within CD3-poor regions |
| CD3 + CD45RA | 1. WT region<br>2. CD3-poor region(s) within WT region | CD3-poor area ratio (area of CD3-poor region relative to area of WT region)<br>CD45RA+ cell density within CD3-poor regions |
| CD3 + CD45RA | 1. IM region<br>2. CD3-poor region(s) within IM region<br>3. TC region<br>4. CD3-poor region(s) within TC region | CD3-poor area ratio of IM (area of CD3-poor regions in IM relative to area of IM region)<br>CD45RA+ cell density within CD3-poor regions of IM<br>CD3-poor area ratio of TC (area of CD3-poor regions in TC relative to area of TC region)<br>CD45RA+ cell density within CD3-poor regions of TC |
| CD3 + CD45RA | 1. PT region<br>2. CD3-poor region(s) within PT region<br>3. TC region<br>4. CD3-poor region(s) within TC region | CD3-poor area ratio of PT (area of CD3-poor regions in PT relative to area of PT region)<br>CD45RA+ cell density within CD3-poor regions of PT<br>CD3-poor area ratio of TC (area of CD3-poor regions in TC relative to area of TC region)<br>CD45RA+ cell density within CD3-poor regions of TC |
| CD3 + CD45RO | PT region | CD3+ cell density<br>CD45RO+ cell density |
| CD3 + CD45RO | IM region | CD3+ cell density<br>CD45RO+ cell density |

TABLE 7-continued

| Panel | ROI | Feature metrics |
|---|---|---|
| CD3 + CD45RO | WT region | CD3+ cell density |
| | | CD45RO+ cell density |
| CD3 + CD45RO | 1. IM region | CD3+ cell density from IM region |
| | 2. TC region | CD45RO+ cell density from IM region |
| | | CD3+ cell density from TC region |
| | | CD45RO+ cell density from TC region |
| CD3 + CD45RO | 1. PT region | CD3+ cell density from PT region |
| | 2. TC region | CD45RO+ cell density from PT region |
| | | CD3+ cell density from TC region |
| | | CD45RO+ cell density from TC region |
| CD3 + CD45RO | 1. PT region | CD3-rich area ratio (area of CD3-rich region |
| | 2. CD3-rich region(s) | relative to area of PT region) |
| | within PT region | CD45RO+ cell density within CD3-rich regions |
| CD3 + CD45RO | 1. IM region | CD3-rich area ratio (area of CD3-rich region |
| | 2. CD3-rich region(s) | relative to area of IM region) |
| | within IM region | CD45RO+ cell density within CD3-rich regions |
| CD3 + CD45RO | 1. WT region | CD3-rich area ratio (area of CD3-rich region |
| | 2. CD3-rich region(s) | relative to area of WT region) |
| | within WT region | CD45RO+ cell density within CD3-rich regions |
| CD3 + CD45RO | 1. IM region | CD3-rich area ratio of IM (area of CD3-rich |
| | 2. CD3-rich region(s) | regions in IM relative to area of IM region) |
| | within IM region | CD45RO+ cell density within CD3-rich regions of IM |
| | 3. TC region | CD3-rich area ratio of TC (area of CD3-rich |
| | 4. CD3-rich region(s) | regions in TC relative to area of TC region) |
| | within TC region | CD45RO+ cell density within CD3-rich regions of TC |
| CD3 + CD45RO | 1. PT region | CD3-rich area ratio of PT (area of CD3-rich |
| | 2. CD3-rich region(s) | regions in PT relative to area of IM region) |
| | within IM region | CD45RO+ cell density within CD3-rich regions of PT |
| | 3. TC region | CD3-rich area ratio of TC (area of CD3-rich |
| | 4. CD3-rich region(s) | regions in TC relative to area of TC region) |
| | within TC region | CD45RO+ cell density within CD3-rich regions of TC |
| CD3 + CD45RO | 1. PT region | CD3-poor area ratio (area of CD3-poor region |
| | 2. CD3-poor region(s) | relative to area of PT region) |
| | within PT region | CD45RO+ cell density within CD3-poor regions |
| CD3 + CD45RO | 1. IM region | CD3-poor area ratio (area of CD3-poor region |
| | 2. CD3-poor region(s) | relative to area of IM region) |
| | within IM region | CD45RO+ cell density within CD3-poor regions |
| CD3 + CD45RO | 1. WT region | CD3-poor area ratio (area of CD3-poor region |
| | 2. CD3-poor region(s) | relative to area of WT region) |
| | within WT region | CD45RO+ cell density within CD3-poor regions |
| CD3 + CD45RO | 1. IM region | CD3-poor area ratio of IM (area of CD3-poor |
| | 2. CD3-poor region(s) | regions in IM relative to area of IM region) |
| | within IM region | CD45RO+ cell density within CD3-poor regions of IM |
| | 3. TC region | CD3-poor area ratio of TC (area of CD3-poor |
| | 4. CD3-poor region(s) | regions in TC relative to area of TC region) |
| | within TC region | CD45RO+ cell density within CD3-poor regions of TC |
| CD3 + CD45RO | 1. PT region | CD3-poor area ratio of PT (area of CD3-poor |
| | 2. CD3-poor region(s) | regions in PT relative to area of IM region) |
| | within IM region | CD45RO+ cell density within CD3-poor regions of PT |
| | 3. TC region | CD3-poor area ratio of TC (area of CD3-poor |
| | 4. CD3-poor region(s) | regions in TC relative to area of TC region) |
| | within TC region | CD45RO+ cell density within CD3-poor regions of TC |
| CD3 + FOXP3 | PT region | CD3+ cell density |
| | | FOXP3+ cell density |
| CD3 + FOXP3 | IM region | CD3+ cell density |
| | | FOXP3+ cell density |
| CD3 + FOXP3 | WT region | CD3+ cell density |
| | | FOXP3+ cell density |
| CD3 + FOXP3 | 1. IM region | CD3+ cell density from IM region |
| | 2. TC region | FOXP3+ cell density from IM region |
| | | CD3+ cell density from TC region |
| | | FOXP3+ cell density from TC region |
| CD3 + FOXP3 | 1. PT region | CD3+ cell density from PT region |
| | 2. TC region | FOXP3+ cell density from PT region |
| | | CD3+ cell density from TC region |
| | | FOXP3+ cell density from TC region |
| CD3 + FOXP3 | 1. PT region | CD3-rich area ratio (area of CD3-rich region |
| | 2. CD3-rich region(s) | relative to area of PT region) |
| | within PT region | FOXP3+ cell density within CD3-rich regions |
| CD3 + FOXP3 | 1. IM region | CD3-rich area ratio (area of CD3-rich region |
| | 2. CD3-rich region(s) | relative to area of IM region) |
| | within IM region | FOXP3+ cell density within CD3-rich regions |
| CD3 + FOXP3 | 1. WT region | CD3-rich area ratio (area of CD3-rich region |
| | 2. CD3-rich region(s) | relative to area of WT region) |
| | within WT region | FOXP3+ cell density within CD3-rich regions |
| CD3 + FOXP3 | 1. IM region | CD3-rich area ratio of IM (area of CD3-rich |
| | 2. CD3-rich region(s) | regions in IM relative to area of IM region) |
| | within IM region | FOXP3+ cell density within CD3-rich regions of IM |

TABLE 7-continued

| Panel | ROI | Feature metrics |
|---|---|---|
| | 3. TC region | CD3-rich area ratio of TC (area of CD3-rich |
| | 4. CD3-rich region(s) | regions in TC relative to area of TC region) |
| | within TC region | FOXP3+ cell density within CD3-rich regions of TC |
| CD3 + FOXP3 | 1. PT region | CD3-rich area ratio of PT (area of CD3-rich |
| | 2. CD3-rich region(s) | regions in PT relative to area of PT region) |
| | within PT region | FOXP3+ cell density within CD3-rich regions of PT |
| | 3. TC region | CD3-rich area ratio of TC (area of CD3-rich |
| | 4. CD3-rich region(s) | regions in TC relative to area of TC region) |
| | within TC region | FOXP3+ cell density within CD3-rich regions of TC |
| CD3 + FOXP3 | 1. PT region | CD3-poor area ratio (area of CD3-poor region |
| | 2. CD3-poor region(s) | relative to area of PT region) |
| | within PT region | FOXP3+ cell density within CD3-poor regions |
| CD3 + FOXP3 | 1. IM region | CD3-poor area ratio (area of CD3-poor region |
| | 2. CD3-poor region(s) | relative to area of IM region) |
| | within IM region | FOXP3+ cell density within CD3-poor regions |
| CD3 + FOXP3 | 1. WT region | CD3-poor area ratio (area of CD3-poor region |
| | 2. CD3-poor region(s) | relative to area of WT region) |
| | within WT region | FOXP3+ cell density within CD3-poor regions |
| CD3 + FOXP3 | 1. IM region | CD3-poor area ratio of IM (area of CD3-poor |
| | 2. CD3-poor region(s) | regions in IM relative to area of IM region) |
| | within IM region | FOXP3+ cell density within CD3-poor regions of IM |
| | 3. TC region | CD3-poor area ratio of TC (area of CD3-poor |
| | 4. CD3-poor region(s) | regions in TC relative to area of TC region) |
| | within TC region | FOXP3+ cell density within CD3-poor regions of TC |
| CD3 + FOXP3 | 1. PT region | CD3-poor area ratio of PT (area of CD3-poor |
| | 2. CD3-poor region(s) | regions in PT relative to area of PT region) |
| | within PT region | FOXP3+ cell density within CD3-poor regions of PT |
| | 3. TC region | CD3-poor area ratio of TC (area of CD3-poor |
| | 4. CD3-poor region(s) | regions in TC relative to area of TC region) |
| | within TC region | FOXP3+ cell density within CD3-poor regions of TC |

The densities listed in Table 7 may in each case be a total metric or a global metric, and may in each case be an area density (i.e. number of positive cells over area of the ROI) or a linear density (i.e. number of positive cells over a linear length metric of the ROI, such as an edge length, a circumference, etc.). In each of these examples, the CD3-cells may be replaced with immune cells identified in an H&E-stained slide. All of the metrics listed in the "Feature vector" column of Table 7 may be normalized and/or subject to upper and/or lower limits, if desired. As used in this Table 7, a "CD3-rich region" is a region having an area above a threshold area with a density of CD3+ cells (or total lymphocytes as identified by H&E stain) above a threshold density. As used in this Table 7, a "CD3-poor region" is a region having an area above a threshold area with a density of CD3+ cells (or total lymphocytes as identified by H&E stain) below a threshold density.

As depicted in FIG. 2, in some embodiments image analysis system 100 may be communicatively coupled to an image acquisition system 120. Image acquisition system 120 may obtain images of samples and provide those images to image analysis system 100 for analysis and presentation to the user.

Figure 4:
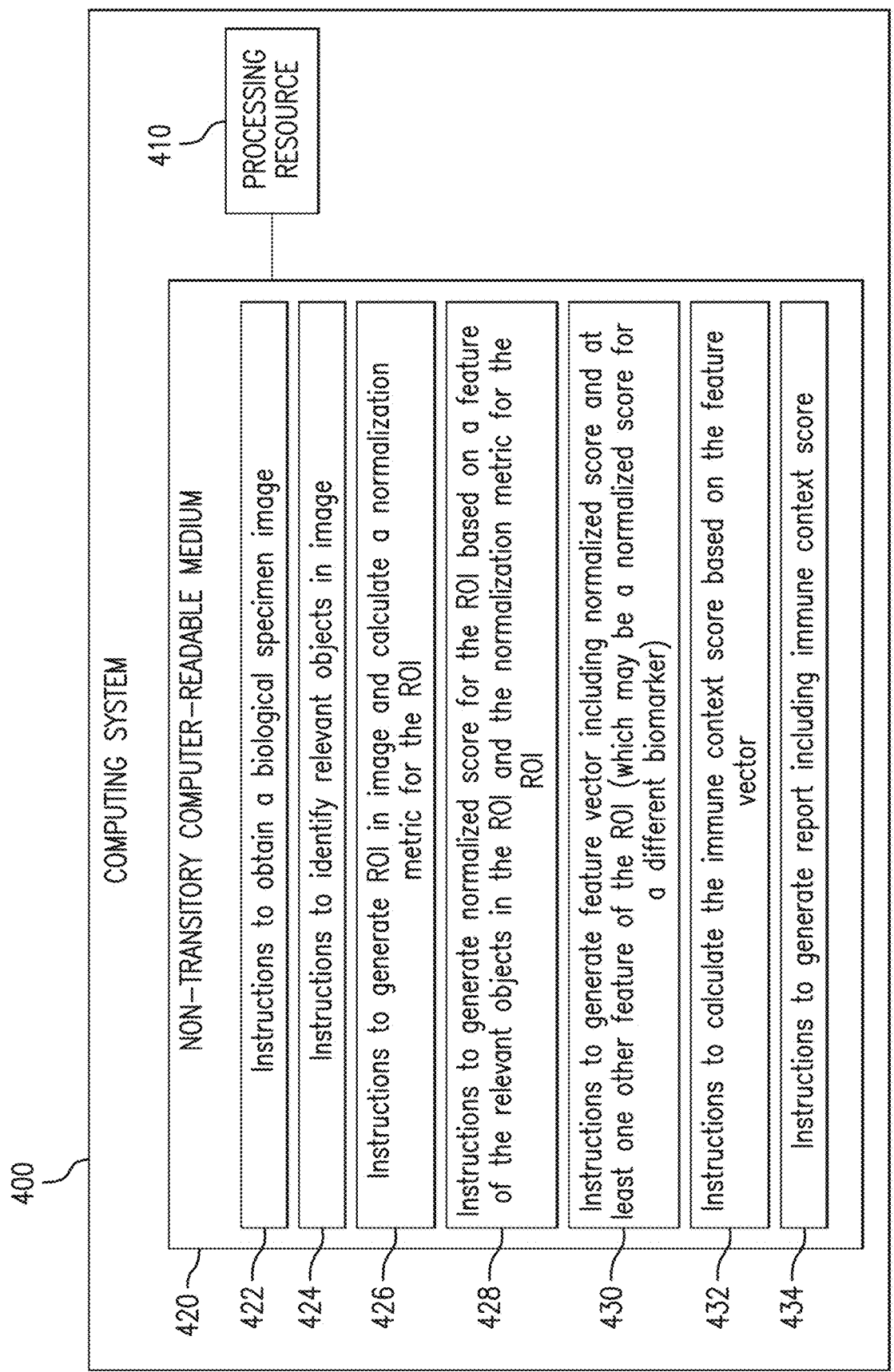
FIG. 4 illustrates an exemplary computing system that may form part of an image analysis system as disclosed herein.

As illustrated in FIG. 4, the image analysis system may include a computing system 400 for implementing the various functions, the computing system 400 comprising a processing resource 410 and a non-transitory computer readable medium 420. The non-transitory computer readable medium 420 includes, for example, instructions to execute function(s) that: obtain a biological specimen image 422; identify relevant objects in the image 424; generate an ROI in the image 426; calculate an ROI metric for the ROI 426; generate a feature metric based on the relevant objects in the ROI, the ROI metric 428, and other optional factors being used, such as normalization factors and/or maximum and/or minimum feature values; generate a feature vector including the feature metric and at least one other feature metric of the sample (which may be, for example, an additional feature metric for a different biomarker) 430; calculate immune context score based on the feature vector 432; and generate a report including the immune context score 434.

Image acquisition system 120 may also include a scanning platform 125 such as a slide scanner that can scan the stained slides at 20×, 40×, or other magnifications to produce high resolution whole-slide digital images, including for example slide scanners as discussed above at section IV. At a basic level, the typical slide scanner includes at least: (1) a microscope with lens objectives, (2) a light source (such as halogen, light emitting diode, white light, and/or multispectral light sources, depending on the dye), (3) robotics to move glass slides around (or to move the optics around the slide), (4) one or more digital cameras for image capture, (5) a computer and associated software to control the robotics and to manipulate, manage, and view digital slides. Digital data at a number of different X-Y locations (and in some cases, at multiple Z planes) on the slide are captured by the camera's charge-coupled device (CCD), and the images are joined together to form a composite image of the entire scanned surface. Common methods to accomplish this include:

(1) Tile based scanning, in which the slide stage or the optics are moved in very small increments to capture square image frames, which overlap adjacent squares to a slight degree. The captured squares are then automatically matched to one another to build the composite image; and (2) Line-based scanning, in which the slide stage moves in a single axis during acquisition to capture a number of composite image "strips." The image strips can then be matched with one another to form the larger composite image.

A detailed overview of various scanners (both fluorescent and brightfield) can be found at Farahani et al., Whole slide imaging in pathology: advantages, limitations, and emerging perspectives, Pathology and Laboratory Medicine Int'l, Vol. 7, p. 23-33 (June 2015), the content of which is incorporated by reference in its entirety. Examples of commercially available slide scanners include: 3DHISTECH PANNORAMIC SCAN II; DIGIPATH PATHSCOPE; HAMAMATSU NANOZOOMER RS, HT, and XR; HURON TISSUESCOPE 4000, 4000XT, and HS; LEICA SCANSCOPE AT, AT2, CS, FL, and SCN400; MIKROSCAN D2; OLYMPUS VS120-SL; OMNYX VL4, and VL120; PERKINELMER LAMINA; PHILIPS ULTRA-FAST SCANNER; SAKURA FINETEK VISIONTEK; UNIC PRECICE 500, and PRECICE 600X; VENTANA ISCAN COREO and ISCAN HT; and ZEISS AXIO SCAN.Z1. Other exemplary systems and features can be found in, for example, WO2011-049608) or in U.S. Patent Application No. 61/533,114, filed on Sep. 9, 2011, entitled IMAGING SYSTEMS, CASSETTES, AND METHODS OF USING THE SAME the content of which is incorporated by reference in its entirety.

Images generated by scanning platform 125 may be transferred to image analysis system 100 or to a server or database accessible by image analysis system 100. In some embodiments, the images may be transferred automatically via one or more local-area networks and/or wide-area networks. In some embodiments, image analysis system 100 may be integrated with or included in scanning platform 125 and/or other modules of image acquisition system 120, in which case the image may be transferred to image analysis system, (e.g., through a memory accessible by both platform 125 and system 120). In some embodiments, image acquisition system 120 may not be communicatively coupled to image analysis system 100, in which case the images may be stored on a non-volatile storage medium of any type (e.g., a flash drive) and downloaded from the medium to image analysis system 100 or to a server or database communicatively coupled thereto. In any of the above examples, image analysis system 100 may obtain an image of a biological sample, where the sample may have been affixed to a slide and stained by histochemical staining platform 123, and where the slide may have been scanned by a slide scanner or another type of scanning platform 125. It is appreciated, however, that in other embodiments, below-described techniques may also be applied to images of biological samples acquired and/or stained through other means.

Image acquisition system 120 may also include an automated histochemical staining platform 123, such as an automated IHC/ISH slide stainer. Automated IHC/ISH slide stainers typically include at least: reservoirs of the various reagents used in the staining protocols, a reagent dispense unit in fluid communication with the reservoirs for dispensing reagent onto a slide, a waste removal system for removing used reagents and other waste from the slide, and a control system that coordinates the actions of the reagent dispense unit and waste removal system. In addition to performing staining steps, many automated slide stainers can also perform steps ancillary to staining (or are compatible with separate systems that perform such ancillary steps), including: slide baking (for adhering the sample to the slide), dewaxing (also referred to as deparaffinization), antigen retrieval, counterstaining, dehydration and clearing, and coverslipping. Prichard, Overview of Automated Immunohistochemistry, Arch Pathol Lab Med., Vol. 138, pp. 1578-1582 (2014), incorporated herein by reference in its entirety, describes several specific examples of automated IHC/ISH slide stainers and their various features, including the INTELLIPATH (Biocare Medical), WAVE (Celerus Diagnostics), DAKO OMNIS and DAKO AUTOSTAINER LINK 48 (Agilent Technologies), BENCHMARK (Ventana Medical Systems, Inc.), LEICA BOND, and LAB VISION AUTOSTAINER (Thermo Scientific) automated slide stainers. Additionally, Ventana Medical Systems, Inc. is the assignee of a number of United States patents disclosing systems and methods for performing automated analyses, including U.S. Pat. Nos. 5,650,327, 5,654,200, 6,296,809, 6,352,861, 6,827,901 and 6,943,029, and U.S. Published Patent Application Nos. 20030211630 and 20040052685, each of which is incorporated herein by reference in its entirety. Commercially-available staining units typically operate on one of the following principles: (1) open individual slide staining, in which slides are positioned horizontally and reagents are dispensed as a puddle on the surface of the slide containing a tissue sample (such as implemented on the DAKO AUTOSTAINER LINK 48 (Agilent Technologies) and INTELLIPATH (Biocare Medical) stainers); (2) liquid overlay technology, in which reagents are either covered with or dispensed through an inert fluid layer deposited over the sample (such as implemented on VENTANA BENCHMARK and DISCOVERY stainers); (3) capillary gap staining, in which the slide surface is placed in proximity to another surface (which may be another slide or a coverplate) to create a narrow gap, through which capillary forces draw up and keep liquid reagents in contact with the samples (such as the staining principles used by DAKO TECHMATE, LEICA BOND, and DAKO OMNIS stainers). Some iterations of capillary gap staining do not mix the fluids in the gap (such as on the DAKO TECHMATE and the LEICA BOND). In variations of capillary gap staining termed dynamic gap staining, capillary forces are used to apply sample to the slide, and then the parallel surfaces are translated relative to one another to agitate the reagents during incubation to effect reagent mixing (such as the staining principles implemented on DAKO OMNIS slide stainers (Agilent)). In translating gap staining, a translatable head is positioned over the slide. A lower surface of the head is spaced apart from the slide by a first gap sufficiently small to allow a meniscus of liquid to form from liquid on the slide during translation of the slide. A mixing extension having a lateral dimension less than the width of a slide extends from the lower surface of the translatable head to define a second gap smaller than the first gap between the mixing extension and the slide. During translation of the head, the lateral dimension of the mixing extension is sufficient to generate lateral movement in the liquid on the slide in a direction generally extending from the second gap to the first gap. See WO 2011-139978 A1. It has recently been proposed to use inkjet technology to deposit reagents on slides. See WO 2016-170008 A1. This list of staining technologies is not intended to be comprehensive, and any fully or semi-automated system for performing biomarker staining may be incorporated into the histochemical staining platform 123.

Image acquisition system 120 may also include an automated H&E staining platform 124. Automated systems for performing H&E staining typically operate on one of two staining principles: batch staining (also referred to as "dip'n dunk") or individual slide staining. Batch stainers generally use vats or baths of reagents in which many slides are immersed at the same time. Individual slide stainers, on the other hand, apply reagent directly to each slide, and no two slides share the same aliquot of reagent. Examples of commercially available H&E stainers include the VENTANA SYMPHONY (individual slide stainer) and VENTANA HE 600 (individual slide stainer) series H&E stainers from Roche; the DAKO COVERSTAINER (batch stainer)

from Agilent Technologies; the LEICA ST4020 Small Linear Stainer (batch stainer), LEICA ST5020 MULTISTAINER (batch stainer), and the LEICA ST5010 AUTOSTAINER XL series (batch stainer) H&E stainers from Leica Biosystems Nussloch GmbH. H&E staining platform 124 is typically used in workflows in which a morphologically-stained serial section of the biomarker-stained section(s) is desired.

The immune context scoring system may further include a laboratory information system (LIS) 130. LIS 130 typically performs one or more functions selected from: recording and tracking processes performed on samples and on slides and images derived from the samples, instructing different components of the immune context scoring system to perform specific processes on the samples, slides, and/or images, and track information about specific reagents applied to samples and or slides (such as lot numbers, expiration dates, volumes dispensed, etc.). LIS 130 usually comprises at least a database containing information about samples; labels associated with samples, slides, and/or image files (such as barcodes (including 1-dimensional barcodes and 2-dimensional barcodes), radio frequency identification (RFID) tags, alpha-numeric codes affixed to the sample, and the like); and a communication device that reads the label on the sample or slide and/or communicates information about the slide between the LIS 130 and the other components of the immune context scoring system. Thus, for example, a communication device could be placed at each of a sample processing station, automated histochemical stainer 123, H&E staining platform 124, and scanning platform 125. When the sample is initially processed into sections, information about the sample (such as patient ID, sample type, processes to be performed on the section(s)) may be entered into the communication device, and a label is created for each section generated from the sample. At each subsequent station, the label is entered into the communication device (such as by scanning a barcode or RFID tag or by manually entering the alpha-numeric code), and the station electronically communicates with the database to, for example, instruct the station or station operator to perform a specific process on the section and/or to record processes being performed on the section. At scanning platform 125, the scanning platform 125 may also encode each image with a computer-readable label or code that correlates back to the section or sample from which the image is derived, such that when the image is sent to the image analysis system 100, image processing steps to be performed may be sent from the database of LIS 130 to the image analysis system and/or image processing steps performed on the image by image analysis system 100 are recorded by database of LIS 130. Commercially available LIS systems useful in the present methods and systems include, for example, VENTANA VANTAGE workflow system (Roche).

V. Generation of an Exemplary CD3/CD8 Continuous Scoring Function for Stage II Colorectal Cancer V.A. Samples and Sample Staining Stage II colorectal cancer was used as a model system to test whether continuous scoring functions could be useful in analyzing the immune context of solid tumors. A study was conducted on patient samples from the BioGrid cohort, obtained from patients who underwent surgical resection of stage II colon cancer. Characteristics of the cohort are set forth in Table 8:

TABLE 8

| BioGrid Cohort | |
|---|---|
| N | 425 |
| dMMR, pMMR | 82 (19.3%), 343 (80.7%) |
| Chemo-naïve, Chemo treated | 337 (79.3%), 88 (20.7%) |
| Age: ≤60, >60 | 16.7%, 83.3% |
| Male: dMMR, pMMR | 11.0%, 89.0% |
| Female: dMMR, pMMR | 28.8%, 71.2% |
| Left Sidedness: dMMR, pMMR | 5.8%, 94.2% |
| Right Sidedness: dMMR, pMMR | 32.3%, 67.7% |

Five 4 μm sections of each FFPE sample were obtained, mounted on a slide, and stained as follows:
1. CD3 negative control (i.e.staining protocol with primary antibody diluent in place of primary antibody)
2. CD3 IHC
3. H&E
4. CD8 IHC
5. CD8 neg. control.

IHC Slides were stained on a VENTANA BENCHMARK XT IHC/ISH automated slide stainer using OPTIVIEW DAB detection. The primary antibodies used were CONFIRM anti-CD3 (2GV6) Rabbit Monoclonal Primary Antibody (Ventana Medical Systems, Inc.) and CONFIRM anti-CD8 (SP57) Rabbit Monoclonal Primary Antibody. Slides were counterstained with hematoxylin. A serial section was also stained for H&E using a VENTANA SYMPHONY automated slide stainer.

Figure 5A:
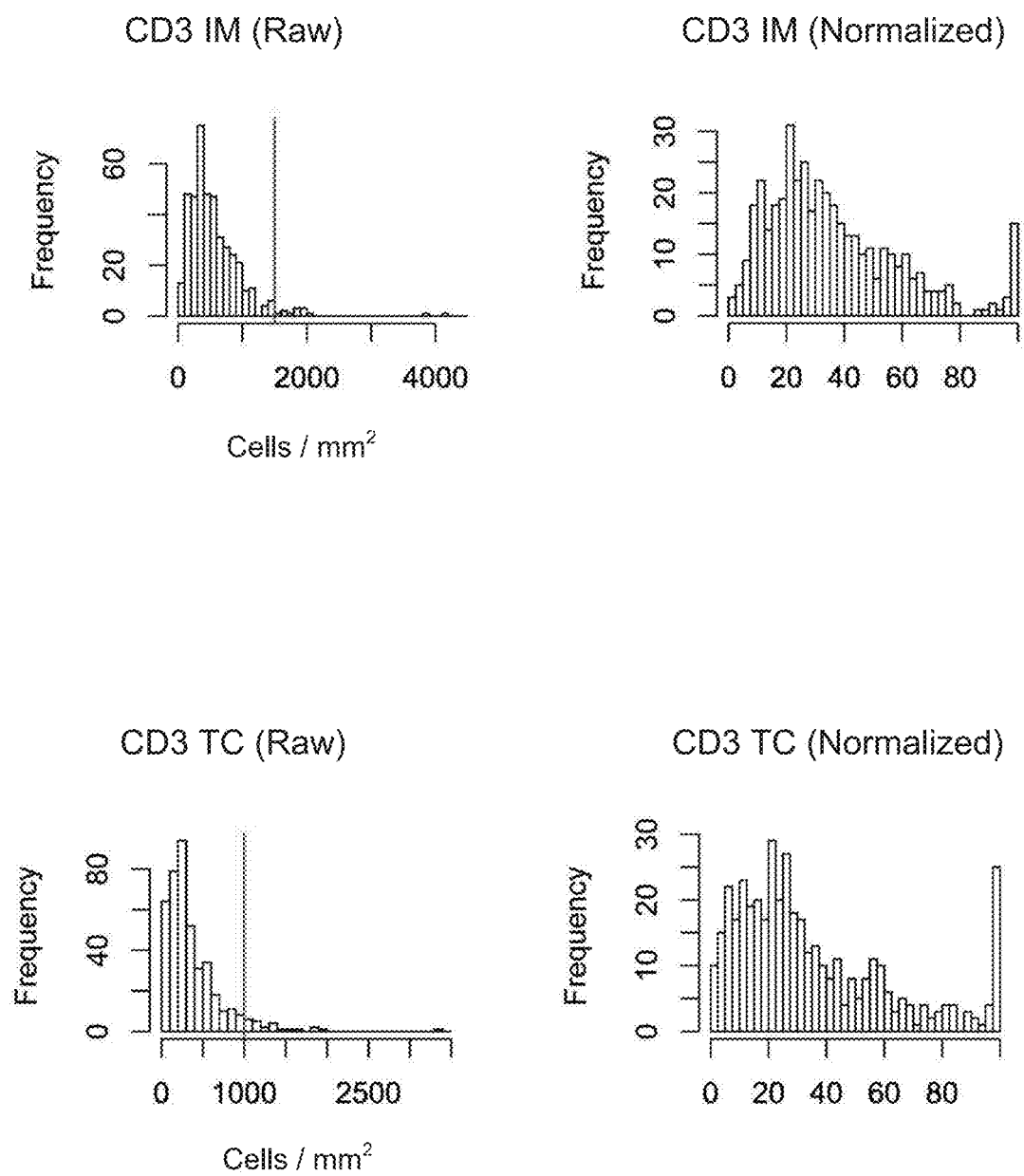
FIG. 5A displays histograms illustrating the distribution of CD3+ cell densities before normalization (Raw) and after normalization (Normalized). Vertical lines indicate the cut-offs used for normalization. The top row is for cell densities derived from an invasive margin region. The bottom row is cell densities obtained from a tumor core region.
Figure 5B:
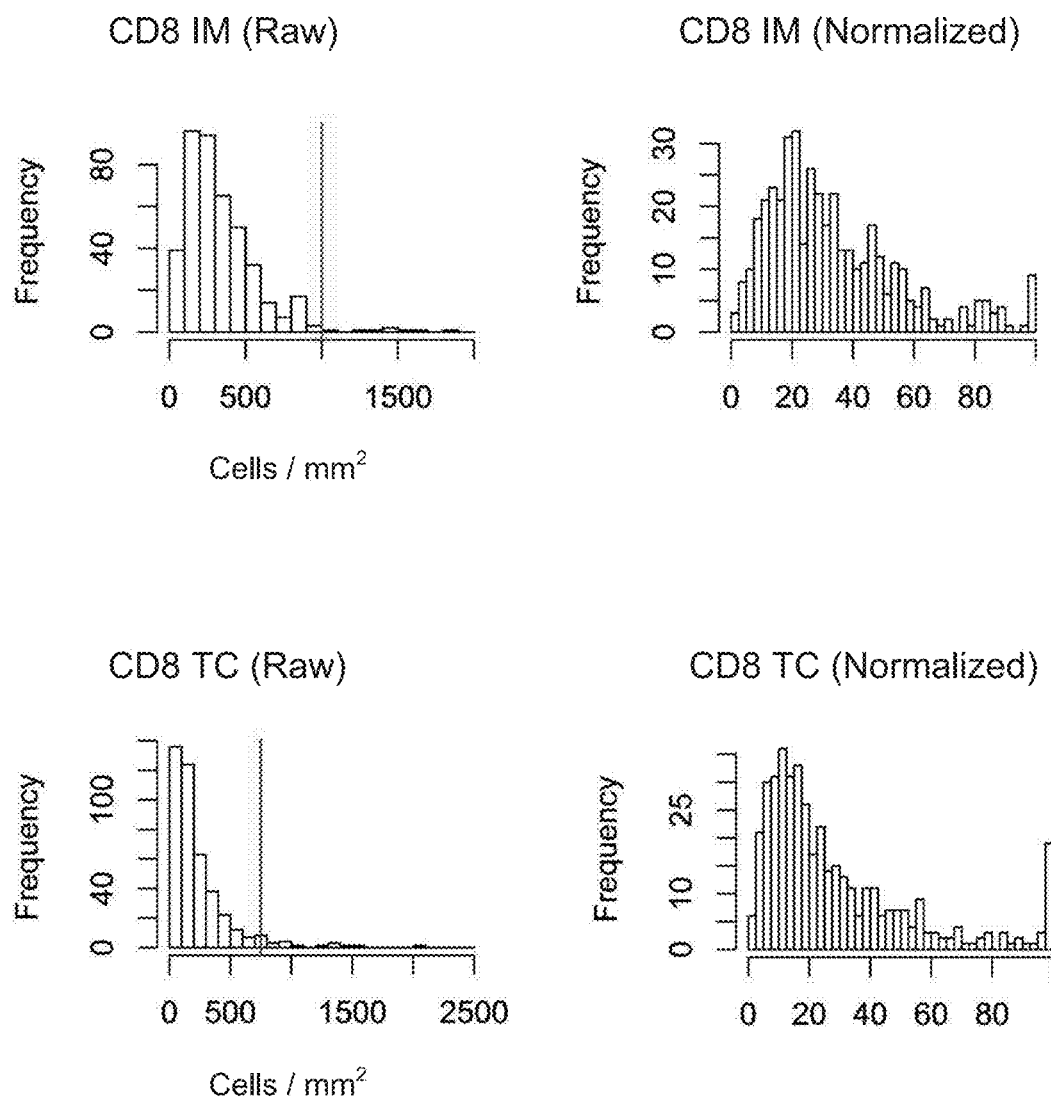
FIG. 5B displays histograms illustrating the distribution of CD8+ cell densities before normalization (Raw) and after normalization (Normalized). Vertical lines indicate the cut-offs used for normalization. The top row is for cell densities derived from an invasive margin region. The bottom row is cell densities obtained from a tumor core region.

V.B. Image Acquisition, Image Analysis, and Continuous Scoring Function Generation Slides were scanned on a VENTANA ISCAN CORED slide scanner. All image analysis was conducted using a VENTANA VIRTUOSO software suite. IHC slides were pre-processed to mark CD3+ cells in the CD3-stained slides and CD8+ cells in the CD8-stained slides. A tumor region and an invasive margin were annotated by an expert reader. A peri-tumor region was identified as a fixed width band around the invasive margin region. A global metric approach was used to obtain mean area density for CD3+ and CD8+ cells in the ROIs that were tested. The density values were normalized by first selecting a maximum meaningful cutoff from visual inspection of the distribution of the measured densities. Because of a right-skewed distribution for both the CD3+ and CD8+ cell densities, a maximum cutoff was chosen to allow meaningful separation of the majority of the results following normalization. Various maximum cutoffs were evaluated to identify the lowest maximum biologically meaningful density cutoff, in increments of 500, which would result in less than 30 subjects being marked above biologically meaningful. Any score above the selected cut point was then assigned a value equal to the cutoff. The reassigned scores were then divided by the cutoff value and multiplied by 100. Histograms of the raw densities and the normalized cell densities are illustrated at FIGS. 5A and 5B. The cutoffs used are in Table 9:

TABLE 9

| MARKER | ROI | CUTOFF |
|---|---|---|
| CD3 | TC | 1000 cells/mm$^2$ |
|  | IM | 1500 cells/mm$^2$ |
| CD8 | TC | 750 cells/mm$^2$ |
|  | IM | 1000 cells/mm$^2$ |

Univariate and multivariate cox proportional hazard models were then fitted using the normalized continuous scores to explore the association between the outcome (RFS or OS) and these densities. The model achieving the highest concordance index using was selected as the optimal model. Normalized continuous measures were fitted to a weighted model to derive a total score reflective of the probability of recurrence or survival. ROC curves were used to maximize of the sensitivity and specificity of the score in predicting outcome (RFS or OS) and to derive a cutoff to stratify the cohort into high and low risk bins. Kaplan-Meier curves were generated for the low and high score groups, and a logrank p-value was calculated. The Cox proportional hazard models were then fitted to get the hazard ratio and 95% CI to show the overall effect.

An optimal model was identified using a multivariate Cox model and normalized continuous CD3 and CD8 area density in tumor core (TC) and invasive margin (IM). The optimal model showed only CD3, CD8, and their interactions in the invasive margin as the statistical significant factors affecting the outcome. The following formula for the ICS based on these variables was extrapolated:

$$ICS_{cox} = \exp(-0.0370535 * CD3_{IM} - 0.0057619 * CD8_{IM} + 0.0003663 * CD3_{IM} * CD8_{IM}).$$

Figure 6:
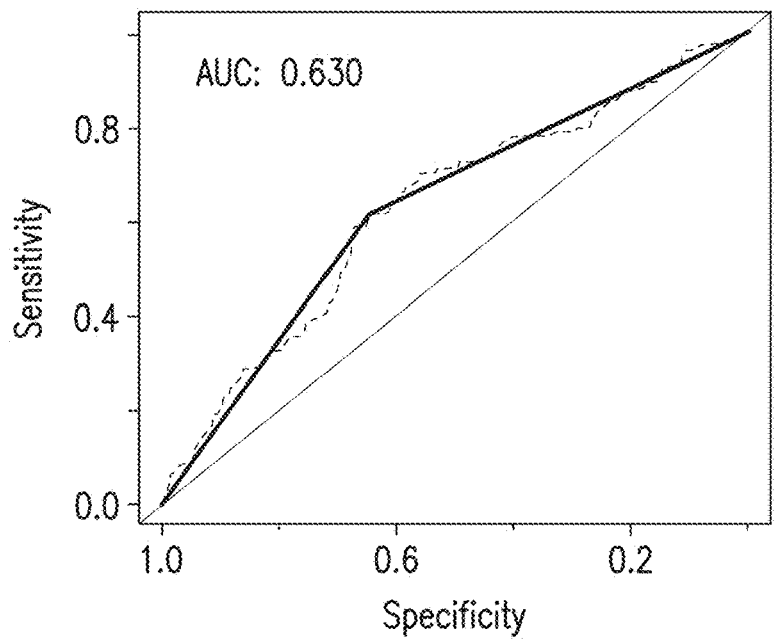
FIG. 6 is an ROC of an immune context scores for 5-year RFS in stage II colorectal cancer generated from a continuous scoring function obtained by evaluating CD3+ mean cell density and CD8+ mean cell density in an IM ROI using a Cox proportional hazard model.
Figure 7:
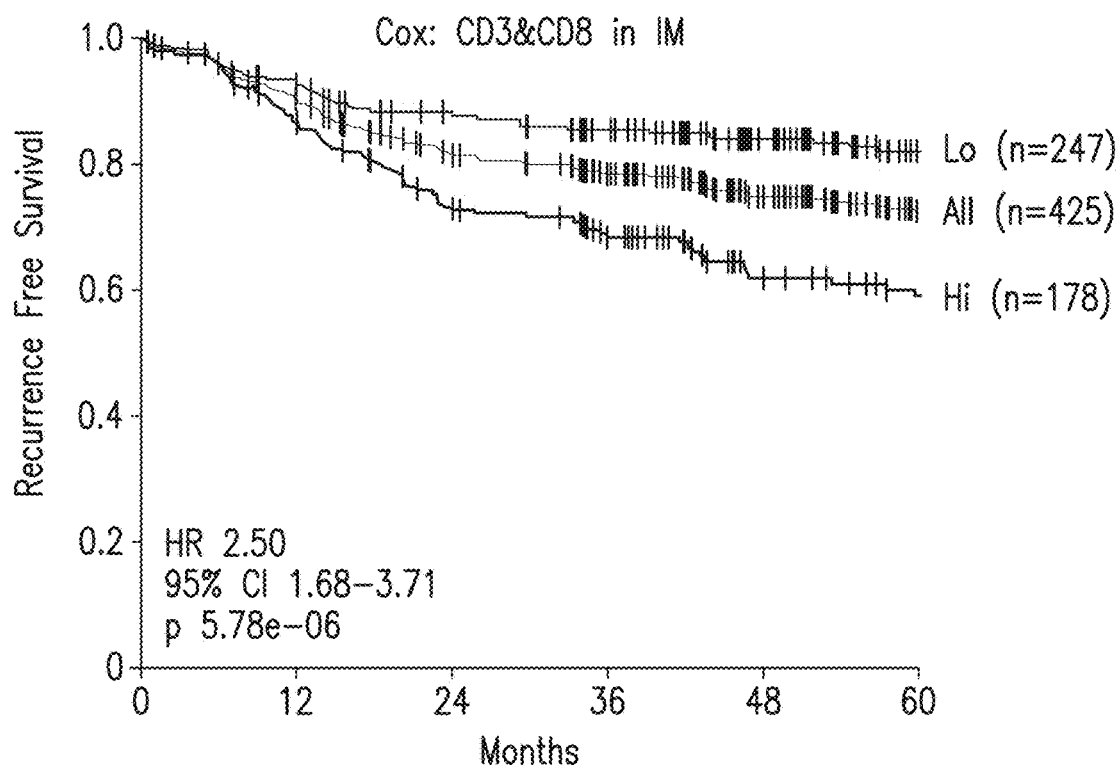
FIG. 7 is a Kaplan-Meier Plot of Recurrence-Free Survival of stage II colorectal cancer patients as predicted by an immune context score using CD3+ mean cell density and CD8+ mean cell density in an IM ROI, separated into "high risk" and "low risk" bins.

As can be seen, three independent variables are combined to obtain the risk score: (1) $CD3_{IM}$, which is the normalized mean density of CD3+ cells in an IM region; (2) $CD8_{IM}$, which is the normalized mean density of CD8+ cells in an IM region; and (3) $CD3_{IM}*CD8_{IM}$, which is the product of (1) and (2). Using the risk score against the 5-year RFS, ROC curves as depicted in FIG. 6 were generated, and an optimal cutoff point was determined to achieve the highest sensitivity and specificity. Patients were classified as LOW or HIGH risk using the cutoff, and Kaplan-Meier plot of RFS was generated. Hazard ratio (HIGH vs. LOW) and 95% CI were calculated from the Cox model, see FIG. 7. As can be seen, there is a significant difference between the HIGH and the LOW groups.

We therefore have shown that we can stratify patients according to likelihood of recurrence-free survival in stage II colorectal cancer using a 3-variable continuous scoring function based on density of CD3+ and CD8+ cells in an IM region. We have also shown that the normalized CD3+ cell density in the IM region has the strongest predictive weight, followed by the normalized CD8+ cell density, and then followed by the product of the normalized CD3+ cell density and the normalized CD8+ cell density. It will be appreciated by a person of ordinary skill in the art that, for the specific formula that we extrapolated, the numeric values of the constants for each independent variable are specific to the cohort used to generate the continuous scoring function. Use of a different cohort to generate the continuous scoring function will likely result in a different numeric value for the constants, although the weighting of the different variables will likely be similar and follow in the same order of weight. We therefore can generalize the extrapolated formula to formula 2:

$$ICS_{cox} = \exp(-b_1 * CD3_{AD} - b_2 * CD8_{AD} + b_3 * CD3_{AD} * CD8_{AD}) \quad \text{Formula 2}$$

wherein $CD3_{AD}$ is an area density of CD3+ cells in an IM or PT ROI, $CD8_{AD}$ is an area density of CD8+ cells in an IM or PT ROI, and $|b_1|>|b_2|>|b_3|$. This formula may be applicable to other solid tumors as well. Moreover, additional variables can be added to the formula, so long as the variables do not significantly diminish the predictive power of the function. In this vein, a continuous scoring function "consisting essentially of Formula 2," should be construed as formula 2, plus additional independent variables and constant weighting factors that do not significantly reduce the predictive or prognostic power of the continuous scoring function using formula 2 alone.

Figure 8:
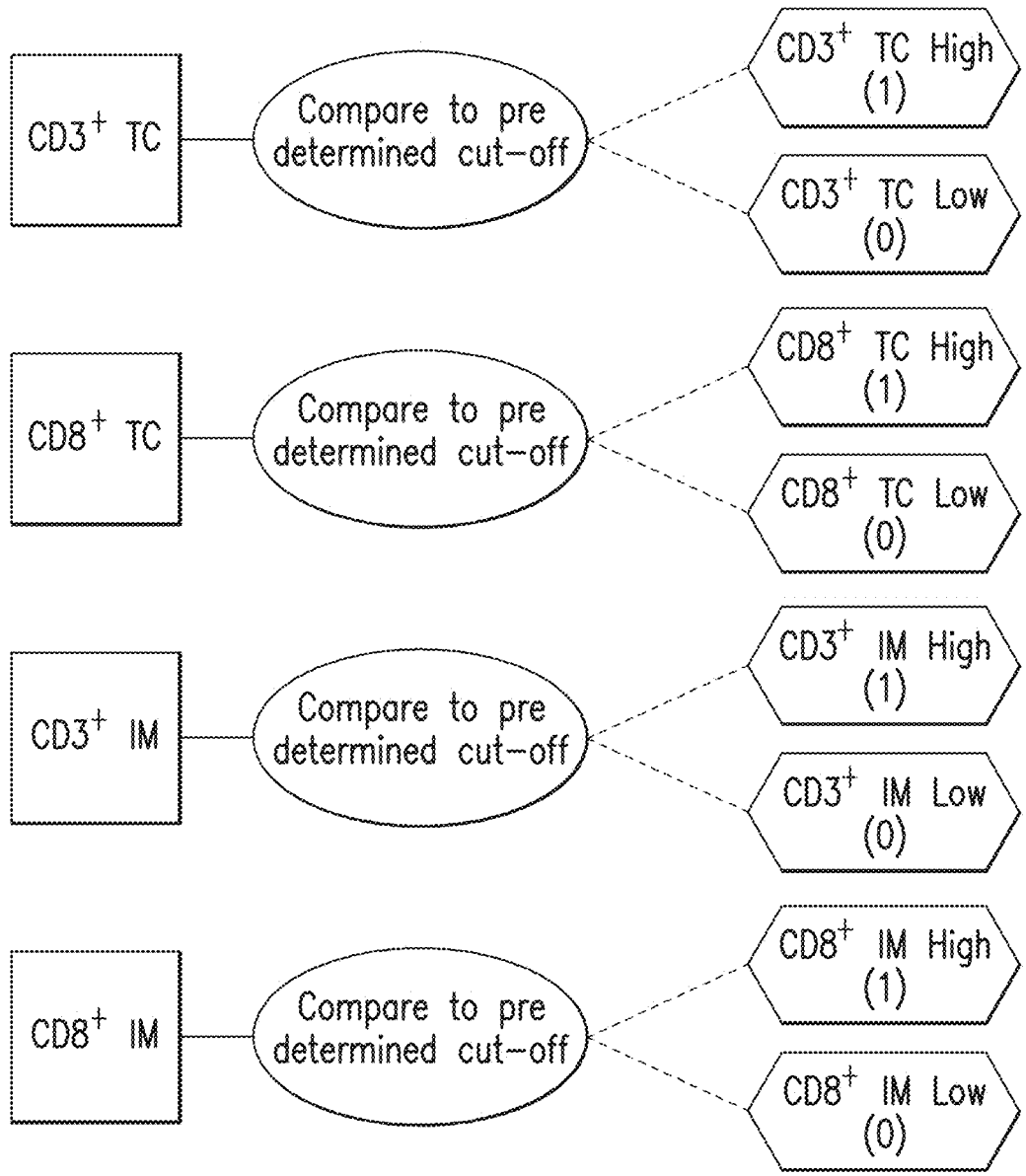
FIG. 8 is a flow chart showing the scoring process according to the Galon IMMUNOSCORE method.

Additionally, the Galon IMMUNOSCORE methodology was reproduced on the same samples. The Galon IMMUNOSCORE methodology is illustrated at FIG. 8. ROIs corresponding to TC and IM were marked, and the three 1 mm² areas in each ROI having the highest density of cells positive for each biomarker were selected. The mean of these three "hotspots" was selected as a feature metric, giving 4 feature metrics per sample ($CD3_{TC}$, $CD3_{IM}$, $CD8_{TC}$, and $CD8_{IM}$). The median for each feature metric was calculated for the entire cohort and used as a cutoff between "HIGH" and "LOW" bins for that feature metric. Feature metrics into a "HIGH" bin were given a score of 1. Feature metrics falling into a "LOW" bin were given a score of 0. The ICS for each sample was calculated as the sum of the scores for each of $CD3_{TC}$, $CD3_{IM}$, $CD8_{TC}$, and $CD8_{IM}$. Thus, 16 possible feature metric combinations with 4 possible scores could be obtained using the IMMUNOSCORE:

TABLE 10

| | CD3-TC | CD8-TC | CD3-IM | CD8-IM | Score |
|---|---|---|---|---|---|
| 1 | HIGH | HIGH | HIGH | HIGH | 4 |
| 2 | HIGH | LOW | HIGH | HIGH | 3 |
| 3 | HIGH | HIGH | LOW | HIGH | 3 |
| 4 | HIGH | HIGH | HIGH | LOW | 3 |
| 5 | LOW | HIGH | HIGH | HIGH | 3 |
| 6 | HIGH | HIGH | LOW | LOW | 2 |
| 7 | HIGH | LOW | HIGH | LOW | 2 |
| 8 | HIGH | LOW | LOW | HIGH | 2 |
| 9 | LOW | HIGH | HIGH | LOW | 2 |
| 10 | LOW | HIGH | LOW | HIGH | 2 |
| 11 | LOW | LOW | HIGH | HIGH | 2 |
| 12 | HIGH | LOW | LOW | LOW | 1 |
| 13 | LOW | HIGH | LOW | LOW | 1 |
| 14 | LOW | LOW | HIGH | LOW | 1 |
| 15 | LOW | LOW | LOW | HIGH | 1 |
| 16 | LOW | LOW | LOW | LOW | 0 |

Figure 9:
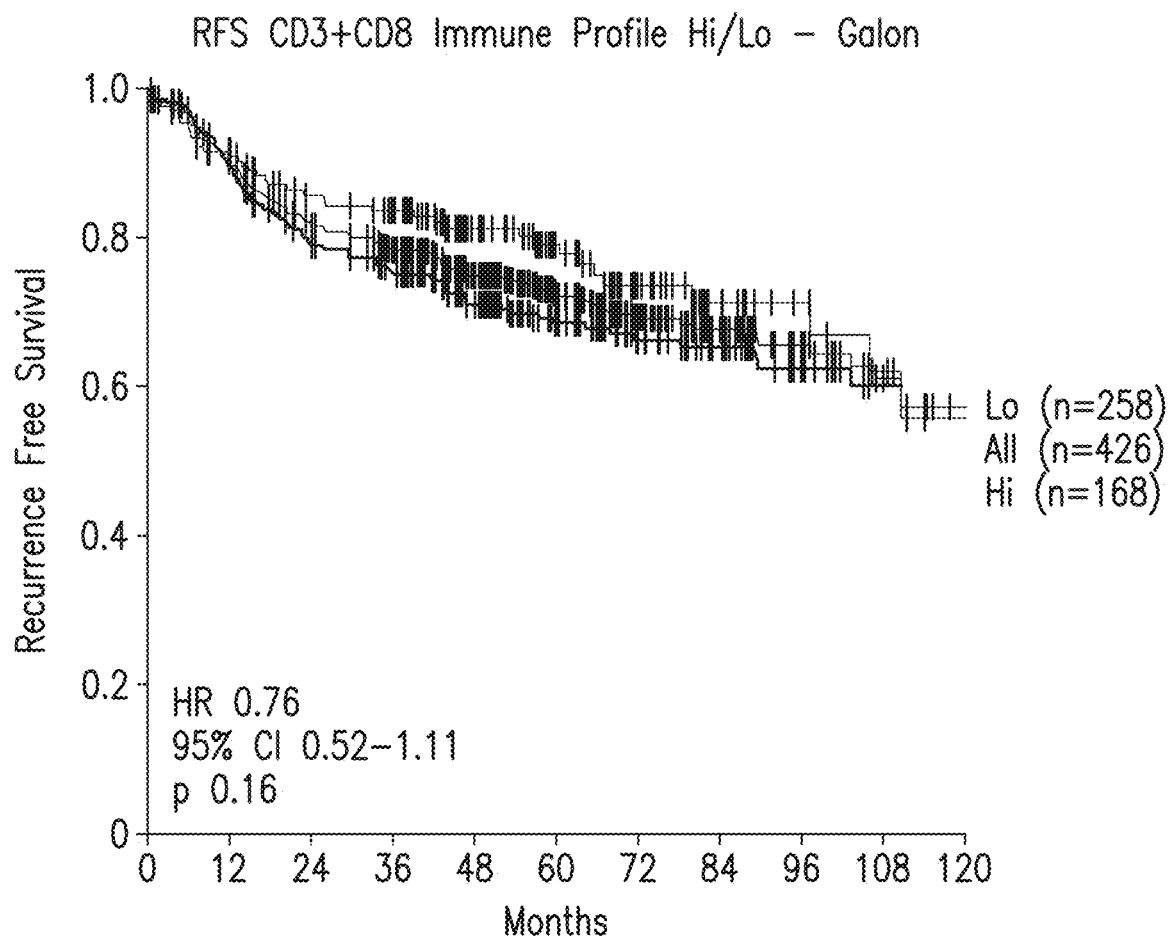
FIG. 9 is a Kaplan-Meier Plot of Recurrence-Free Survival of stage II colorectal cancer patients as predicted by a Galon IMMUNOSCORE method.

Results are displayed at FIG. 9. As can be seen, the predictive power of the Galon IMMUNOSCORE is less than the predictive power of a continuous scoring function in this cohort.

V.C. Stratification of Stage II, Chemo-Naïve pMMR Colorectal Tumors using a Continuous Scoring Function In another example, a continuous scoring function was developed on a cohort of 240 chemo-naïve stage II (tumor grade T3) colorectal cancers determined to have proficient mismatch repair (pMMR). Patients with pMMR tumors typically have a poorer prognosis than patients with deficient mismatch repair (dMMR), which is believed to be due at least in part to pMMR tumors being less immunogenic than dMMR tumors. MMR status of the tumors was previously determined based on positive IHC immunostaining with each of VENTANA anti-MLH1 (M1) mouse monoclonal, VENTANA anti-MSH2 (G219-1129) mouse monoclonal, CONFIRM anti-MSH6 (clone 44) mouse monoclonal, and VENTANA anti-PMS2 (EPR3947) rabbit monoclonal primary antibodies (Ventana Medical Systems, Inc.).

Serial sections of each sample were stained as described above in V.A. and Cox models were developed as described in V.B. The following ROI/Marker combinations were evaluated:

1. CD3/IM alone;
2. CD3/TC+CD3/IM;
3. CD3/IM+CD8/IM.

Figure 10:
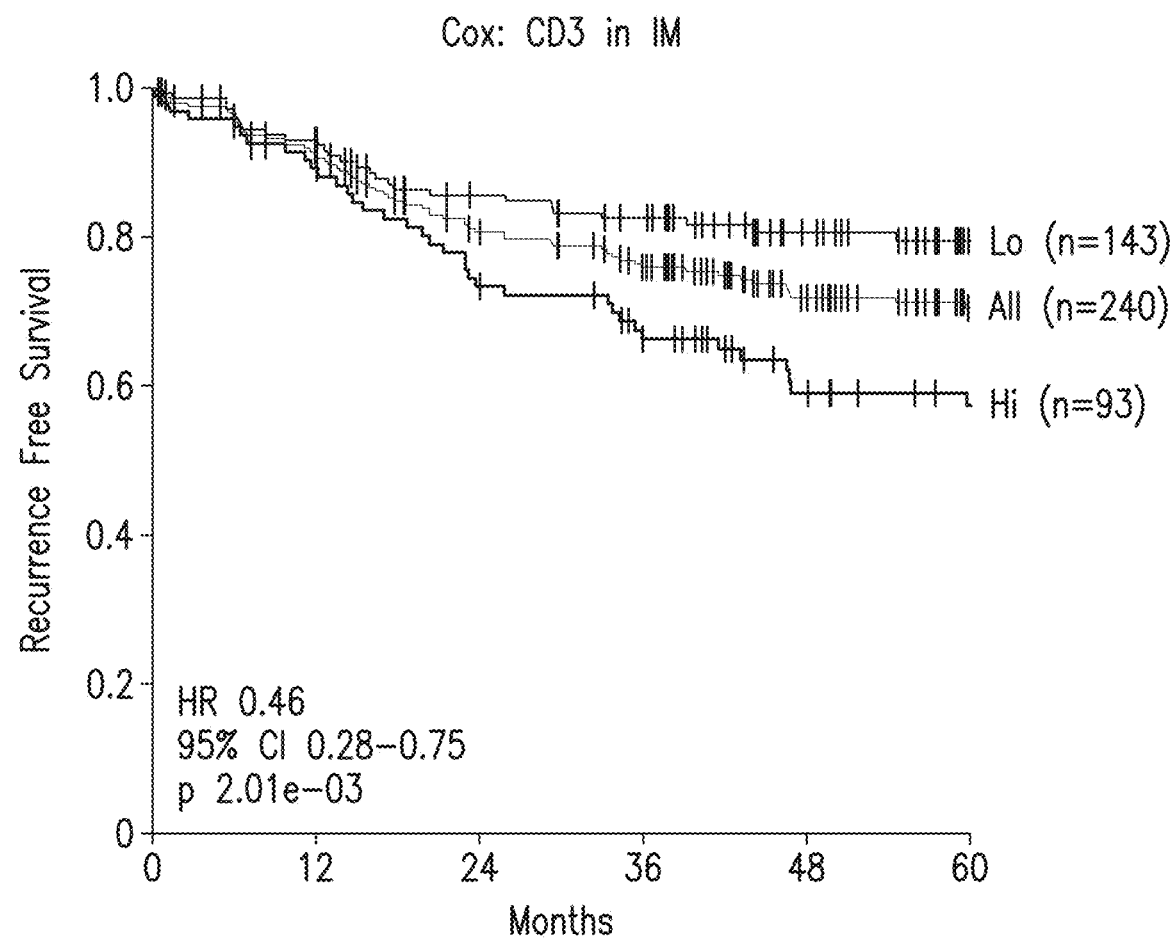
FIG. 10 is a Kaplan-Meier Plot of Recurrence Free Survival in chemo-naïve, mismatch repair proficient (pMMR) stage II (tumor grade T3) colorectal cancer. Patients are stratified on a univariate Cox model developed based on CD3 area density in an invasive margin (IM) ROI.
Figure 11:
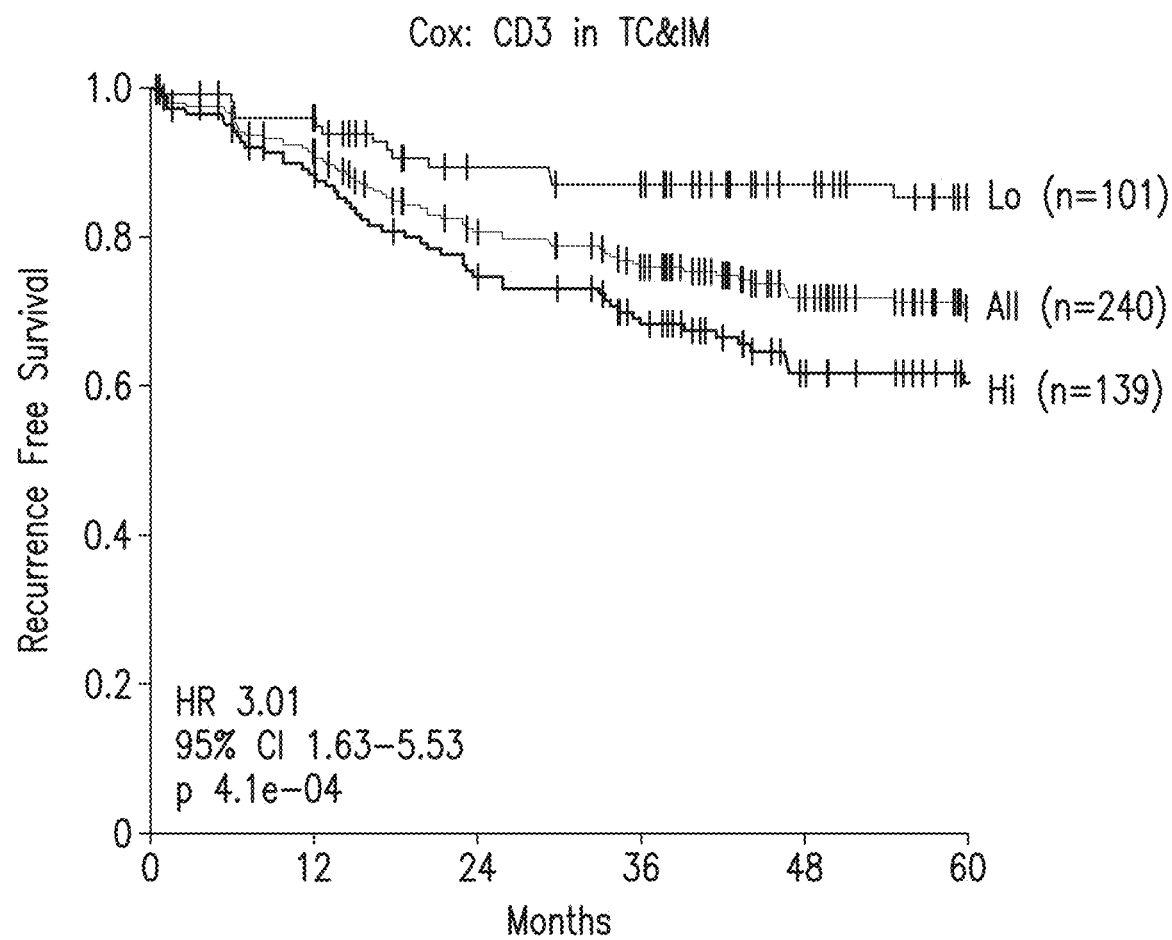
FIG. 11 is a Kaplan-Meier Plot of Recurrence Free Survival in chemo-naïve, mismatch repair proficient (pMMR) stage II (tumor grade T3) colorectal cancer. Patients are stratified on a multivariate Cox model developed based on CD3 area density in an invasive margin (IM) ROI and CD3 area density in a tumor core (TC) ROI.
Figure 12:
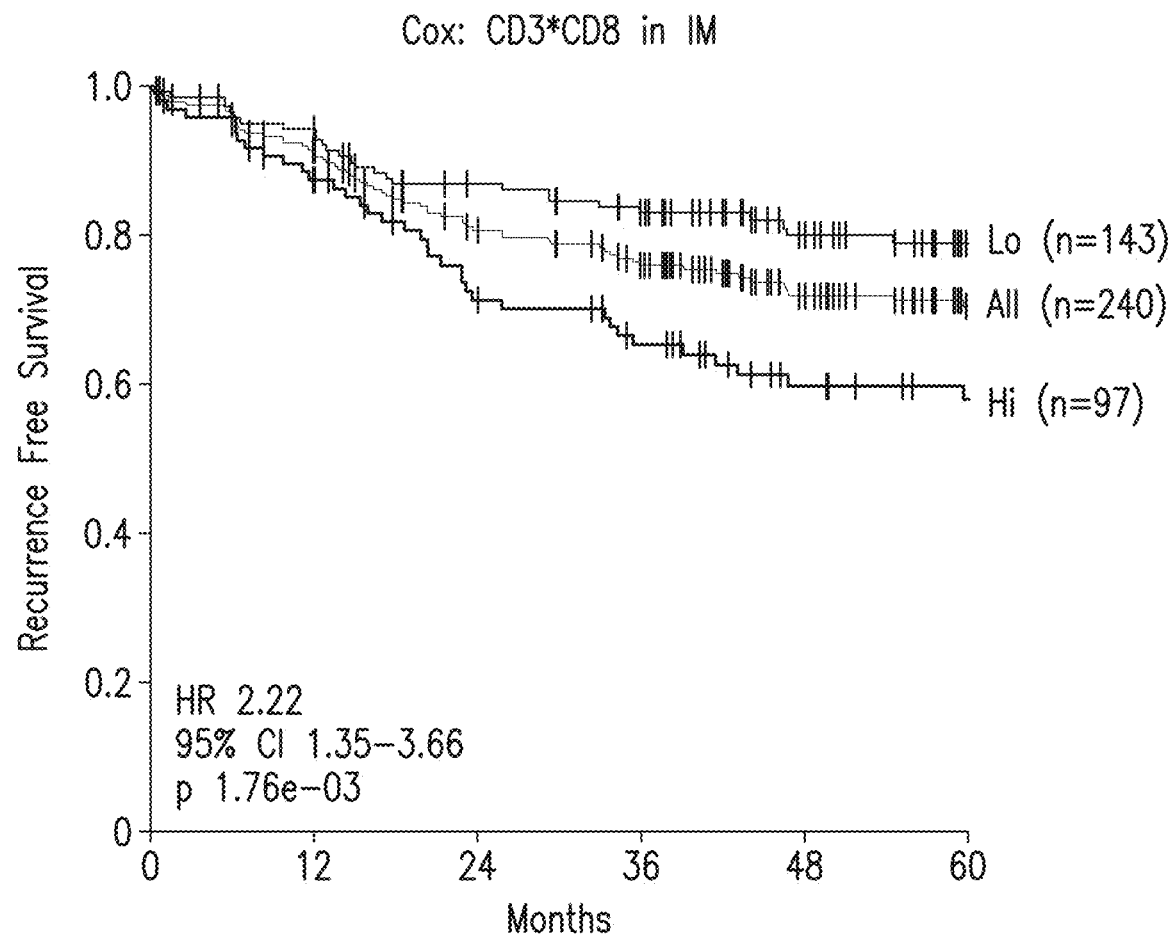
FIG. 12 is a Kaplan-Meier Plot of Recurrence Free Survival in chemo-naïve, mismatch repair proficient (pMMR) stage II (tumor grade T3) colorectal cancer. Patients are stratified on a multivariate Cox model developed based on CD3+ area density in an invasive margin (IM) ROI and CD8+ area density in the IM ROI.

The time-to-event used was RFS. Results are shown at FIG. 10 (CD3/IM), FIG. 11 (CD3/TC+CD3/IM), and FIG. 12 (CD3/IM & CD8/IM). As can be seen, all three arrangements stratify the pMMR patients, with the hazard ratios of 3.01 for CD3/TC+CD3/IM, 2.22 for CD3/IM+CD8/IM, and 0.46 for CD3/IM.

VI. Stratification of pMMR and dMMR Patients in BioGrid, Leeds, and a Combined Cohort A second study was conducted using a combined cohort of the BioGrid cohort and the Leeds cohort. Clinical characteristics of the two cohorts are set forth in Table 12:

TABLE 12-continued

|  | dMMR BioGrid (N-82) | dMMR Leeds (N = 54) | pMMR BioGrid (N = 343) | pMMR Leeds (N = 244) |
|---|---|---|---|---|
| Lymph Nodes |  |  |  |  |
| <12 | 10 (12.2%) | 4 (7.4%) | 78 (22.7%) | 44 (18.0%) |
| ≥12 | 72 (87.8%) | 50 (92.6%) | 265 (77.3%) | 200 (82.0%) |
| Age Group |  |  |  |  |
| ≤50 | 5 (6.1%) | 5 (9.3%) | 23 (6.7%) | 9 (3.7%) |
| 51 to 60 | 5 (6.1%) | 7 (13.0%) | 38 (11.1%) | 32 (13.1%) |
| 61 to 70 | 22 (26.8%) | 11 (20.4%) | 92 (26.8%) | 61 (25.0%) |
| 71 to 80 | 24 (29.3%) | 20 (37.0%) | 113 (32.9%) | 89 (36.5%) |
| >80 | 26 (31.7%) | 11 (20.4%) | 77 (22.4%) | 53 (21.7%) |

Samples were processed as described in section V.A. Images were generated and cell densities in TC and IM/PT regions were obtained as described in V.B. Stage II outcomes and cell densities are reported in Table 13:

TABLE 13

|  | dMMR BioGrid (N = 82) | dMMR Leeds (N = 54) | pMMR BioGrid (N = 343) | pMMR Leeds (N = 244) |
|---|---|---|---|---|
| RFS at 5 Years |  |  |  |  |
| Censored | 69 (84.1%) | 39 (72.2%) | 252 (73.5%) | 152 (62.3%) |
| Event | 13 (15.9%) | 15 (27.8%) | 91 (26.5%) | 92 (37.7%) |
| RFS at 3 Years |  |  |  |  |
| Censored | 72 (87.8%) | 43 (79.6%) | 266 (77.6%) | 174 (71.3%) |
| Event | 10 (12.2%) | 11 (20.4%) | 77 (22.4%) | 70 (28.7%) |
| CD3 TC Density |  |  |  |  |
| Mean (SD) | 530.30 (560.83) | 878.75 (926.83) | 335.71 (265.19) | 565.24 (426.46) |
| Median | 305.80 | 651.07 | 265.37 | 461.46 |
| Range | (7.08-3345.76) | (24.84-4900.05) | (16.07-1967.32) | (42.90-2570.15) |
| CD3 IM Density |  |  |  |  |
| Mean (SD) | 834.86 (719.22) | 1107.59 (804.25) | 497.16 (302.60) | 702.80 (511.17) |
| Median | 614.02 | 884.88 | 437.87 | 602.90 |
| Range | (83.86-4133.55) | (94.78-4260.53) | (21.63-1876.46) | (12.90-2693.84) |
| CD8 TC Density |  |  |  |  |
| Mean (SD) | 405.28 (411.01) | 349.85 (455.33) | 191.44 (169.46) | 172.91 (169.22) |
| Median | 297.23 | 230.25 | 138.65 | 122.37 |
| Range | (9.79-2085.11) | (8.02-2150.46) | (0.95-1413.67) | (3.68-1127.80) |
| CD8 IM Density |  |  |  |  |
| Mean (SD) | 513.56 (374.00) | 429.82 (342.14) | 303.77 (197.45) | 277.48 (221.36) |
| Median | 449.17 | 357.29 | 263.17 | 221.11 |
| Range | (68.67-1865.85) | (23.19-1538.29) | (0.32-1331.85) | (3.45-1385.81) |

TABLE 12

|  | dMMR BioGrid (N-82) | dMMR Leeds (N = 54) | pMMR BioGrid (N = 343) | pMMR Leeds (N = 244) |
|---|---|---|---|---|
| Chemo |  |  |  |  |
| NA | 0 (0.0%) | 0 (0.0%) | 0 (0.0%) | 7 (2.9%) |
| Naïve | 69 (84.1%) | 36 (66.7%) | 268 (78.1%) | 168 (68.9%) |
| Treated | 13 (15.9%) | 18 (33.3%) | 75 (21.9%) | 69 (28.3%) |
| Gender |  |  |  |  |
| Male | 57 (69.5%) | 31 (57.4%) | 141 (41.1%) | 107 (43.9%) |
| Female | 25 (30.5%) | 23 (42.6%) | 202 (58.9%) | 137 (56.1%) |

Cell densities reported in Table 13 are not normalized. Cox proportional hazard models were developed for the cohorts separately and as a pooled cohorts using the following variables: (a) MMR status; (b) clinical variables (age, gender, lymph node yield, and side); and (c) a immune context scores, including: (c1) CD3 density in TC only, (c2) CD3 density in IM only, (c3) CD3 density in TC & IM, (c4) CD3 & CD8 density in TC only, and (c5) CD3 & CD8 density in IM only.

Figure 13A:
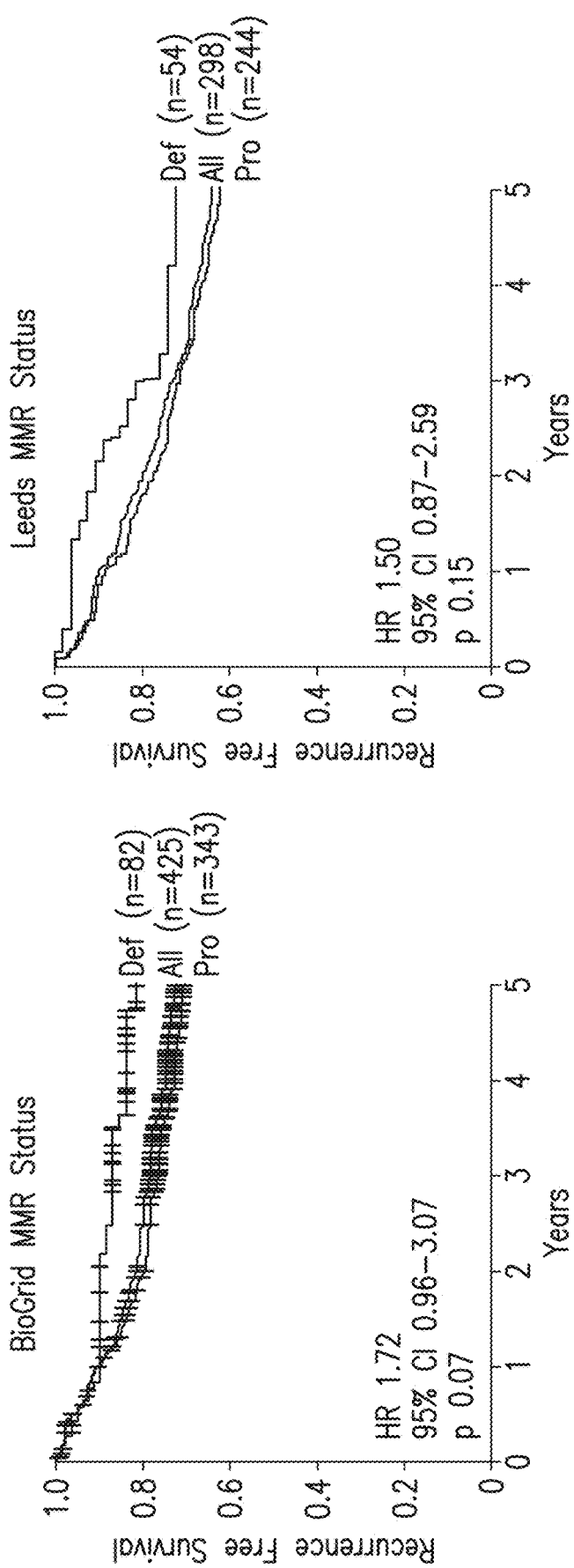
FIG. 13A is a Kaplan-Meier curve of the BioGrid cohort and the Leeds cohort when stratified on the basis of MMR status only.

FIG. 13A is a Kaplan-Meier curve of the BioGrid cohort and the Leeds cohort when stratified on the basis of MMR status only. The chemotherapy status of the patients included in this study is shown below in Table 14:

TABLE 14

|  |  | dMMR | pMMR |
|---|---|---|---|
| BioGrid | Naïve | 69 | 268 |
|  | Treated | 13 | 75 |
| Leeds | N/A | 0 | 7 |
|  | Naïve | 36 | 168 |
|  | Treated | 18 | 69 |

The number of patients at risk at each time point is set forth in Table 15:

TABLE 15

| Year |  | 0 | 1 | 2 | 3 | 4 | 5 |
|---|---|---|---|---|---|---|---|
| BioGrid | dMMR | 82 | 69 | 65 | 59 | 44 | 31 |
|  | pMMR | 343 | 296 | 248 | 226 | 173 | 137 |
| Leeds | dMMR | 54 | 52 | 49 | 43 | 40 | 39 |
|  | pMMR | 244 | 216 | 189 | 174 | 162 | 152 |

The BioGrid and Leeds cohorts were pooled and stratification repeated, resulting in 136 dMMR patients versus 587 pMMR patients, with a hazard ratio of 1.61 (95% CI of 1.08, 2.39), and p=0.02.

Figure 13B:
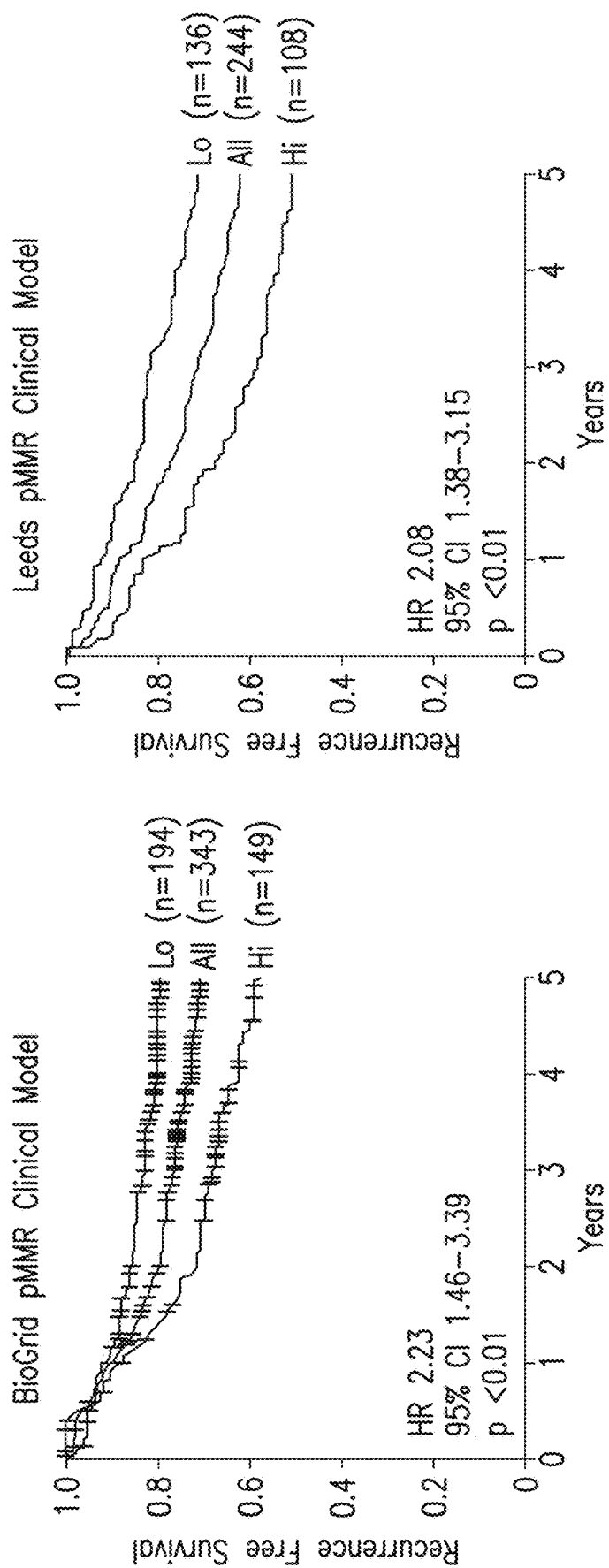
FIG. 13B is a Kaplan-Meier curve stratifying pMMR patients on a combination of clinical variables only. The final clinical model includes four clinical factors: age, gender, sidedness, and lymph node yield.

FIG. 13B is a Kaplan-Meier curve stratifying pMMR patients on a combination of clinical variables only. The final clinical model includes four clinical factors: age, gender, sidedness, and lymph node yield. Age was used as a categorical variable using bins every 10 years for most of the relevant ages for colon cancer (≤50, 51-60, 61-70, 71-80, >80). Gender was a binary variable with Female (the higher risk group) coded as 1. Sidedness was a binary variable with right (the higher risk group) coded as 1. Lymph node yield (represented as number of nodes harvested during tumor resection) was a binary variable with <12 (the higher risk group) coded as 1. These covariates were fit into a Cox Proportional Hazards model to calculate a clinical risk score. ROC curves and AUC calculations were then combined with outcome data (using Recurrence Free Survival) to find the cut point which maximizes the product of sensitivity and specificity. This cut point was then used to establish a high and low risk group. A new Cox PH model was fit to the binarized clinical risk category and a hazard ratio calculated. The chemotherapy status of the low risk and high risk groups from each cohort is shown below in Table 16:

TABLE 16

|  |  | Low | High |
|---|---|---|---|
| BioGrid | Naïve | 128 | 140 |
|  | Treated | 66 | 9 |
| Leeds | N/A | 1 | 6 |
|  | Naïve | 80 | 88 |
|  | Treated | 55 | 14 |

The number of patients at risk at each time point is set forth in Table 17:

TABLE 17

| Year |  | 0 | 1 | 2 | 3 | 4 | 5 |
|---|---|---|---|---|---|---|---|
| BioGrid | Low | 194 | 175 | 153 | 142 | 115 | 90 |
|  | High | 149 | 123 | 95 | 84 | 58 | 47 |
| Leeds | Low | 136 | 126 | 116 | 111 | 104 | 97 |
|  | High | 108 | 90 | 73 | 63 | 58 | 55 |

The pooled BioGrid and Leeds cohorts resulted in 341 low risk patients versus 246 high risk patients, with a hazard ratio of 2.25 (95% CI of 1.68, 3.02), and p≤0.01. Thus, clinical variables alone can further stratify pMMR stage II colorectal cancer patients.

Figure 13C:
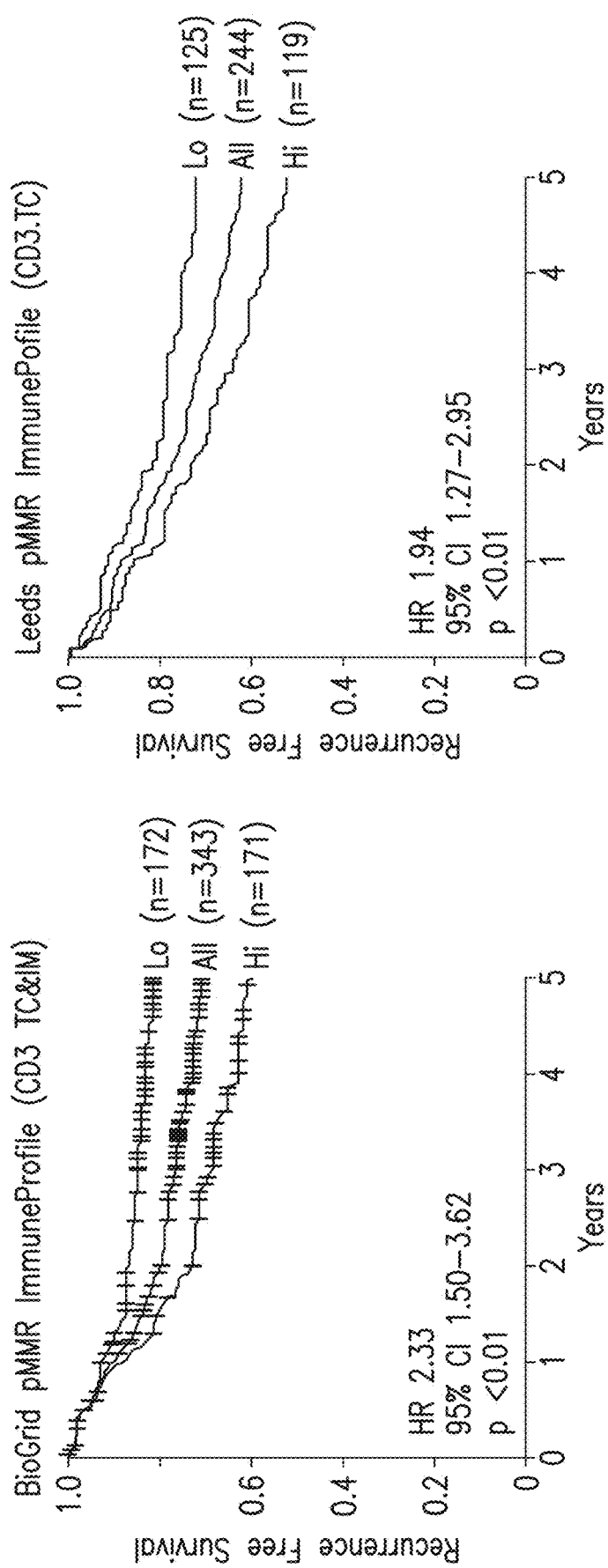
FIG. 13C is a Kaplan-Meier curve stratifying pMMR patients on the basis of CD3 density in both a TC region and an IM region (BioGrid cohort; left curve) and CD3 density in a TC region only (Leeds cohort; right curve).

FIG. 13C is a Kaplan-Meier curve stratifying pMMR patients on the basis of an immune context score only. Optimal Cox models were selected for the BioGrid and the Leeds cohorts separately, and for a pooled cohort, and cutpoints between high and low risk bins were selected as described in section V.B. The optimal Cox model for the BioGrid cohort relied only on CD3 density in an IM region and CD3 density in a TC region as the variables. The optimal Cox model for the Leeds cohort relied only on CD3 density in a TC region as the variable. The chemotherapy status of the low risk and high risk groups from each cohort is shown below in Table 18:

TABLE 18

|  |  | Low | High |
|---|---|---|---|
| BioGrid | Naïve | 136 | 132 |
|  | Treated | 36 | 39 |
| Leeds | N/A | 3 | 4 |
|  | Naïve | 82 | 86 |
|  | Treated | 40 | 29 |

The number of patients at risk at each time point is set forth in Table 19:

TABLE 19

| Year |  | 0 | 1 | 2 | 3 | 4 | 5 |
|---|---|---|---|---|---|---|---|
| BioGrid | Low | 172 | 153 | 131 | 125 | 99 | 75 |
|  | High | 171 | 145 | 117 | 101 | 74 | 62 |
| Leeds | Low | 125 | 114 | 102 | 98 | 94 | 90 |
|  | High | 119 | 102 | 87 | 76 | 68 | 62 |

The pooled BioGrid and Leeds cohorts resulted in 262 low risk patients versus 325 high risk patients, with a hazard ratio of 1.69 (95% CI of 1.24, 2.30), and p<0.01. Thus, Cox proportional hazard models based on CD3 can further stratify pMMR stage II colorectal cancer patients.

Two types of integration between the clinical model and the immune context score information were evaluated: model combination and covariate combination.

In the model combination, two risk categories were combined to form a 4-group crossing which is then simplified into a 3-level stratification. The clinical model in every case was the same as described above. The immune components for this type of model varied between MMR subsets and cohorts. Table 20 summarizes which immune components are present in the immune context score model for each of the subsets and cohorts investigated.

TABLE 20

| Cohort | Subset | Covariates Included | HR (95% CI) | p-value |
|---|---|---|---|---|
| BioGrid | dMMR | CD3.IM & CD8.IM | 2.45 (0.74, 8.08) | 0.14 |
|  | pMMR | CD3.TC & CD3.IM | 2.33 (1.50, 3.62) | <0.01 |
| Leeds | dMMR | CD3.TC | 2.89 (1.03, 8.13) | 0.04 |
|  | pMMR | CD3.TC | 1.94 (1.27, 2.95) | <0.01 |
| Pooled | dMMR | CD3.IM & CD8.IM | 1.95 (0.91, 4.18) | 0.08 |
|  | pMMR | CD3.TC & CD8.TC | 1.69 (1.24, 2.30) | <0.01 |

In this process, CD3 and CD8 density in each of TC and IM were fed into a model building/selection of a Cox proportional hazard model resulted in the terms listed providing the best fit for the subset to which it is assigned. Similar to the clinical model process, this Cox PH model was used to calculate an immune context score. This immune context score was then combined with outcome data (Recurrence Free Survival) to calculate the cut point which maximized the product of sensitivity and specificity. This cut point was utilized to establish high and low risk groups based on immune context score. High and Low risk groups from the clinical and immune context score models were crossed resulting in a 2×2=4-level stratification (High/High, High/Low, Low/High, and Low/Low). In most instances, the two middle groups (high/low or low/high) were combined to form the medium risk group of the 3-level stratification. A new Cox PH was fit to the 3-level stratification to allow the calculation of HRs for high versus low and medium versus low risk groups.

Figure 13D:
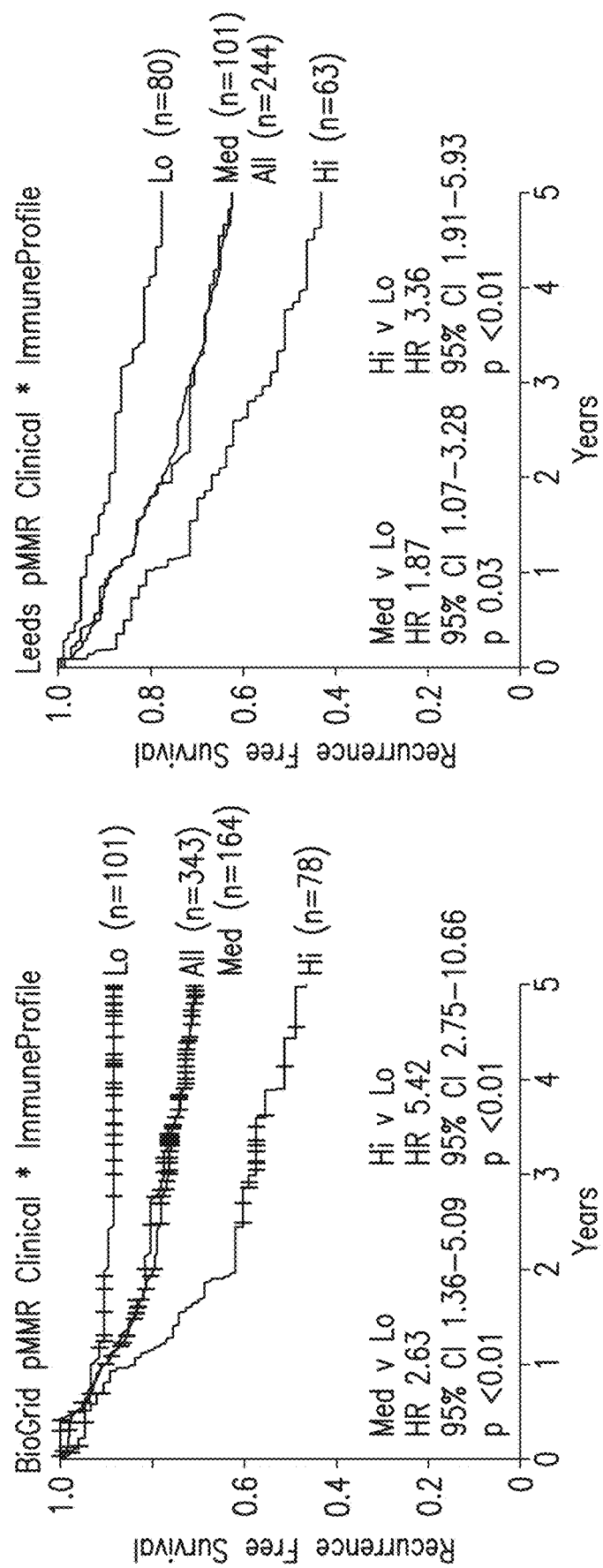
FIG. 13D illustrates a Kaplan-Meier curve of pMMR patients stratified using a model combination of clinical variables and immune context score. For each, the clinical variables include age, gender, sidedness, and lymph node yield. For the BioGrid cohort (left curve), the immune context score was based on CD3 density in both a TC region and an IM region. For the Leeds cohort (right curve), the immune context score was based on CD3 density in a TC region only.

FIG. 13D illustrates a Kaplan-Meier curve of pMMR patients stratified using a model combination. The chemotherapy status of the low risk and high risk groups from each cohort is shown below in Table 21:

TABLE 21

|  |  | Low | Medium | High |
|---|---|---|---|---|
| BioGrid | Naïve | 68 | 128 | 72 |
|  | Treated | 33 | 36 | 6 |
| Leeds | N/A | 1 | 2 | 4 |
|  | Naïve | 46 | 70 | 52 |
|  | Treated | 33 | 29 | 7 |

The number of patients at risk at each time point is set forth in Table 22:

TABLE 22

| Year |  | 0 | 1 | 2 | 3 | 4 | 5 |
|---|---|---|---|---|---|---|---|
| BioGrid | Low | 101 | 91 | 81 | 78 | 65 | 47 |
|  | Medium | 164 | 146 | 122 | 111 | 84 | 71 |
|  | High | 78 | 61 | 45 | 37 | 24 | 19 |
| Leeds | Low | 80 | 75 | 71 | 69 | 65 | 62 |
|  | Medium | 101 | 90 | 76 | 71 | 68 | 63 |
|  | High | 63 | 51 | 42 | 34 | 29 | 27 |

The pooled BioGrid and Leeds cohorts resulted in 159 low risk patients, 285 medium risk, and 143 high risk patients, with a low to medium risk hazard ratio of 2.59 (95% CI of 1.64, 4.09), and a low to high risk hazard ratio of 4.07 (95% CI 2.53, 6.55), and p<0.01.

Figure 13E:
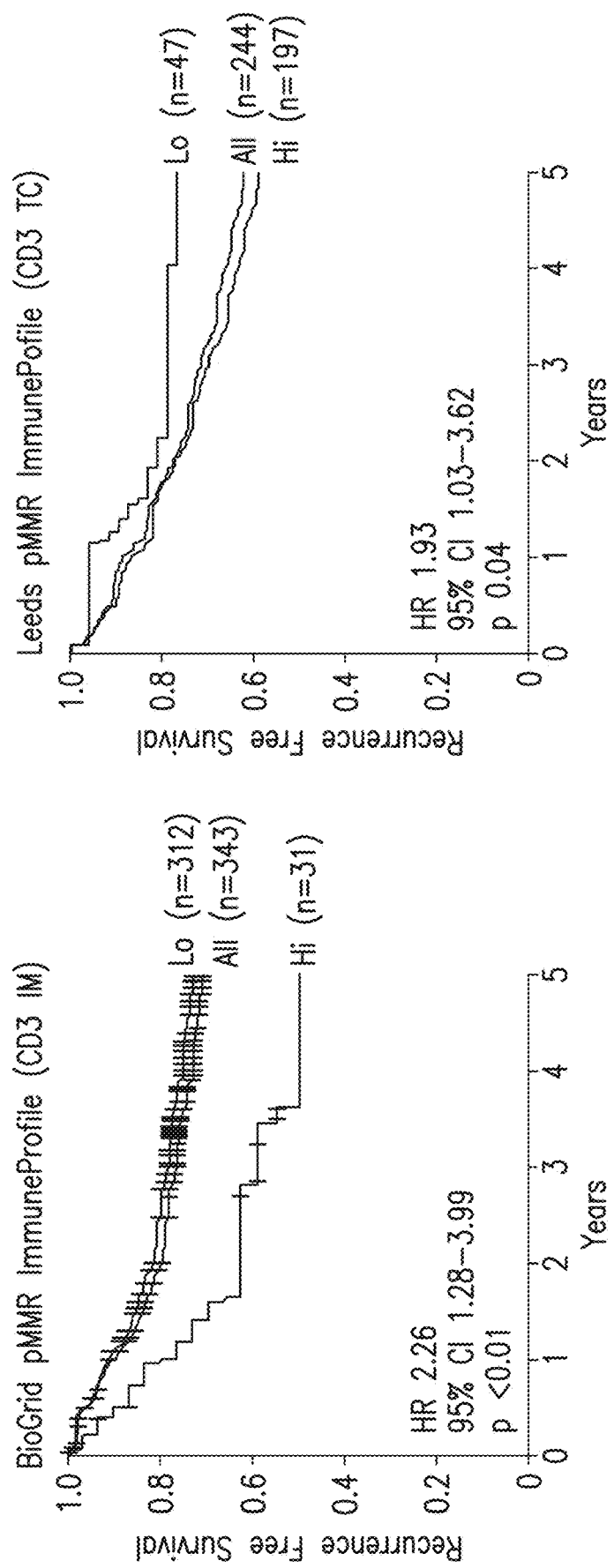
FIG. 13E illustrates a Kaplan-Meier curve of pMMR patients stratified using a covariate combination of clinical variables and immune context score. For each, the clinical variables include age, gender, sidedness, and lymph node yield. For the BioGrid cohort (left curve), the immune context score was based on CD3 density in an IM region only. For the Leeds cohort (right curve), the immune context score was based on CD3 density in a TC region only.

The second method of combination of the clinical and immune profile measures is a covariate-level combination. In this process, the normalized continuous biomarker/tissue area density scores were included in a Cox PH model with the four clinical factors listed above. Backward selection was used to eliminate the immune components that were not contributing to the model. If only one biomarker was included in the final model, then the HR and p value for each cutoff level was calculated, and the cutoff that provided the highest HR when p value is <0.05 was determined. If more than one biomarker was retained after backward selection, then the Cox model was built only with those biomarkers and used to calculate an overall risk score. This risk score was used to calculate the HR and p value for each cutoff level, and the cutoff that provided the highest HR when p value <0.05 was identified. This cut point was then applied to establish high and low risk categories (2-level stratification). A new Cox proportional hazard was fit to calculate the HR between these risk levels. FIG. 13E illustrates a Kaplan-Meier curve of pMMR patients stratified using a covariate combination. The chemotherapy status of the low risk and high risk groups from each cohort is shown below in Table 23:

TABLE 23

|  |  | Low | High |
|---|---|---|---|
| BioGrid | Naïve | 244 | 24 |
|  | Treated | 68 | 7 |
| Leeds | N/A | 2 | 5 |
|  | Naïve | 31 | 137 |
|  | Treated | 14 | 55 |

The number of patients at risk at each time point is set forth in Table 24:

TABLE 24

| Year |  | 0 | 1 | 2 | 3 | 4 | 5 |
|---|---|---|---|---|---|---|---|
| BioGrid | Low | 312 | 275 | 230 | 211 | 163 | 127 |
|  | High | 31 | 23 | 18 | 15 | 10 | 10 |
| Leeds | Low | 47 | 45 | 38 | 37 | 37 | 36 |
|  | High | 197 | 171 | 151 | 137 | 125 | 116 |

The pooled BioGrid and Leeds cohorts resulted in 86 low risk patients, 501 high risk patients, with a hazard ratio of 1.55 (95% CI of 0.97, 2.46), and p=0.07.

Figure 13F:
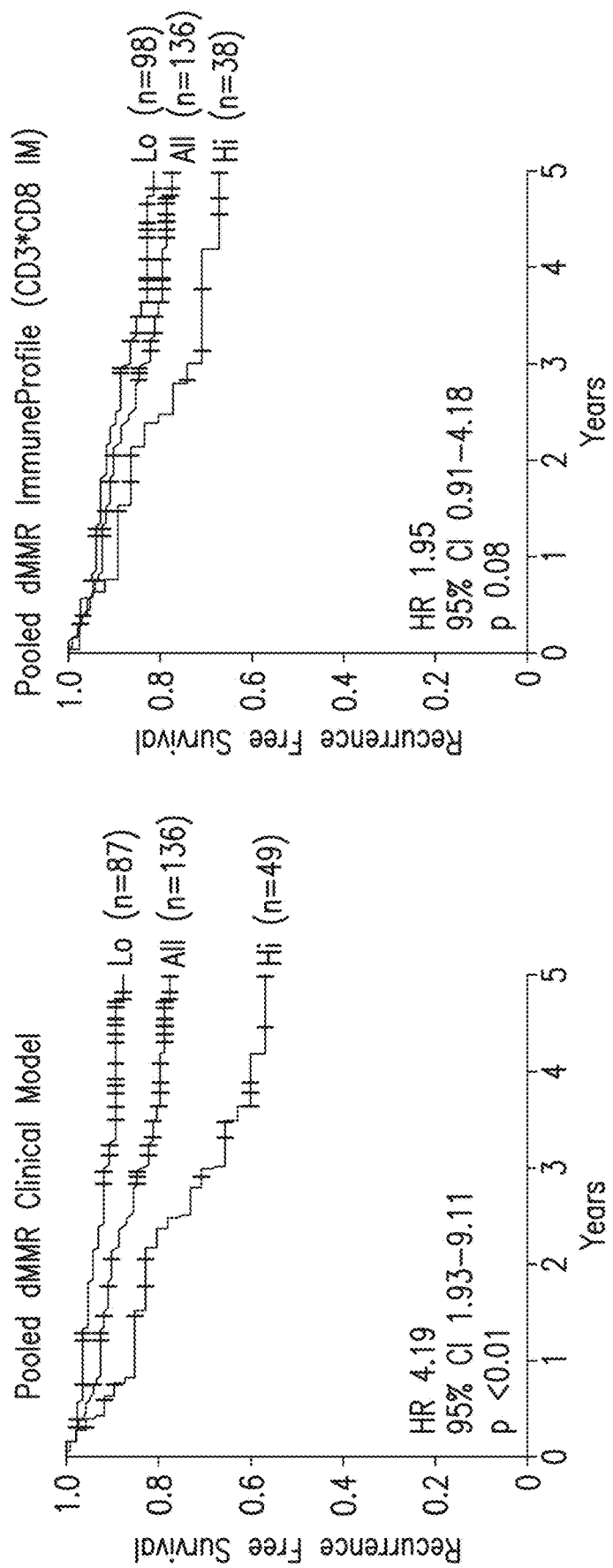
FIG. 13F illustrates Kaplan-Meier curves of dMMR patients from a pooled cohort stratified using either clinical variables only or an immune context score only. The clinical variables include age, gender, sidedness, and lymph node yield. The immune context score includes CD3 density and CD8 density in an IM region.

FIG. 13F illustrates Kaplan-Meier curves of dMMR patients from a pooled cohort stratified using either clinical variables only or an immune context score only. The chemotherapy status of the low risk and high risk groups from each cohort is shown below in Table 25:

TABLE 23

|  |  | Low | High |
|---|---|---|---|
| Clinical Model | Naïve | 59 | 46 |
|  | Treated | 28 | 3 |
| Immune context score | Naïve | 72 | 33 |
|  | Treated | 26 | 5 |

The number of patients at risk at each time point is set forth in Table 24:

TABLE 24

| Year |  | 0 | 1 | 2 | 3 | 4 | 5 |
|---|---|---|---|---|---|---|---|
| Clinical Model | Low | 87 | 83 | 79 | 75 | 65 | 54 |
|  | High | 49 | 38 | 35 | 27 | 19 | 16 |
| Immune context score | Low | 98 | 89 | 85 | 79 | 65 | 56 |
|  | High | 38 | 32 | 29 | 23 | 19 | 14 |

Figure 13G:
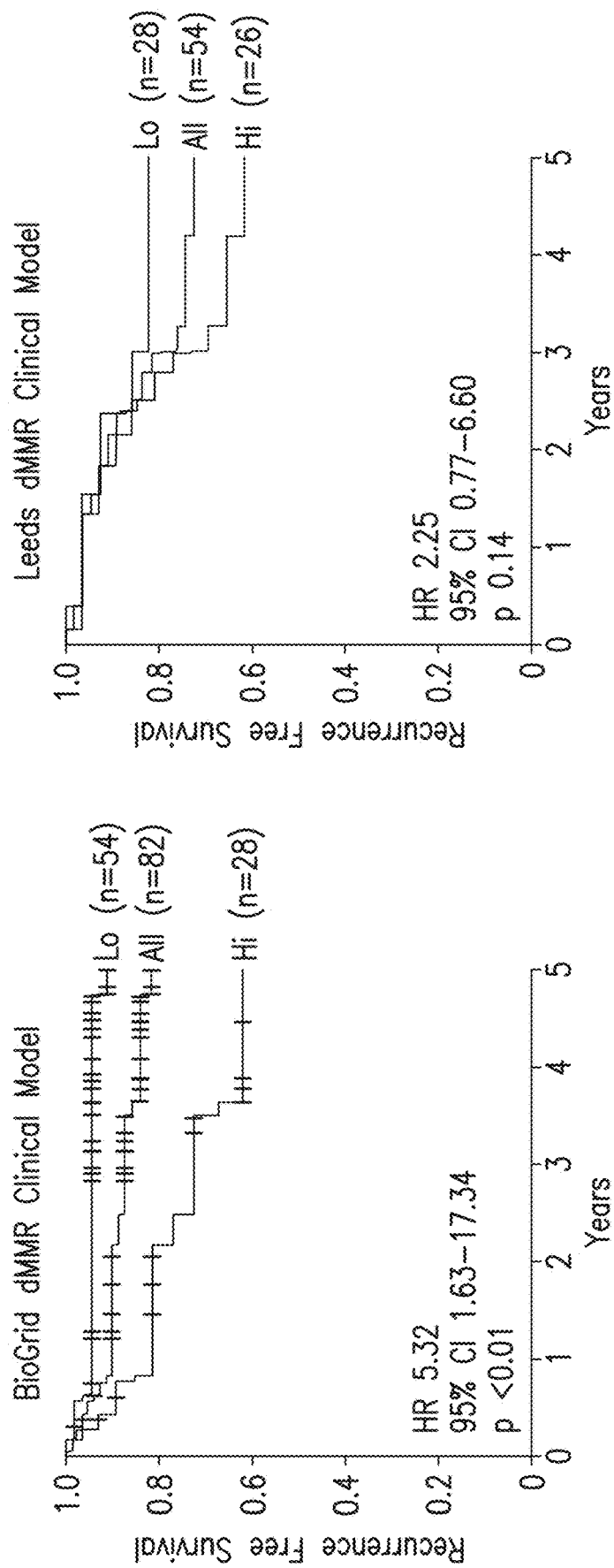
FIG. 13G illustrates Kaplan-Meier curves of dMMR patients from the BioGrid or Leeds cohort stratified using clinical variables only. The clinical variables include age, gender, sidedness, and lymph node yield.

FIG. 13G illustrates Kaplan-Meier curves of dMMR patients from the BioGrid or Leeds cohort stratified using clinical variables only. The chemotherapy status of the low risk and high risk groups from each cohort is shown below in Table 25:

TABLE 25

|         |         | Low | High |
|---------|---------|-----|------|
| BioGrid | Naïve   | 42  | 27   |
|         | Treated | 12  | 1    |
| Leeds   | Naïve   | 15  | 21   |
|         | Treated | 13  | 5    |

The number of patients at risk at each time point is set forth in Table 26:

TABLE 26

| Year    |      | 0  | 1  | 2  | 3  | 4  | 5  |
|---------|------|----|----|----|----|----|----|
| BioGrid | Low  | 54 | 48 | 46 | 43 | 35 | 23 |
|         | High | 28 | 21 | 19 | 16 | 9  | 8  |
| Leeds   | Low  | 28 | 27 | 25 | 24 | 23 | 23 |
|         | High | 26 | 25 | 24 | 19 | 17 | 16 |

Figure 13H:
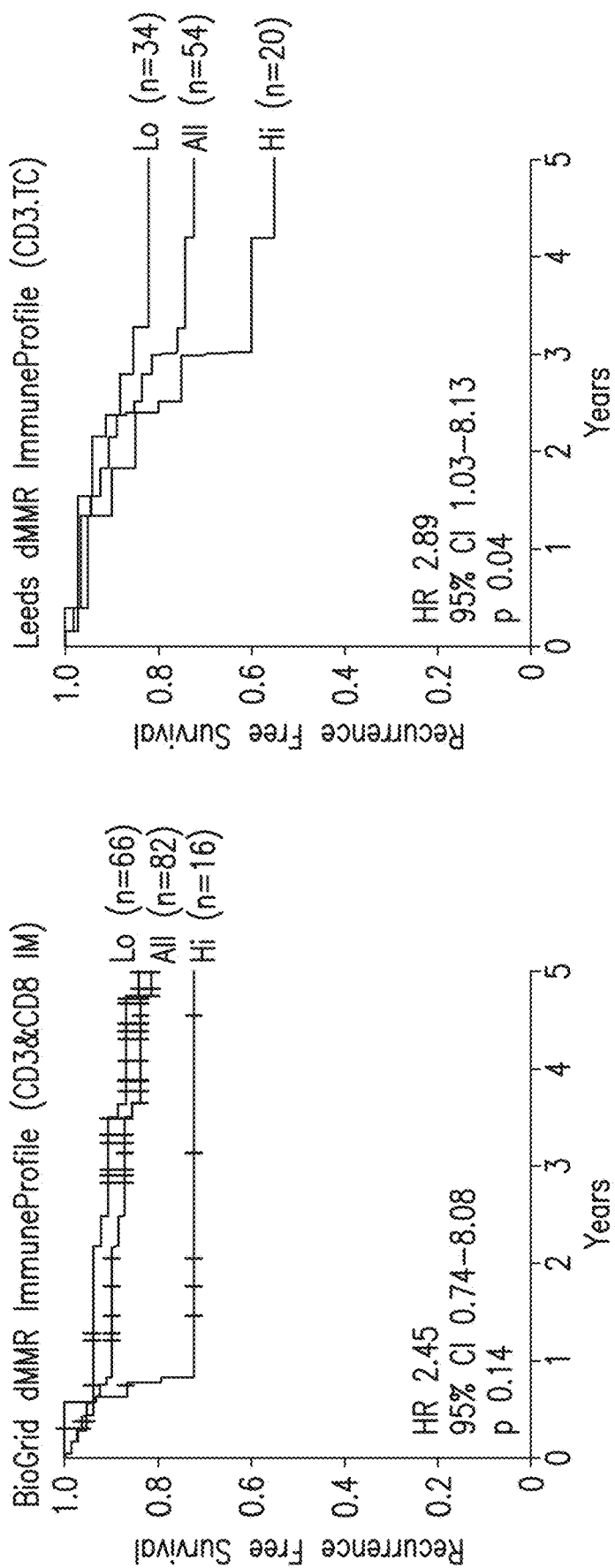
FIG. 13H illustrates Kaplan-Meier curves of dMMR patients from a the BioGrid or Leeds cohort stratified using immune context score only. For the BioGrid cohort (left curve), the immune context score includes CD3 density and CD8 density in an IM region. For the Leeds cohort, the immune context score includes CD3 density in a TC region only.

FIG. 13H illustrates Kaplan-Meier curves of dMMR patients from a the BioGrid or Leeds cohort stratified using immune context score only. The chemotherapy status of the low risk and high risk groups from each cohort is shown below in Table 27:

TABLE 27

|         |         | Low | High |
|---------|---------|-----|------|
| BioGrid | Naïve   | 55  | 14   |
|         | Treated | 11  | 2    |
| Leeds   | Naïve   | 20  | 16   |
|         | Treated | 14  | 4    |

The number of patients at risk at each time point is set forth in Table 28:

TABLE 28

| Year    |      | 0  | 1  | 2  | 3  | 4  | 5  |
|---------|------|----|----|----|----|----|----|
| BioGrid | Low  | 66 | 59 | 57 | 52 | 39 | 27 |
|         | High | 16 | 10 | 8  | 7  | 5  | 4  |
| Leeds   | Low  | 34 | 33 | 32 | 29 | 28 | 28 |
|         | High | 20 | 19 | 17 | 14 | 12 | 11 |

Figure 13I:
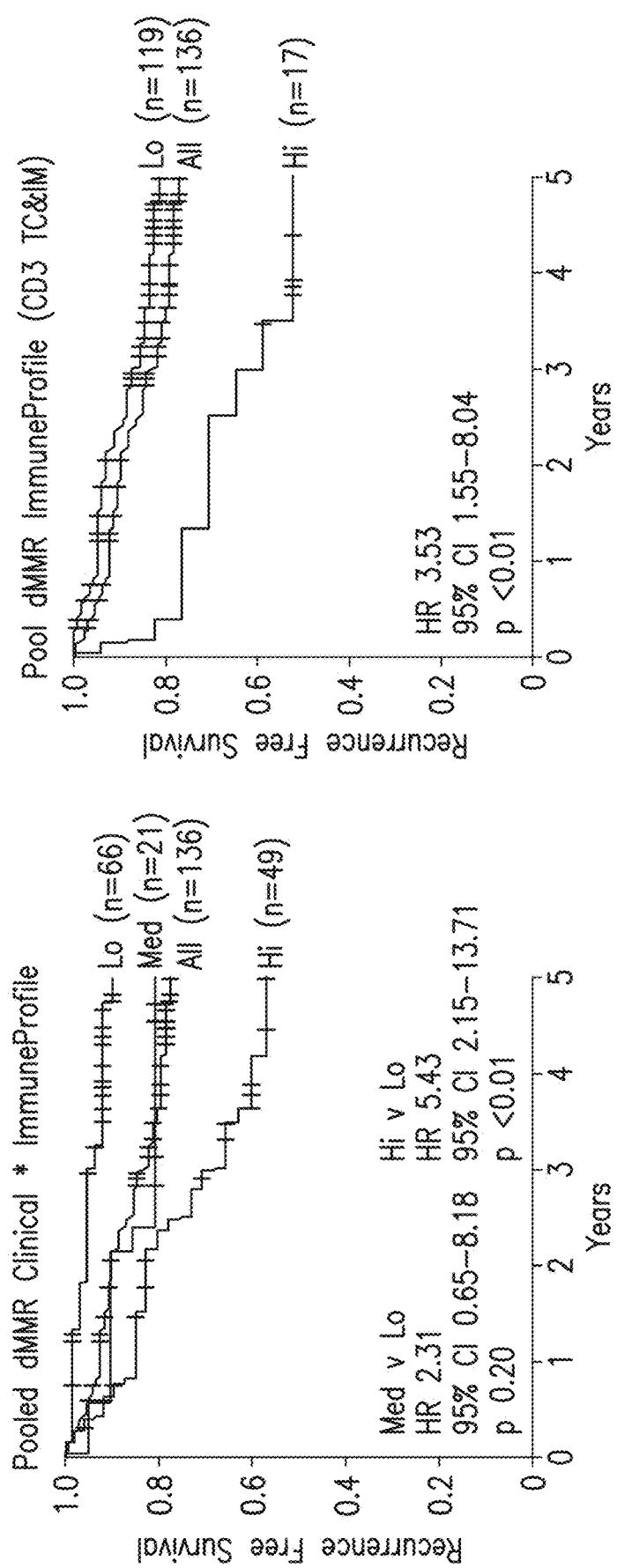
FIG. 13I illustrates Kaplan-Meier curves of dMMR patients from a pooled cohort stratified by combining clinical variables and immune context score using either a model combination (left curve) or a covariate combination (right curve). In each case, the clinical variables include age, gender, sidedness, and lymph node yield. In the model combination, the final model for immune context score includes CD3 density and CD8 density in an IM region. In the covariate combination, the final model includes CD3 density in both a TC and an IM region.

FIG. 13I illustrates Kaplan-Meier curves of dMMR patients from a pooled cohort stratified by combining clinical variables and immune context score using either a model combination (left curve) or a covariate combination (right curve). The chemotherapy status of the risk groups from each stratification is shown below in Table 29:

TABLE 29

|           |         | Low | Medium | High |
|-----------|---------|-----|--------|------|
| Model     | Naïve   | 43  | 16     | 46   |
|           | Treated | 23  | 5      | 3    |
| Covariate | Naïve   | 91  | N/A    | 14   |
|           | Treated | 28  | N/A    | 3    |

The number of patients at risk at each time point is set forth in Table 30:

TABLE 30

| Year      |        | 0   | 1   | 2   | 3  | 4  | 5  |
|-----------|--------|-----|-----|-----|----|----|----|
| Model     | Low    | 66  | 64  | 60  | 59 | 51 | 43 |
|           | Medium | 21  | 19  | 19  | 16 | 14 | 11 |
|           | High   | 49  | 38  | 35  | 27 | 19 | 16 |
| Covariate | Low    | 119 | 108 | 102 | 92 | 79 | 66 |
|           | High   | 17  | 13  | 12  | 10 | 5  | 4  |

Figure 13J:
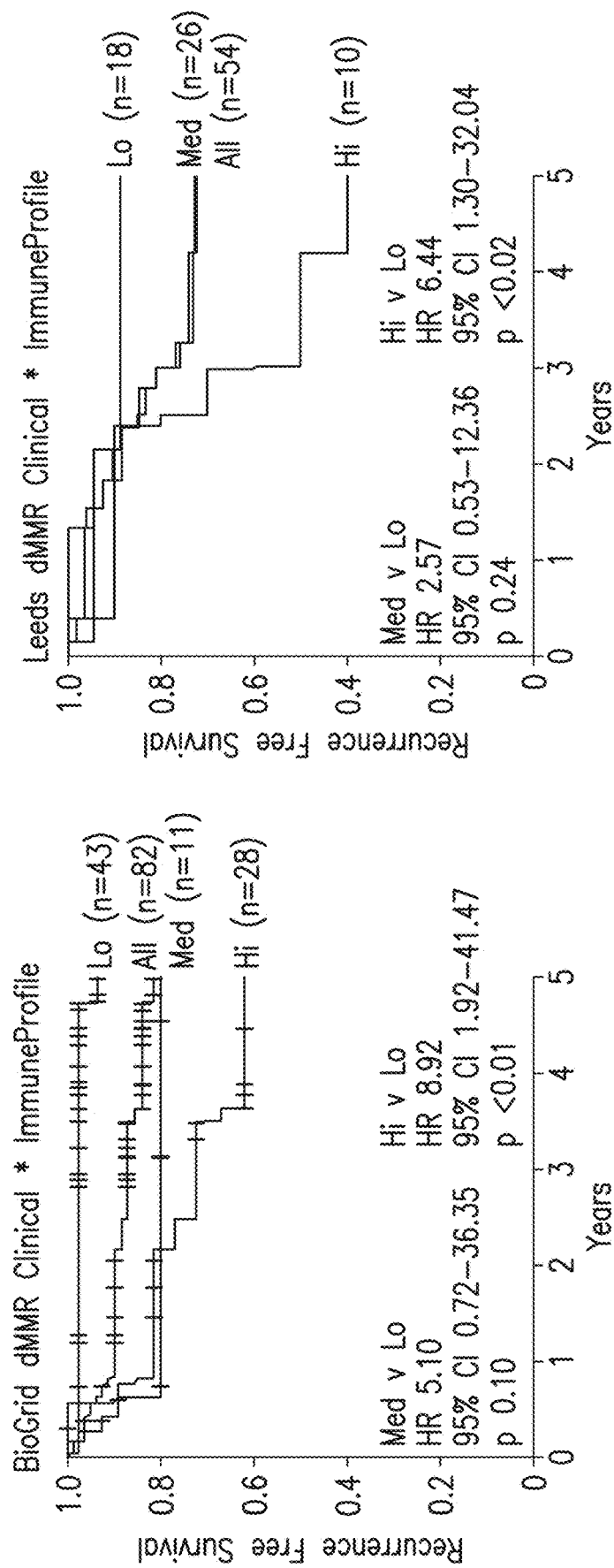
FIG. 13J and FIG. 13K illustrate Kaplan-Meier curves of dMMR patients from the BioGrid (left curve) and Leeds cohorts (right curve) stratified by combining clinical variables and immune context score using a model combination.

FIG. 13J illustrates Kaplan-Meier curves of dMMR patients from the BioGrid and Leeds cohorts stratified by combining clinical variables and immune context score using a model combination. The chemotherapy status of the risk groups from each stratification is shown below in Table 31:

TABLE 31

|         |         | Low | Medium | High |
|---------|---------|-----|--------|------|
| BioGrid | Naïve   | 43  | 16     | 46   |
|         | Treated | 23  | 5      | 3    |
| Leeds   | Naïve   | 8   | 19     | 9    |
|         | Treated | 10  | 7      | 1    |

The number of patients at risk at each time point is set forth in Table 32:

TABLE 32

| Year      |        | 0  | 1  | 2  | 3  | 4  | 5  |
|-----------|--------|----|----|----|----|----|----|
| Model     | Low    | 43 | 41 | 39 | 36 | 30 | 19 |
|           | Medium | 11 | 7  | 7  | 7  | 5  | 4  |
|           | High   | 28 | 21 | 19 | 16 | 9  | 8  |
| Covariate | Low    | 18 | 17 | 17 | 16 | 16 | 16 |
|           | Medium | 26 | 26 | 23 | 21 | 19 | 19 |
|           | High   | 10 | 9  | 9  | 6  | 5  | 4  |

Figure 13K:
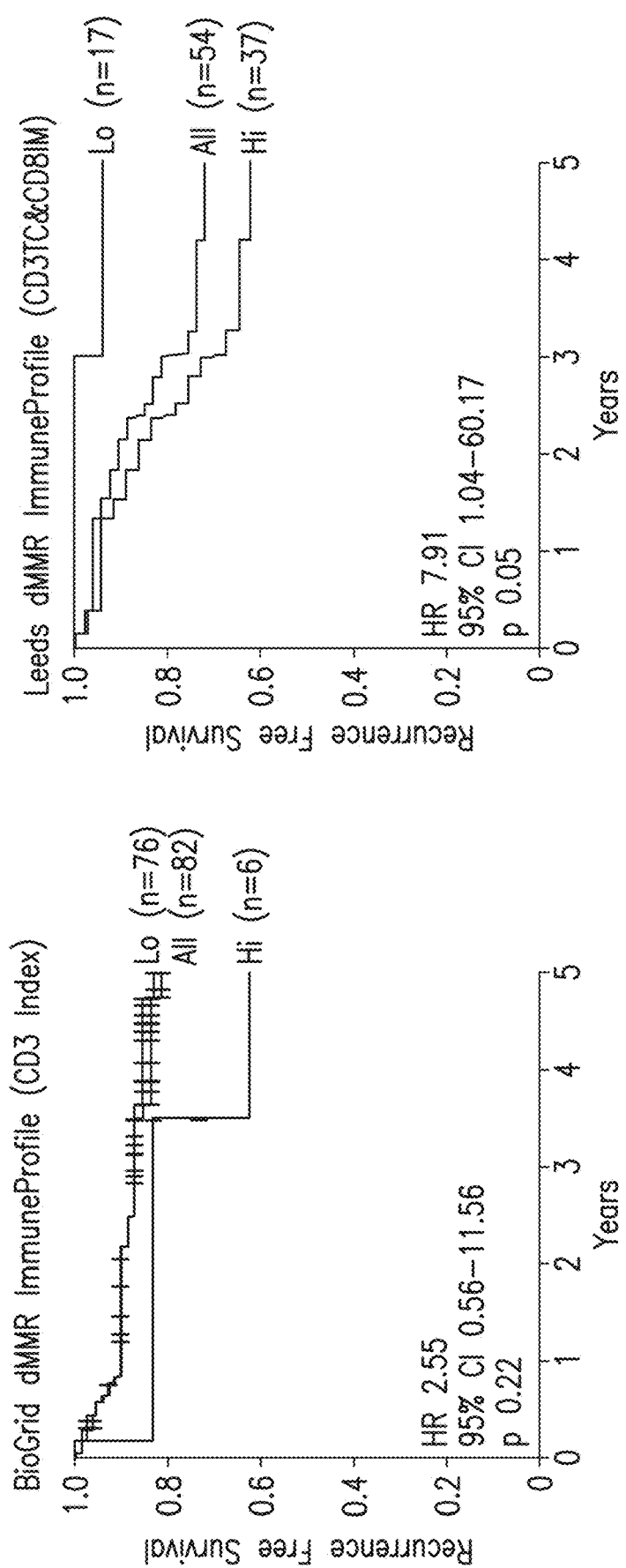

FIG. 13K illustrates Kaplan-Meier curves of dMMR patients from the BioGrid and Leeds cohorts stratified by combining clinical variables and immune context score using a model combination. The chemotherapy status of the risk groups from each stratification is shown below in Table 33:

TABLE 33

|         |         | Low | High |
|---------|---------|-----|------|
| BioGrid | Naïve   | 64  | 5    |
|         | Treated | 12  | 1    |
| Leeds   | Naïve   | 11  | 25   |
|         | Treated | 6   | 12   |

The number of patients at risk at each time point is set forth in Table 34:

TABLE 34

| Year      |      | 0  | 1  | 2  | 3  | 4  | 5  |
|-----------|------|----|----|----|----|----|----|
| Model     | Low  | 76 | 64 | 60 | 54 | 42 | 30 |
|           | High | 6  | 5  | 5  | 5  | 2  | 1  |
| Covariate | Low  | 17 | 17 | 17 | 17 | 16 | 16 |
|           | High | 37 | 35 | 32 | 26 | 24 | 23 |

VII. Exemplary Image Analysis System and Clinical Workflow

In clinical practice, the continuous scoring function may be integrated into prognostic analysis and making treatment decisions. After biopsy or surgical resection of the tumor, a representative tissue block showing a tumor cross-section from the patient's tumor sample is chosen for analysis. At least three 4 μm thick sections are cut from this tissue block, and transferred to glass slides. The sections are stained as:
1. CD3 negative control (i.e. staining protocol with primary antibody diluent in place of primary antibody)
2. CD3 IHC
3. H&E
4. CD8 IHC (optional)
5. CD8 neg. control (optional).

All sections are scanned on a slide scanner. The H&E slide is scanned at 20× magnification with 0.496 μm pixel size. The CD3 and CD8 IHC slides and negative control slides are scanned at 40× magnification with 0.25 um pixel size. Images are transferred to a Digital Pathology system together with slide metadata. Slide metadata includes an identification of the tumor sample and the staining of the slide (H&E, CD3 IHC, CD8 IHC, or negative control) and can either be entered by a user when scanning a slide or automatically obtained from a laboratory information system. The Digital Pathology system uses the slide metadata to trigger the execution of automated CD3 cell counting for CD3 IHC slides and the execution of automated CD8 cell counting for CD8 IHC slides (if used). Optionally, a user can choose one or more CD3 or CD8 IHC slides and trigger the respective automated cell counting.

In the Digital Pathology system, a pathologist or expert observer opens the digital image of the H&E slide in viewing software to understand relevant morphologic areas to score. The user then annotates the tumor using annotation tools provided by the viewing software. Typically, the tumor is defined by creating one or more outlines and identifying them as tumor outlines. Using the same viewing software, the user then indicates the portion of tumor outline which is the invasive margin. For this, the user creates additional outlines that intersect with the tumor outline. The intersections define the beginning and end of sections on the tumor outline that are involved in an invasive process. The new outlines are identified as invasive margin.

The user then triggers the automated transfer of the tumor and invasive margin annotations onto the adjacent CD3 and CD8 IHC slides (if CD8 slides are used). The Digital pathology system offers a registration function that transfers annotations onto adjacent slides, taking position, orientation, and local deformations of the tissue section into account. The user opens the CD3 IHC and CD8 IHC slide images in the viewer software and controls the location of the automatically registered tumor and invasive margin annotations. The viewer software offers tools to modify and edit annotations if this is necessary. Editing functions include shifting annotations, rotating annotations, and locally modifying their outlines. The user further examines the CD3 IHC and CD8 IHC slide images in the viewer software for tissue, staining, or imaging artifacts. The user delineates such artifact regions with annotations and identifies them to be excluded from analysis.

In the Digital Pathology system, the user may choose one or more CD3 and CD8 IHC slides and triggers the report generation. The user will obtain quality control reports, which may include the following components:

A low- to mid-resolution image that shows all tissue on the slide

The same low- to mid-resolution image overlaid with the outline and/or transparent colored regions that indicate the morphologic regions of interest like the tumor and the invasive margin. The invasive margin will be automatically created from the user annotations using predefined sizes or distances to the tumor outline. Furthermore, regions that are annotated to be excluded from the analysis are overlaid in this image.

The same low- to mid-resolution image with automatically generated small rectangular markers that indicate the position of high-resolution FOVs for quality control Each of the high-resolution FOVs Each of the high-resolution FOVs overlaid with markers that indicate the presence of each CD3+ or CD8+ lymphocyte that was determined by automated cell counting.

As an option, the morphologic regions of interest and markers indicating the cells from automated cell counting can also be presented in the viewer software.

The user reviews the QC data and decides to accept or reject the case. For accepted cases, the Digital Pathology system reports quantitative readouts and passes them to a scoring module. These quantitative readouts may include:

The area of each morphologic region of interest in mm².

The number of cells in each morphologic region of interest.

Descriptive statistics that describe the spatial distribution of the cells in each morphologic region of interest.

Additional information about the samples may further be input into the Digital Pathology system, such as, for example, MMR status, prior exposure of the subject to a therapy (such as chemotherapy, radiation therapy, and/or a targeted therapy), tumor scores using a TNM staging system, and/or overall tumor stage, and clinical variables (such as age, sidedness of the tumor, number of lymph nodes harvested, and sex of the patient), which may be used by the system to, for example, select an appropriate scoring function to apply to the image. Additionally or alternatively, the user may select an appropriate continuous scoring function based on such criteria or other criteria. The scoring module calculates the $ICSc_{ox}$, which may be reported as a raw number. Additionally, a binning function may be applied to the $ICS_{cox}$ to assign the patient to a risk bin (for example, by applying cutoffs between populations based on "high risk" and "low risk" of recurrence or "likely to respond" or "unlikely to respond" to adjuvant chemotherapy) and/or a population stratification bin (for example, a quartile or decile bin based on $ICS_{cox}$); and/or a ranking function to rank the $ICS_{cox}$. The clinician reviews the report and discusses results with patient deciding on clinical pathologist-based results.

REFERENCES

Anitei et al., *Prognostic and Predictive Values of the Immunoscore in Patients with Rectal Cancer*, Clinical Cancer Res., Vol. 20, Issue 7, pp. 1891-1899 (2014).

Chen & Srinivas, *Automatic Lymphocyte Detection in H&E Images with Deep Neural Networks*, arXiv:1612.03217v1 (submitted 9, Dec. 2016; available at arxiv.org).

Forrest et al., *Comparison of visual and automated assessment of tumour inflammatory infiltrates in patients with colorectal cancer*, European J. Cancer, Vol. 50, Issue 3, pp. 544-552 (2014).

Galon et al., *Towards the introduction of the 'Immunoscore' in the classification of malignant tumours*, J. Pathol., Vol. 232, Issue 2, pp. 199-209 (2014).

Galon et al., *Validation of the Immunoscore (IM) as a prognostic marker in stage I/II/III colon cancer: Results of a worldwide consortium-based analysis of 1,336*

*patients*, J. Clin. Oncol., Vol. 34, suppl. Abstract No. 3500 (2016) (available at meetinglibrary.asco.org) ("Galon (2016a)").

Galon et al., *Validation of the Immunoscore (IM) as a prognostic marker in stage I/II/III colon cancer: Results of a worldwide consortium-based analysis of 1,336 patients*. Powerpoint presentation (2016) (available at meetinglibrary.asco.org) ("Galon (2016b)").

Jass, *Lymphocytic infiltration and survival in rectal cancer*, J. Clin. Pathol., Vol. 39, Issue 6, pp. 585-589 (1986).

Jass et al., *A new prognostic classification of rectal cancer*, The Lancet, Vol. 329, Issue 8545, pp. 1303-1306 (1987).

Mei et al., *Tumour-infiltrating inflammation and prognosis in colorectal cancer: systematic review and meta-analysis*, British J. Cancer, Vol. 110, pp. 11595-1605 (2014).

Pagès et al., *Immune infiltration in human tumors: a prognostic factor that should not be ignored*, Oncogene, Vol. 29, pp. 1093-1102 (2010).

Venook et al., *Impact of primary (1°) tumor location on overall survival (OS) and progression free survival (PFS) in patients (pts) with metastatic colorectal cancer (mCRC): Analysis of CALGB/SWOG 80405 (Alliance)*, J Clin Oncol 34,2016 (suppl; abstr 3504).

---

The invention claimed is:

1. A method of prognosing a patient having a stage II colorectal tumor, the method comprising:
   (a) obtaining:
      (a1) a digital image of a tissue section of the stage II colorectal tumor stained for CD3; and
      (a2) a digital image of a tissue section of the stage II colorectal tumor stained for at least one additional marker selected from a group consisting of CD8, CD4, FoxP3, CD45RA, and CD45RO;
   (b) quantitating, on an image analysis system:
      (b1) a CD3+ cell density within a region of interest (ROI) selected from a group consisting of a tumor core (TC) region, an invasive margin (IM) region, and/or a peritumoral (PT) region of the tissue section; and
      (b2) a density of cells staining for the at least one additional marker within a ROI selected from a group consisting of a TC region, an IM region, and/or a PT region of the tissue section; and
   (c) applying a non-linear continuous scoring function to a feature vector comprising the CD3+ cell density and the density of cells staining for the at least one additional marker to obtain an immune context score (ICS) for the tumor, wherein the ICS is indicative of the prognosis of the patient, and wherein the non-linear continuous scoring function is derived from a Cox proportional hazard model of formula 1:

$$ICS_{cox} = \exp(b_1 X_1 + b_2 X_2 + \ldots b_p X_p) \quad \text{Formula 1}$$

wherein:
   $X_1, X_2, \ldots X_p$ are independent variables, the independent variables including the CD3+ cell density and the density of cells staining for the additional marker and/or a combination of the CD3+ cell density and the density of cells staining for the additional marker for the ROI; and
   $b_1, b_2 \ldots b_p$ are constants extrapolated for each of the independent variables; and
   (d) prognosing the patient at least in part on the basis of the ICS.

2. The method of claim 1, wherein the digital image of the tissue section of the colorectal tumor stained for CD3 is a serial section of the digital image of the tissue section the colorectal tumor stained for at least one additional marker.

3. The method of claim 1, wherein the cell densities of the feature vector are derived from an area cell density obtained by dividing a quantity of labeled cells in the ROI by an area of the ROI.

4. The method of claim 1, wherein the cell densities of the feature vector are derived from a mean or median area cell density of a plurality of control regions of the ROI.

5. The method of claim 1, wherein the non-linear continuous scoring function derived from the Cox proportional hazard model comprises a function according to formula 2:

$$ICS_{cox} = \exp(-b_1 * CD3_D - b_2 * CD8_D + b_3 * CD3_D * CD8_D) \quad \text{Formula 2}$$

wherein:
   $CD3_D$ is the density of CD3+ cells of the ROI,
   $CD8_D$ is the CD8+ cell density of the ROI, and
   $b_1$, $b_2$, and $b_3$ are constants obtained from applying a Cox proportional hazard model to a dataset comprising recurrence-free survival data, CD3+ cell density data, and CD8+ cell density data obtained from a cohort of colorectal cancer patients, and wherein $|b_1|>|b_2|>|b_3|$.

6. The method of claim 5, wherein the $CD3_D$ and $CD8_D$ are normalized cell densities and/or subject to maximum and/or minimum cutoffs.

7. The method of claim 1, wherein prognosing the patient comprises comparing the calculated ICS to a pre-determined cutoff separating a good prognosis from a bad prognosis.

8. The method of claim 1, wherein prognosing the patient on the basis of the ICS comprises assigning the calculated ICS to a percentile rank of ICS scores.

9. The method of claim 1, wherein prognosing the patient on the basis of the ICS comprises integrating the ICS with one or more clinical variables selected from a group consisting of age of the patient, sex of the patient, sidedness of the tumor, and number of lymph nodes harvested from the patient.

10. The method of claim 9, wherein the clinical variables and the ICS are integrated by a model combination or a covariate combination.

11. The method of claim 1, wherein the patient is chemo-naïve and the colorectal tumor is determined to be mismatch repair proficient (pMMR).

12. A system for scoring an immune context of a tissue sample, the system comprising a processor and a memory coupled to the processor, the memory to store computer-executable instructions that, when executed by the processor, cause the processor to perform a set of operations comprising the method of claim 1.

13. A non-transitory computer readable storage medium for storing computer-executable instructions that are executed by a processor to perform a set of operations comprising the method of claim 1.

* * * * *